(12) United States Patent
Davies et al.

(10) Patent No.: US 8,776,788 B2
(45) Date of Patent: Jul. 15, 2014

(54) SHEET DRIVER FOR USE IN A DRUG DISPENSER

(75) Inventors: Michael Birsha Davies, Ware (GB); Robert William Tansley, Bidford on Avon (GB)

(73) Assignee: Glaxo Group Limited, Brentford, Middlesex (GB)

( * ) Notice: Subject to any disclaimer, the term of this patent is extended or adjusted under 35 U.S.C. 154(b) by 921 days.

(21) Appl. No.: 12/514,953

(22) PCT Filed: Nov. 13, 2007

(86) PCT No.: PCT/EP2007/062278
§ 371 (c)(1),
(2), (4) Date: May 14, 2009

(87) PCT Pub. No.: WO2008/058964
PCT Pub. Date: May 22, 2008

(65) Prior Publication Data
US 2010/0059052 A1   Mar. 11, 2010

(30) Foreign Application Priority Data

Nov. 15, 2006   (GB) .................................. 0622827.4

(51) Int. Cl.
| | | |
|---|---|---|
| *A61M 15/00* | (2006.01) |
| *B65D 83/04* | (2006.01) |
| *B65D 83/06* | (2006.01) |
| *B65H 20/00* | (2006.01) |
| *B65H 18/08* | (2006.01) |
| *B65H 43/00* | (2006.01) |

(52) U.S. Cl.
USPC ........ 128/203.15; 221/25; 221/123; 226/190; 242/534; 242/563

(58) Field of Classification Search
USPC ............. 128/202.21–202.22, 203.15, 203.21, 128/205.23; 226/190; 221/25, 123, 21; 242/534, 563
See application file for complete search history.

(56) References Cited

U.S. PATENT DOCUMENTS 3,269,389 A   8/1966   Meurer et al.
3,759,095 A * 9/1973   Short et al. ...................... 73/157
(Continued)

FOREIGN PATENT DOCUMENTS

DE   1461280   2/1969
EP   0469814   2/1992
(Continued)

OTHER PUBLICATIONS

Office Action issued Feb. 3, 2011 for U.S. Appl. No. 11/573,656.
(Continued)

*Primary Examiner* — Jackie T Ho
*Assistant Examiner* — Mark Wardas
(74) *Attorney, Agent, or Firm* — James P. Riek

(57) ABSTRACT

A sheet driver for use in a drug dispenser where the sheet driver includes a shaft with a shaft cavity co-axial with a rotational axis of the shaft and a hub that defines a hub aperture, where within the shaft cavity there is an indicator pin having a side member and an indicator pin head that may project through the hub aperture, where within the shaft cavity there is a spring for biasing said indicator pin out of the shaft cavity, and where an engagement member may selectively engage said side member of the indicator pin to prevent movement of the engagement member upon the occurrence of an fault condition of the sheet driver.

10 Claims, 33 Drawing Sheets

(56) References Cited

U.S. PATENT DOCUMENTS

| | | | |
|---|---|---|---|
| 4,224,824 A * | 9/1980 | Giusti | 73/159 |
| 4,735,358 A | 4/1988 | Morita et al. | |
| 4,811,731 A | 3/1989 | Newell et al. | |
| 4,892,426 A * | 1/1990 | Steele | 400/708 |
| 4,940,966 A | 7/1990 | Pettigrew et al. | |
| 5,002,048 A | 3/1991 | Makiej, Jr. | |
| 5,007,419 A | 4/1991 | Weinstein et al. | |
| 5,060,883 A | 10/1991 | Ohya et al. | |
| 5,320,095 A | 6/1994 | Nijkerk et al. | |
| 5,437,267 A | 8/1995 | Weinstein et al. | |
| 5,447,151 A * | 9/1995 | Bruna et al. | 128/203.15 |
| 5,462,205 A | 10/1995 | Keller | |
| 5,497,765 A | 3/1996 | Praud et al. | |
| 5,505,704 A | 4/1996 | Pawelka et al. | |
| 5,582,162 A | 12/1996 | Petersson | |
| 5,590,645 A * | 1/1997 | Davies et al. | 128/203.15 |
| 5,619,984 A | 4/1997 | Hodson et al. | |
| 5,657,748 A | 8/1997 | Braithwaite | |
| 5,664,557 A | 9/1997 | Makiej, Jr. | |
| 5,740,793 A | 4/1998 | Hodson et al. | |
| 5,772,085 A | 6/1998 | Bryant et al. | |
| 5,787,881 A | 8/1998 | Chawla | |
| 5,830,490 A | 11/1998 | Weinstein et al. | |
| 5,860,419 A | 1/1999 | Davies et al. | |
| 5,873,360 A | 2/1999 | Davies et al. | |
| 5,921,237 A | 7/1999 | Eisele et al. | |
| 5,941,241 A | 8/1999 | Weinstein et al. | |
| 5,998,428 A | 12/1999 | Barnette et al. | |
| 6,029,663 A | 2/2000 | Eisele et al. | |
| 6,095,136 A | 8/2000 | Virtanen | |
| 6,102,179 A | 8/2000 | Hodson et al. | |
| 6,116,237 A | 9/2000 | Schultz et al. | |
| 6,182,655 B1 | 2/2001 | Keller et al. | |
| 6,489,168 B1 | 12/2002 | Wang et al. | |
| 6,810,873 B1 | 11/2004 | Haikarainen et al. | |
| 6,889,690 B2 | 5/2005 | Crowder et al. | |
| 6,941,948 B2 | 9/2005 | Staniforth et al. | |
| 7,775,205 B2 | 8/2010 | Edgerley | |
| 8,201,556 B2 | 6/2012 | Jones et al. | |
| 2001/0015391 A1 | 8/2001 | Katoh | |
| 2001/0027789 A1 | 10/2001 | Goede et al. | |
| 2002/0040713 A1 | 4/2002 | Eisele et al. | |
| 2004/0050864 A1 | 3/2004 | Stradella | |
| 2004/0099676 A1 | 5/2004 | Anderson et al. | |
| 2005/0126568 A1 | 6/2005 | Davies et al. | |
| 2005/0154491 A1 | 7/2005 | Anderson et al. | |
| 2005/0172964 A1 | 8/2005 | Anderson et al. | |
| 2005/0229931 A1 | 10/2005 | Denyer et al. | |
| 2006/0196504 A1 | 9/2006 | Augustyn et al. | |
| 2008/0001967 A1 | 1/2008 | Rengarajan et al. | |
| 2009/0078252 A1 * | 3/2009 | Anderson et al. | 128/202.22 |
| 2010/0059052 A1 | 3/2010 | Davies et al. | |

FOREIGN PATENT DOCUMENTS

| | | |
|---|---|---|
| EP | 0521434 | 1/1993 |
| EP | 0751077 | 1/1997 |
| EP | 1300171 | 4/2003 |
| GB | 612750 A | 11/1948 |
| GB | 1387954 | 3/1975 |
| GB | 2242134 | 9/1991 |
| GB | 2327408 | 1/1999 |
| WO | 9212402 | 7/1992 |
| WO | 9631790 | 10/1996 |
| WO | 9830332 | 7/1998 |
| WO | 9834664 | 8/1998 |
| WO | 9851257 | 11/1998 |
| WO | 9939991 | 8/1999 |
| WO | 0000411 | 1/2000 |
| WO | 0045879 | 8/2000 |
| WO | 0051599 | 9/2000 |
| WO | 0064519 | 11/2000 |
| WO | 0064520 | 11/2000 |
| WO | 0104118 | 1/2001 |
| WO | 0117595 | 3/2001 |
| WO | 0124690 | 4/2001 |
| WO | 0126020 | 4/2001 |
| WO | 0126021 | 4/2001 |
| WO | 0126720 | 4/2001 |
| WO | 0139823 | 6/2001 |
| WO | 0141849 | 6/2001 |
| WO | 0168169 | 9/2001 |
| WO | 0197886 | 12/2001 |
| WO | 0198176 | 12/2001 |
| WO | 0200279 | 1/2002 |
| WO | 0204055 | 1/2002 |
| WO | 0224268 | 3/2002 |
| WO | 02053294 | 7/2002 |
| WO | 03024514 | 3/2003 |
| WO | 03035151 | 5/2003 |
| WO | 03035509 | 5/2003 |
| WO | 03061743 | 7/2003 |
| WO | 03080149 | 10/2003 |
| WO | 03090811 | 11/2003 |
| WO | 03090825 | 11/2003 |
| WO | 03095010 | 11/2003 |
| WO | 2004011070 | 2/2004 |
| WO | 2004012801 | 2/2004 |
| WO | 2004054646 | 7/2004 |
| WO | 2004067069 | 8/2004 |
| WO | 2005014089 | 2/2005 |
| WO | 2005037353 | 4/2005 |
| WO | 2005079727 | 9/2005 |
| WO | 2006018261 A1 | 2/2006 |
| WO | 2007012871 | 2/2007 |

OTHER PUBLICATIONS

Amendment filed Apr. 29, 2011 in response to Office Action issued Feb. 3, 2011 for U.S. Appl. No. 11/573,656.

Notice of Allowance issued Feb. 21, 2012 for U.S. Appl. No. 11/573,656.

U.S. Appl. No. 11/573,656—Interview Summary Dated May 18, 2012.

* cited by examiner

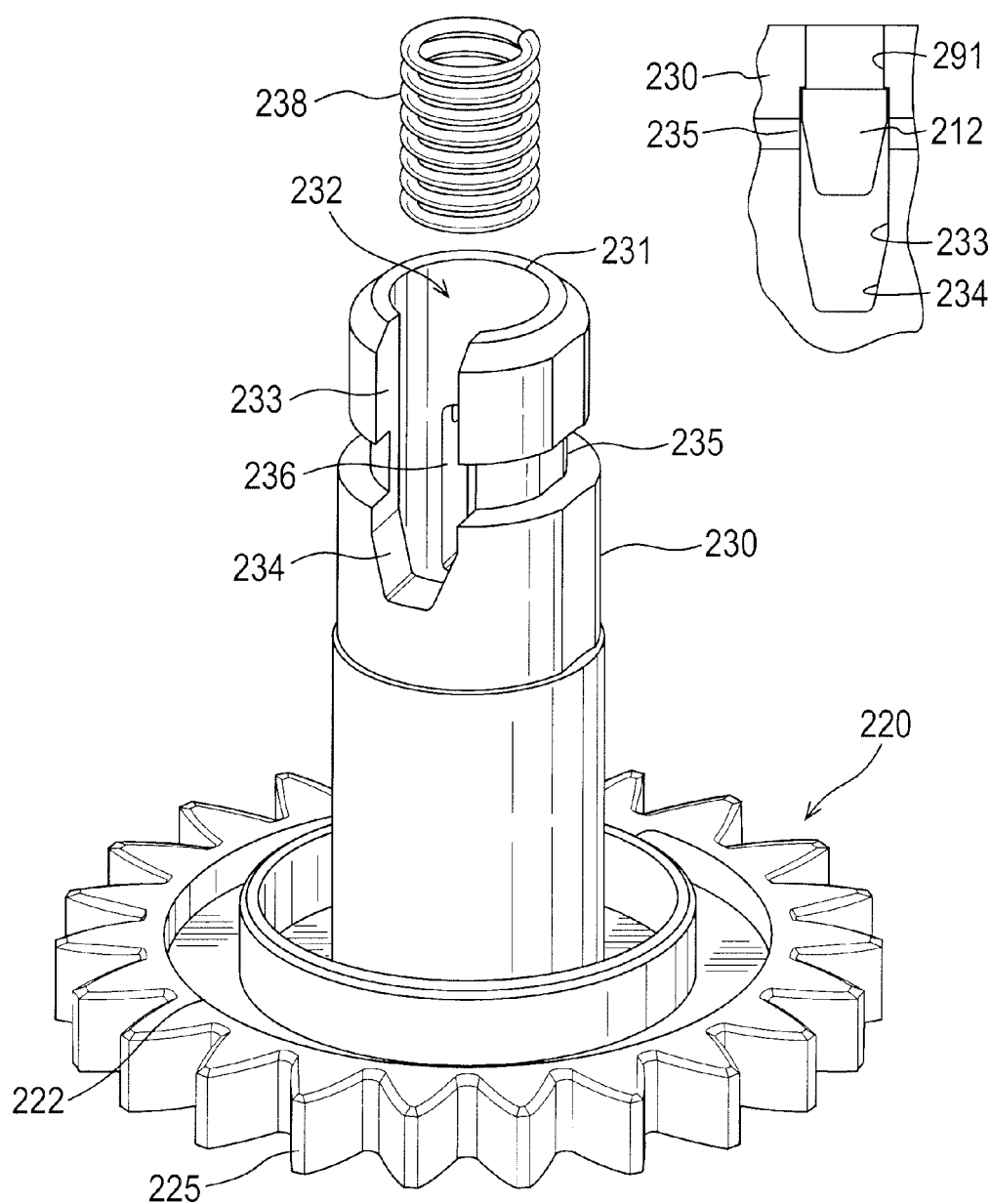
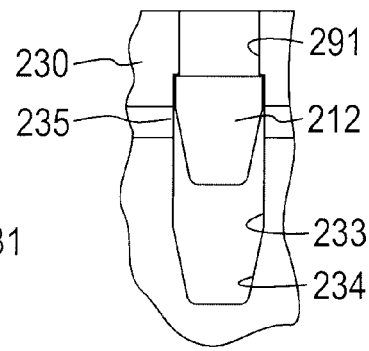
FIG. 2a
FIG. 8

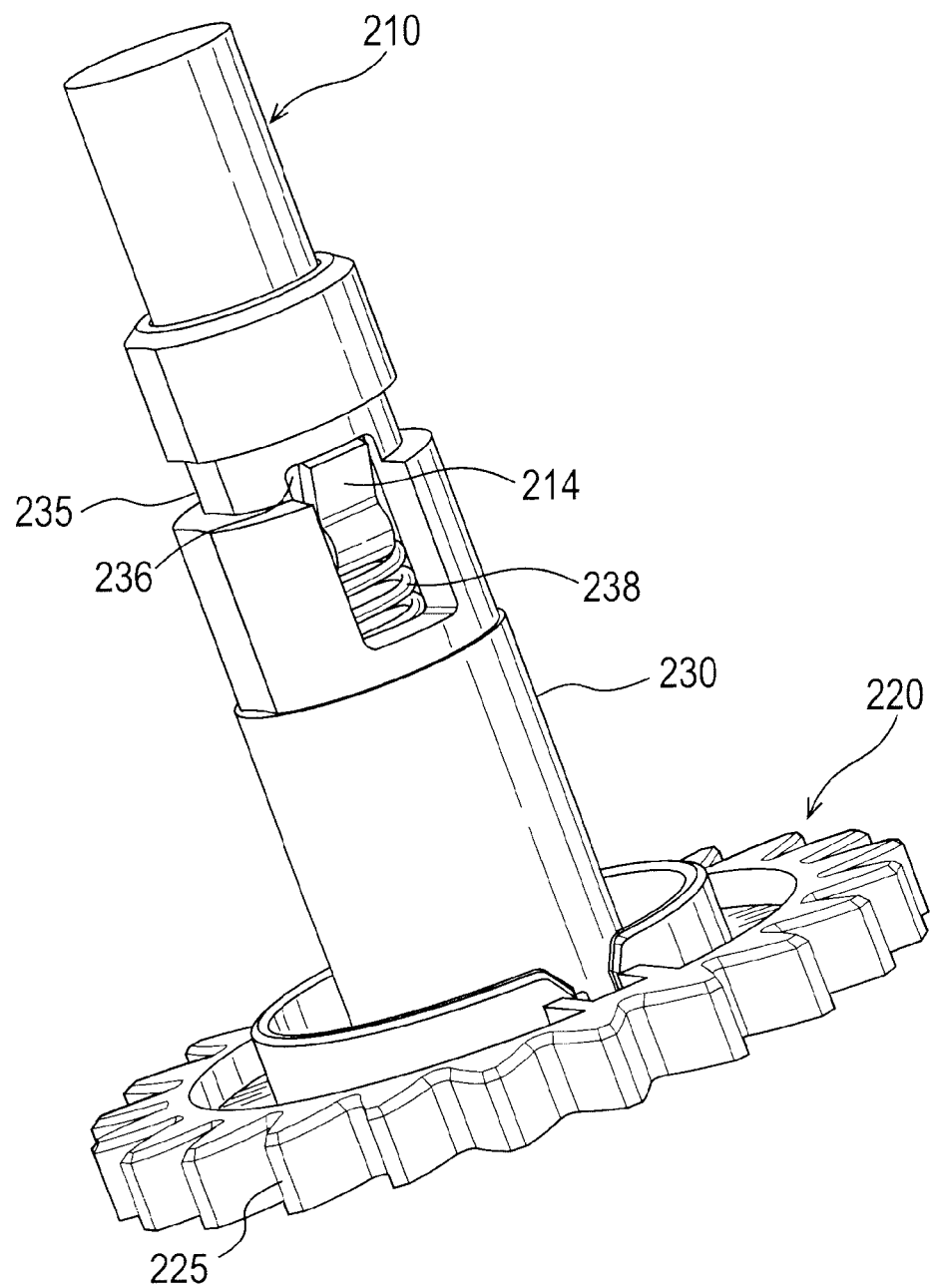

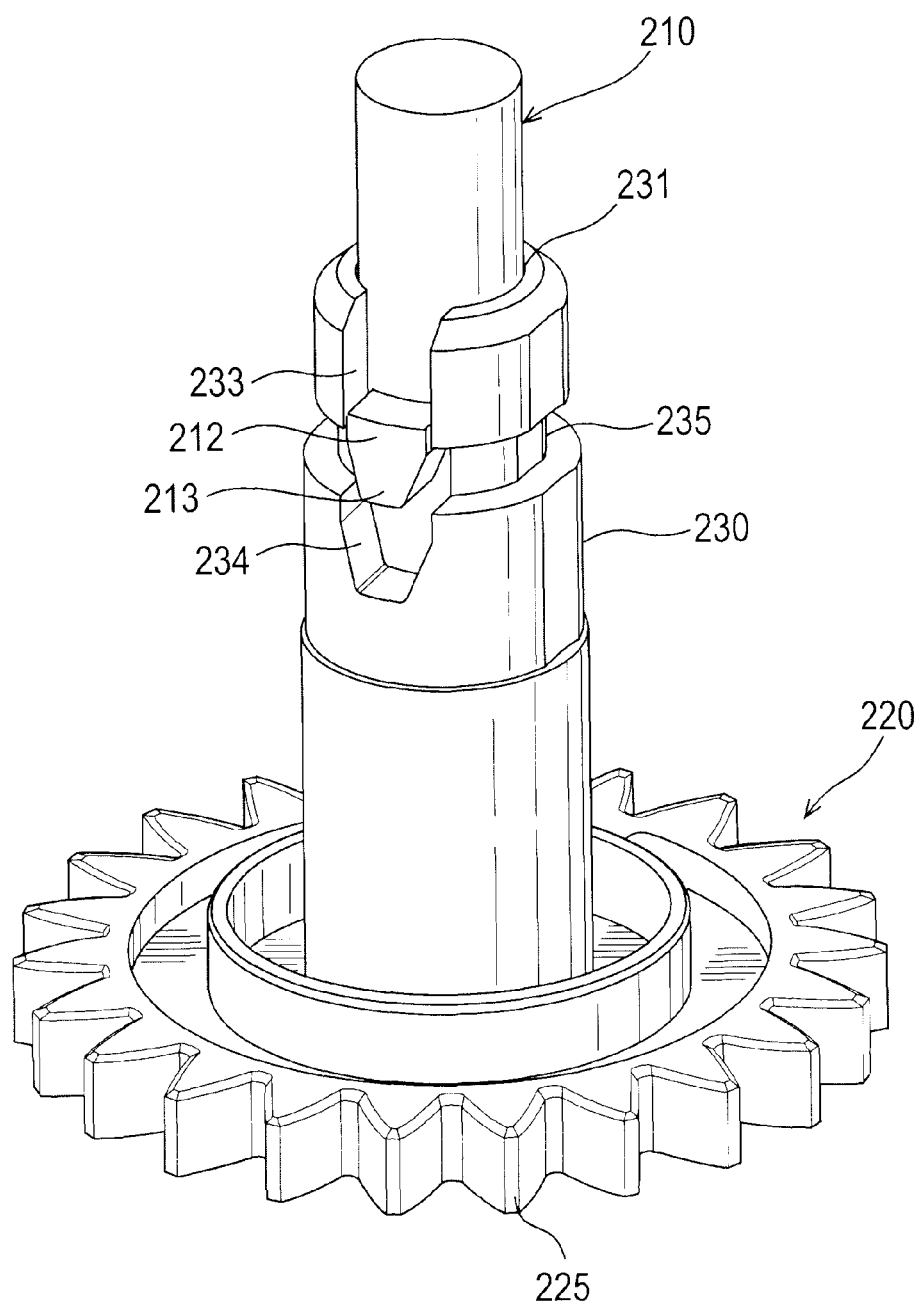

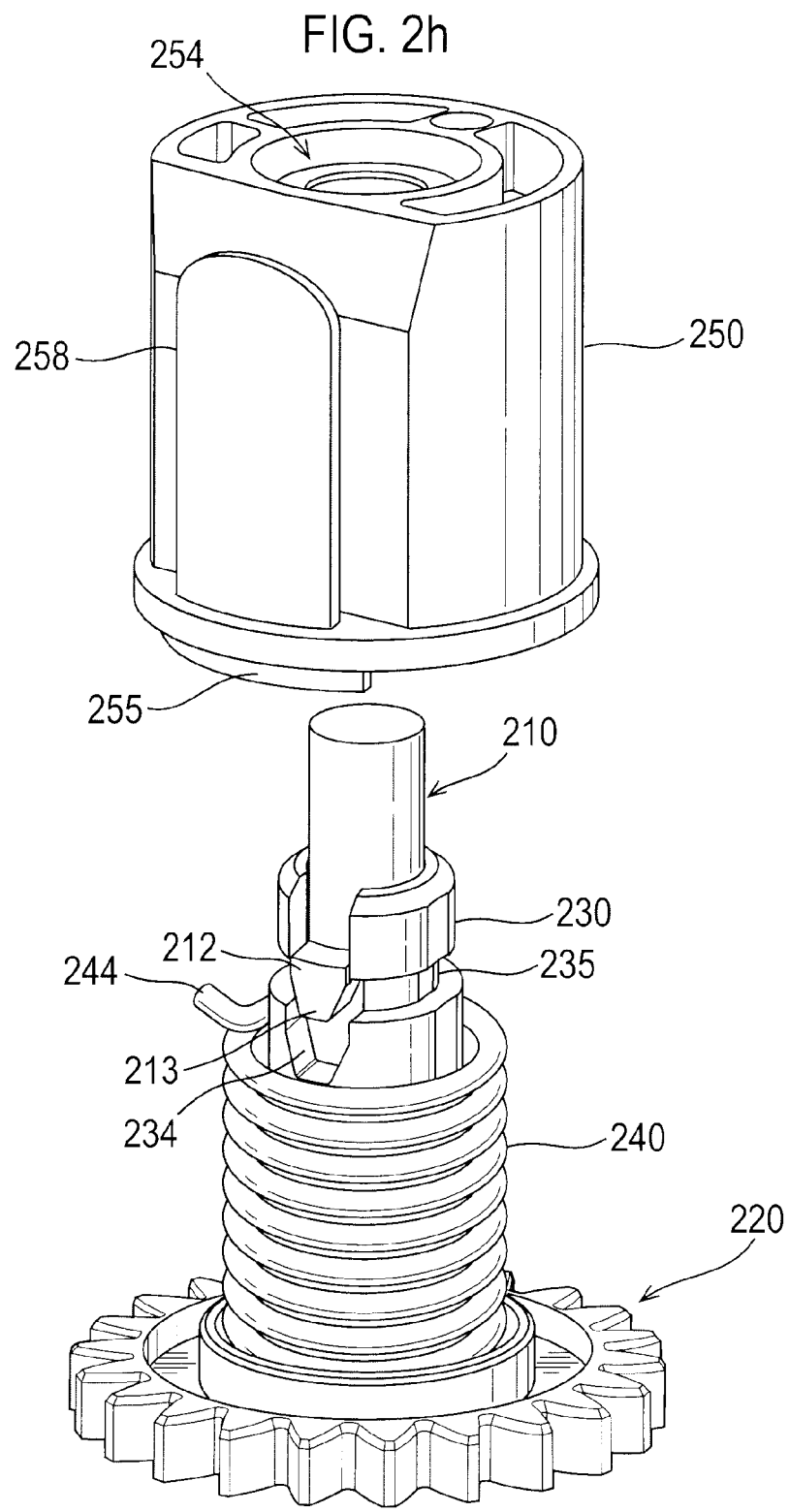

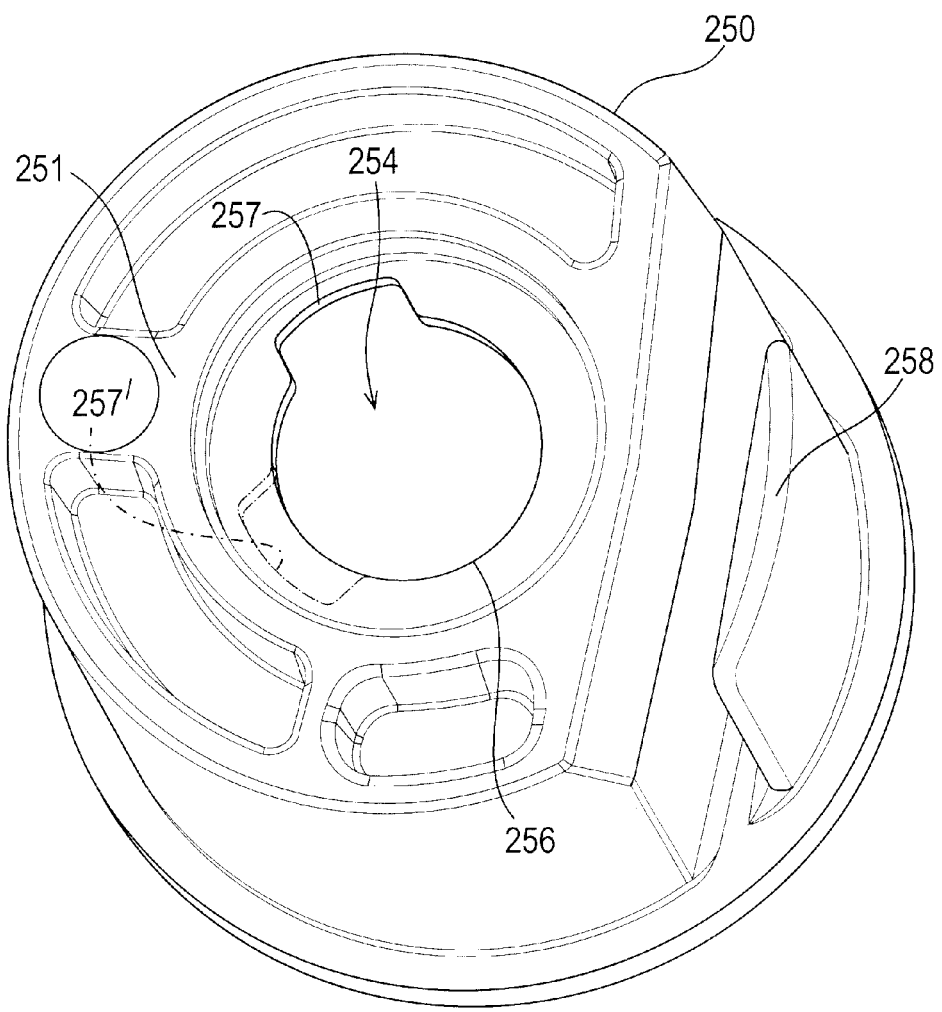

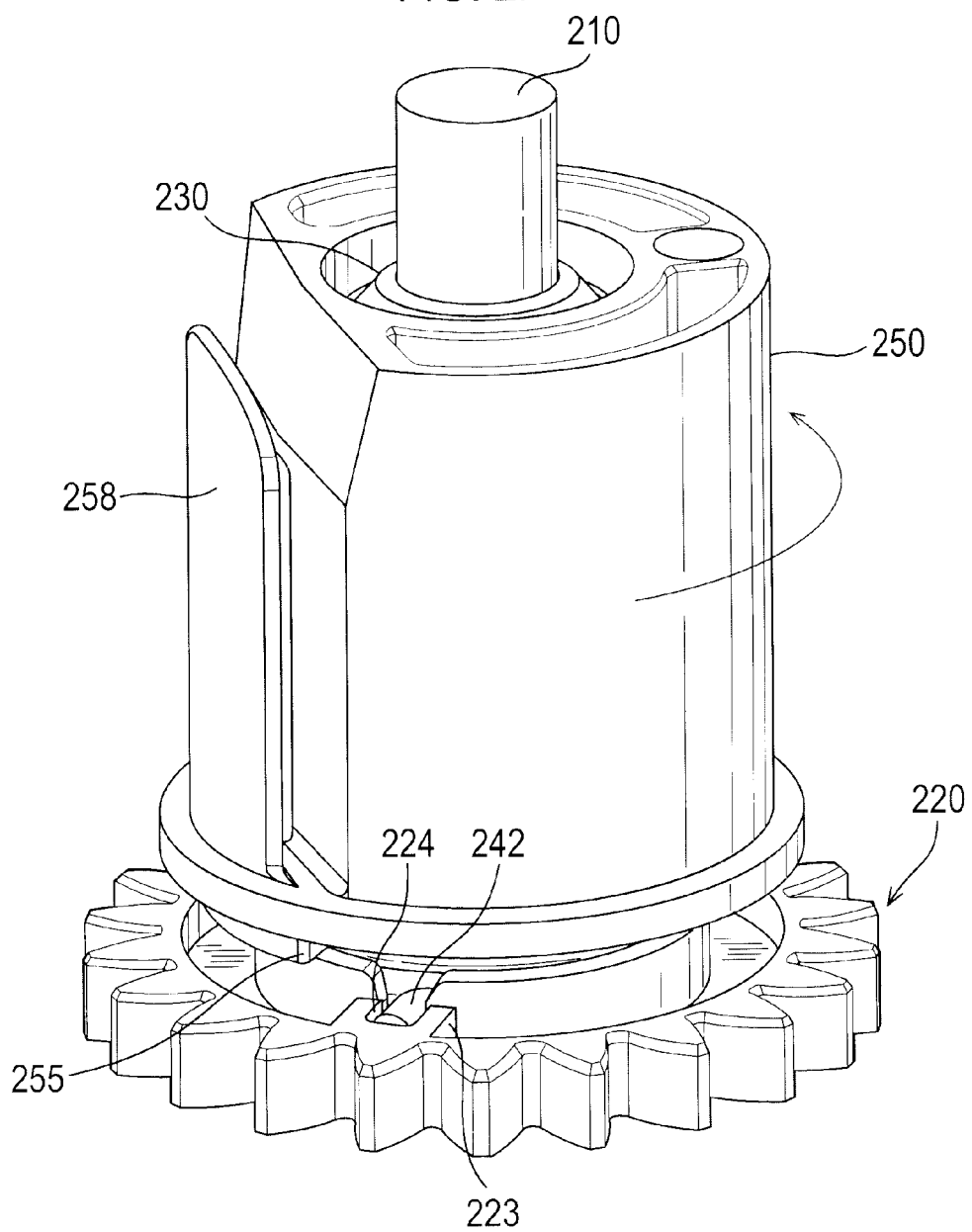

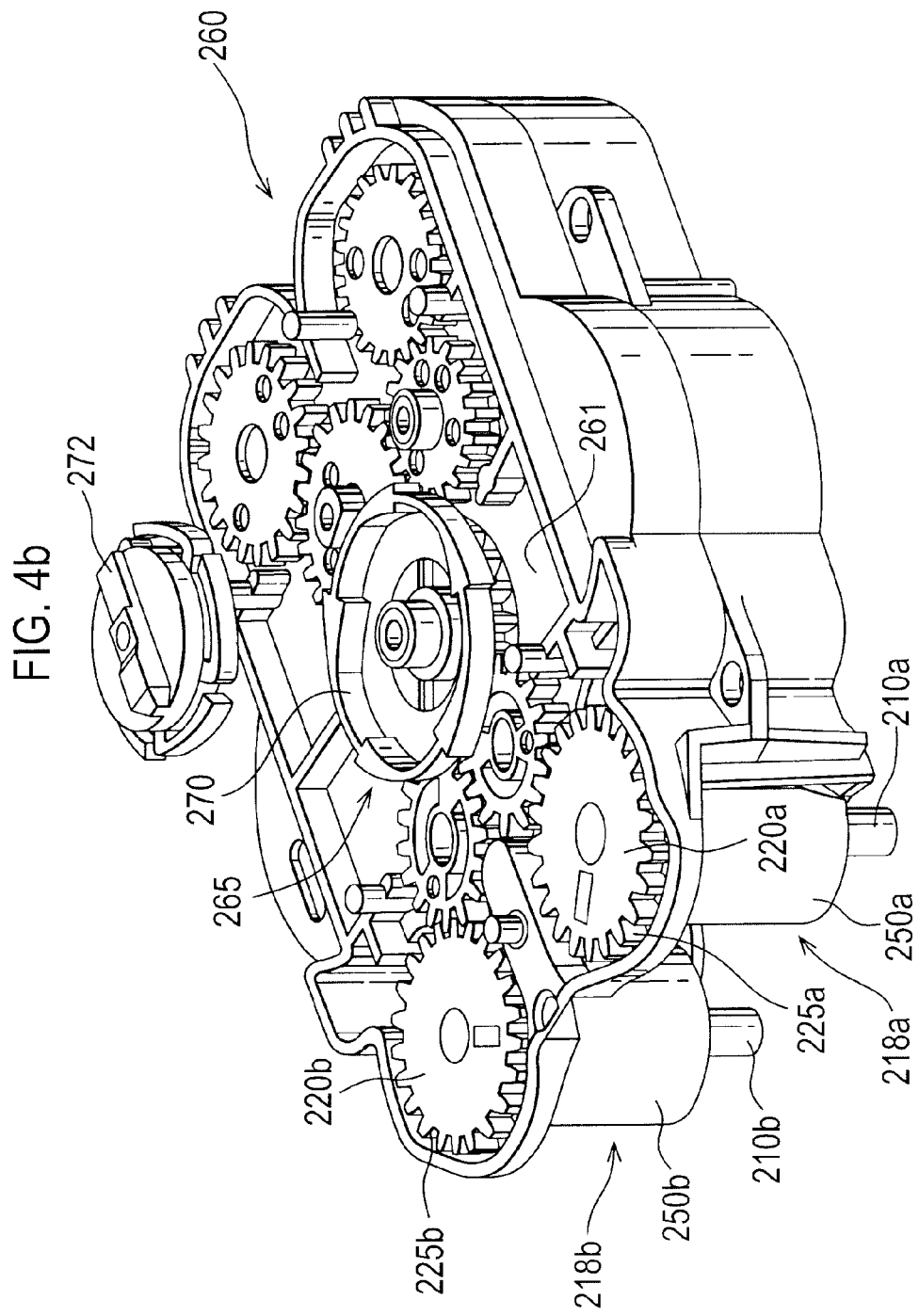

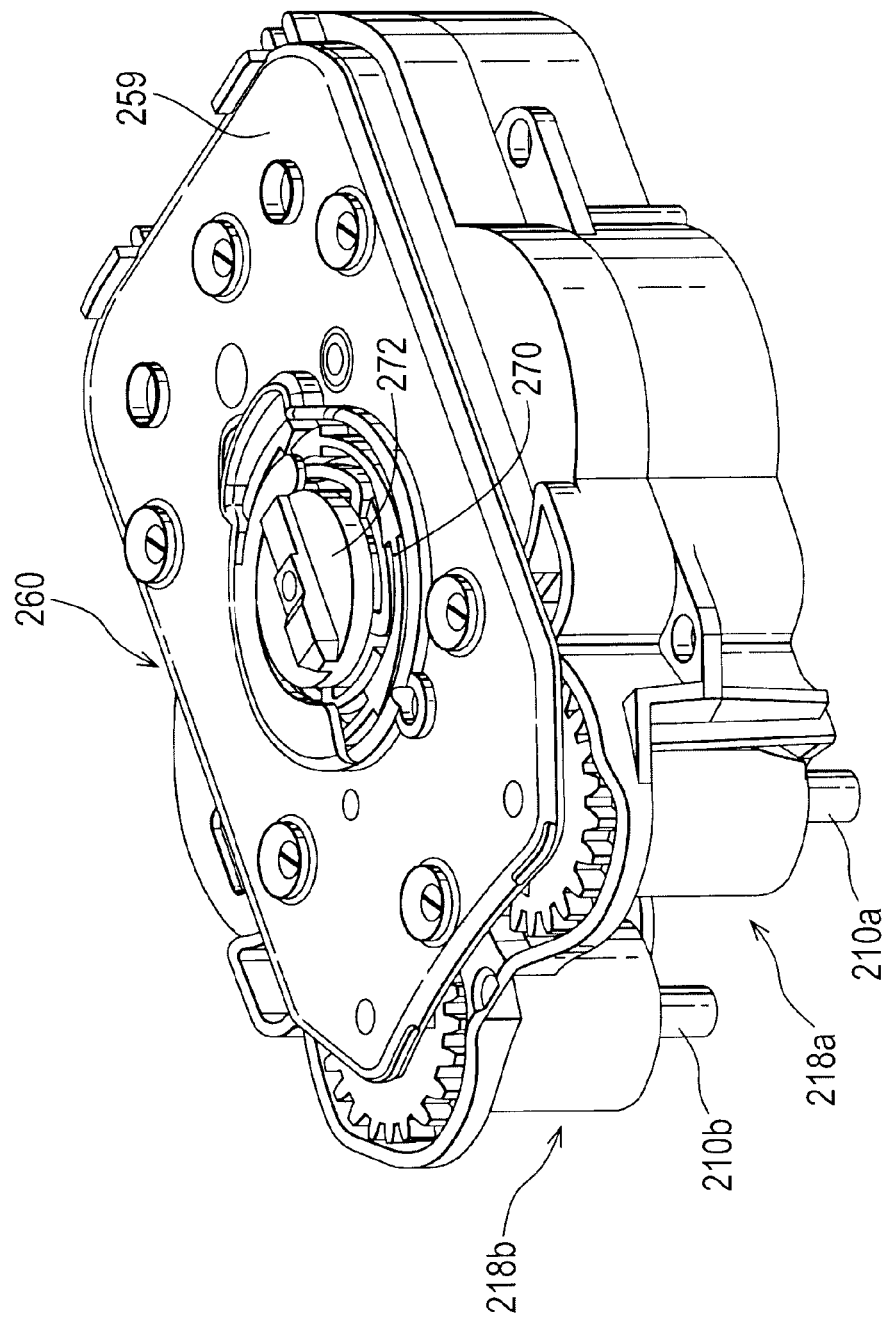

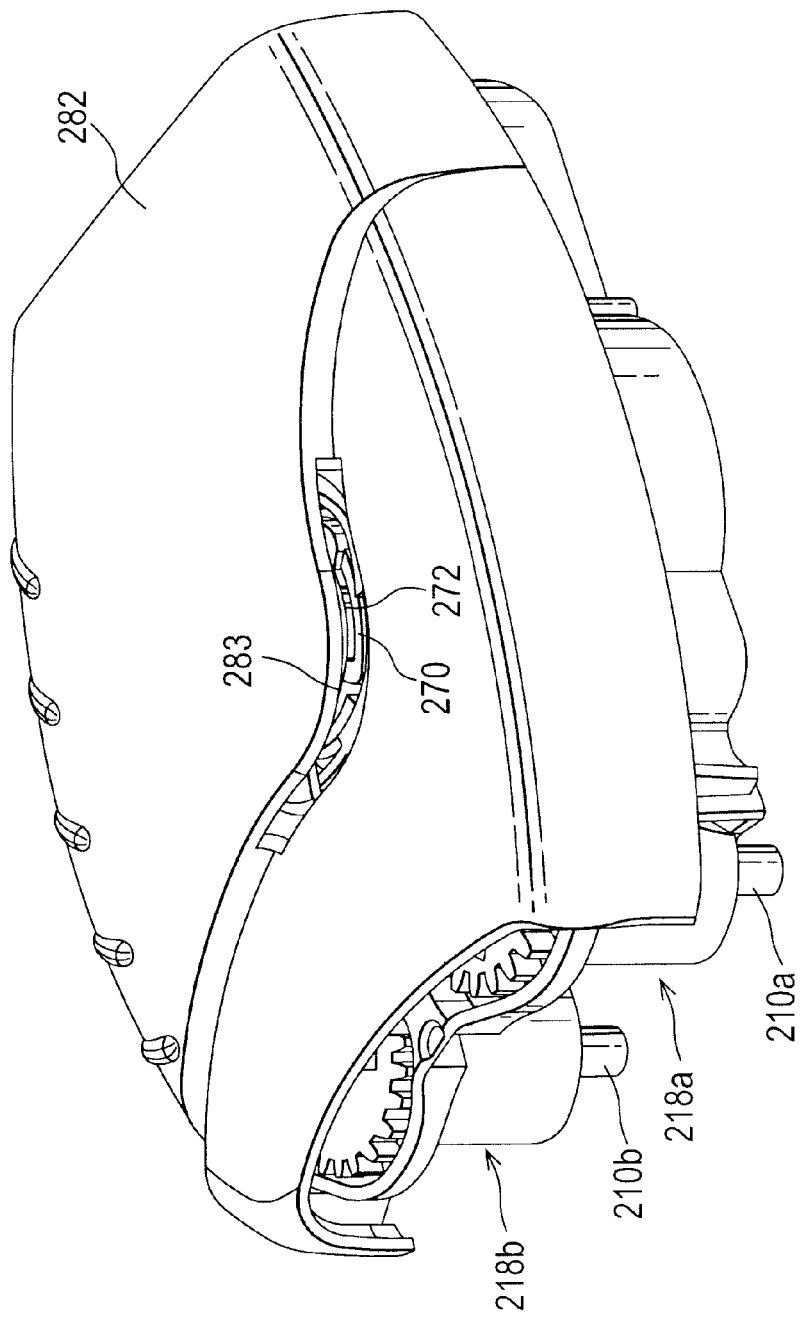

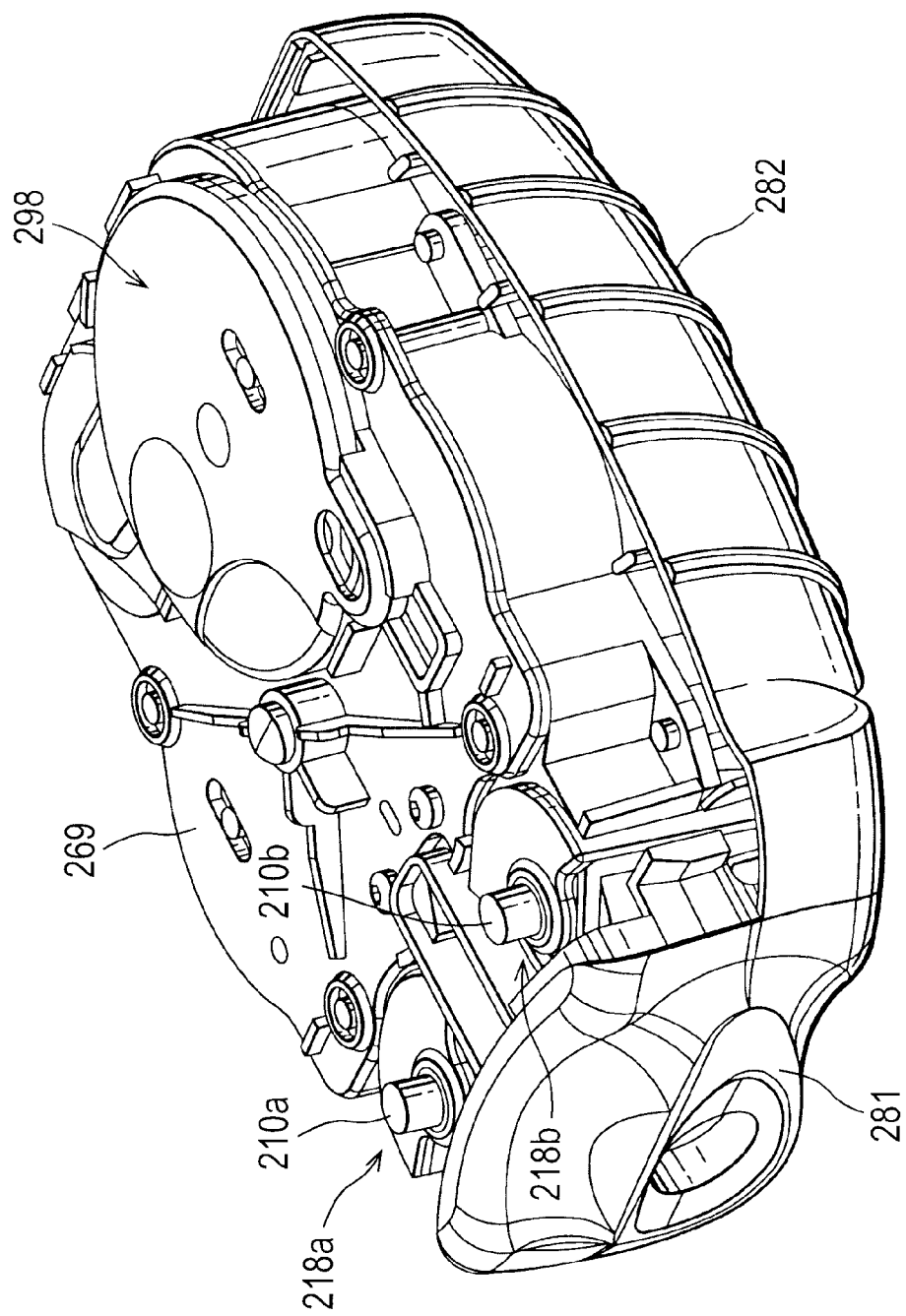

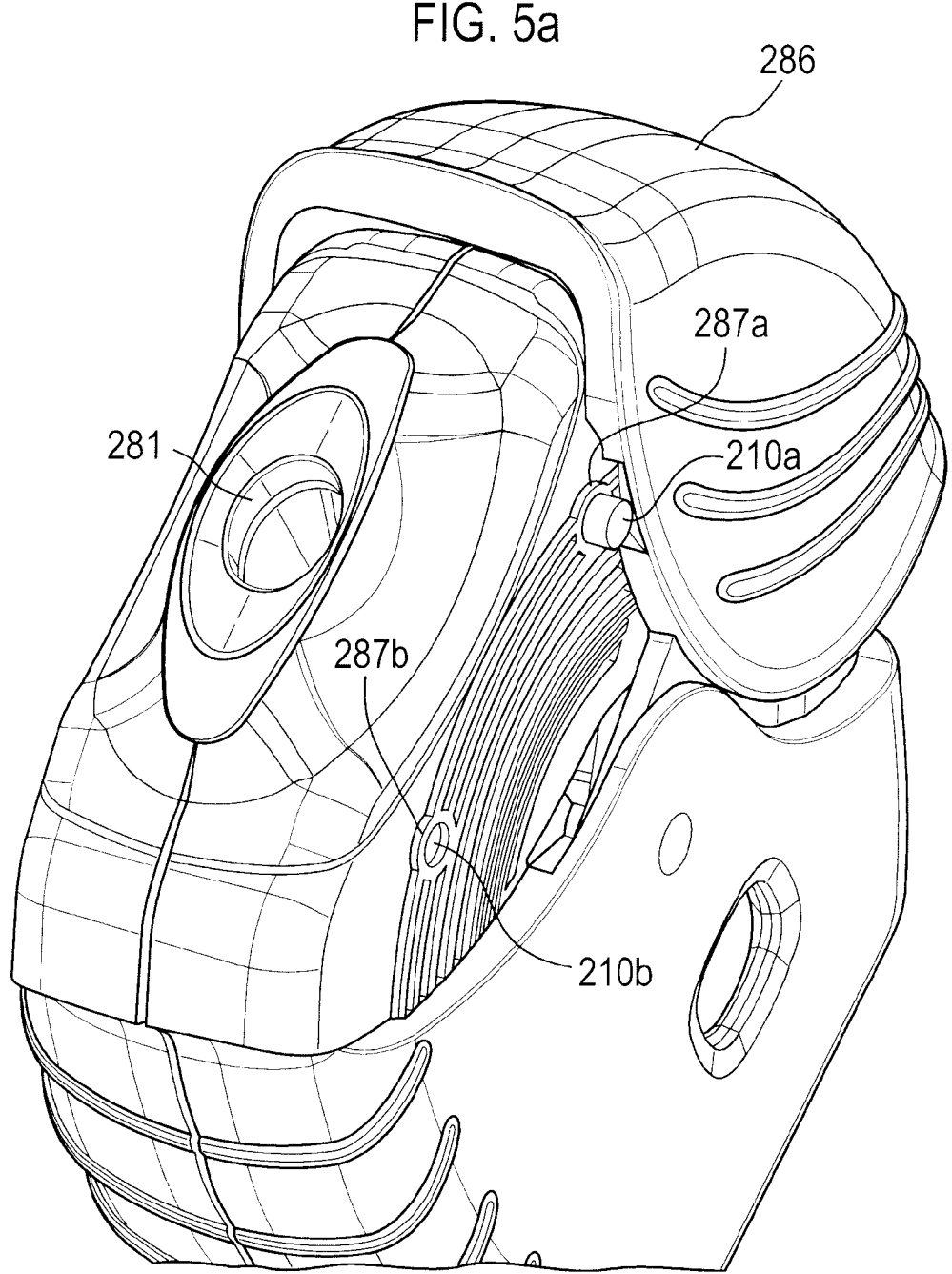

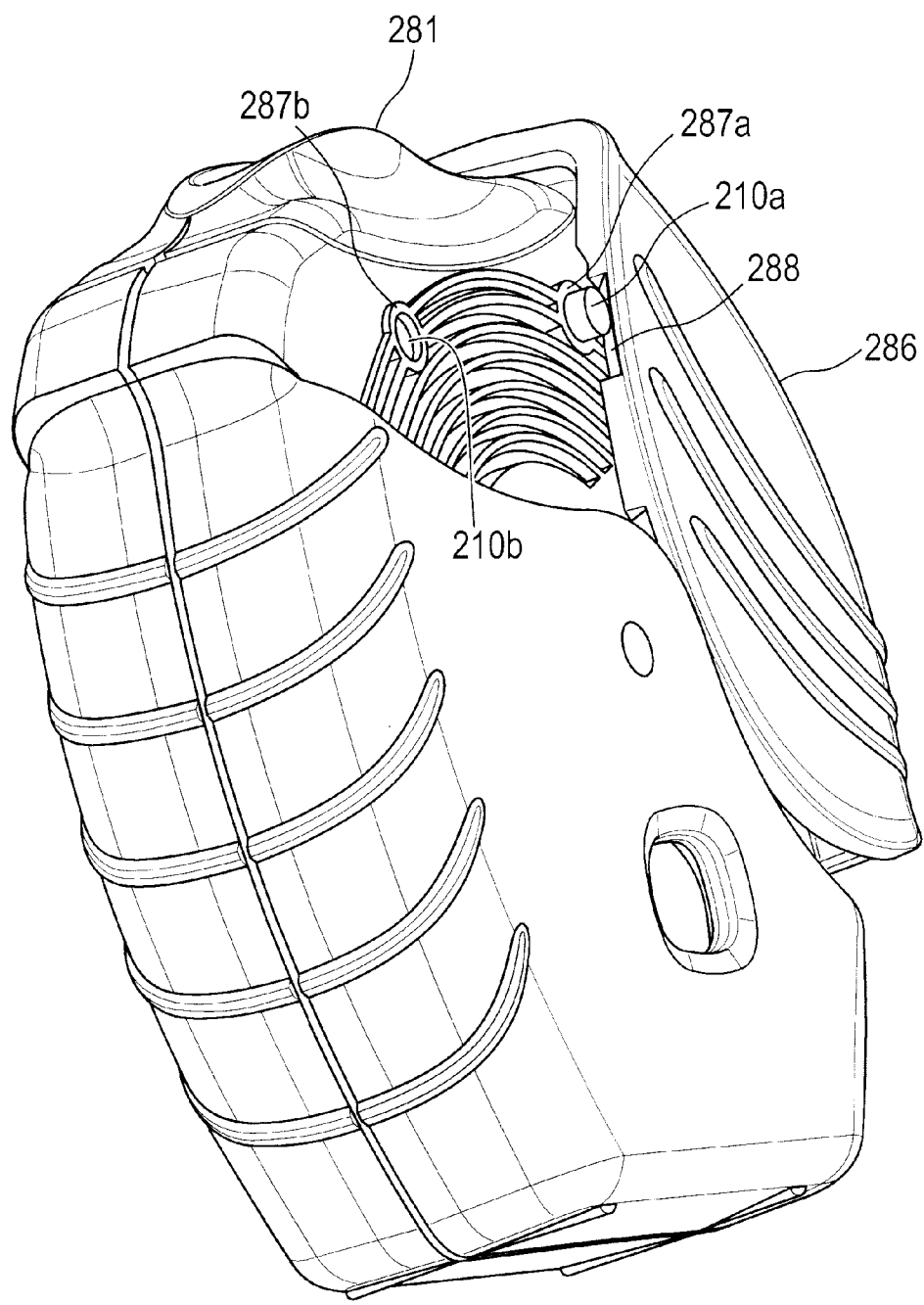

SHEET DRIVER FOR USE IN A DRUG DISPENSER

CROSS-REFERENCE TO RELATED APPLICATIONS

This application is filed pursuant to 35 U.S.C. §371 as a United States National Phase Application of International Patent Application Serial No. PCT/EP2007/062278 filed Nov. 13, 2007, which claims priority from Great Britain Application No. 0622827.4 filed in the United Kingdom on Nov. 15, 2006.

TECHNICAL FIELD

The present invention relates in one aspect to a sheet driver component suitable for use in a drug dispenser for dispensing drug, in which drug in powder or tablet form is carried by an elongate blister strip comprising a base sheet having pockets defined therein and a lid sheet provided thereto. In another aspect, the present invention relates more generally to a spool for winding up a tape.

BACKGROUND TO THE INVENTION

The use of drug dispensers in the administration of drugs, for example in bronchodilation therapy is well known. Such dispensers generally comprise a body or housing within which a drug carrier is located. A known drug dispenser has a drug carrier in the form of an elongate blister strip containing a number of discrete doses of drug in powder or tablet form. The elongate blister strip comprises a base sheet having pockets defined therein and a lid sheet provided thereto, wherein the base sheet and lid sheet are peelably separable to allow access to the contents of each pocket. The lid sheet and base sheet typically comprise laminated foil materials. Such dispensers typically contain a mechanism of sequentially accessing the dose-containing pockets, for example comprising peeling means for peeling the lid sheet away from the base sheet. The drug is thereby made available for delivery to the patient.

Suitable peeling means are positioned to peel apart a base sheet and a lid sheet of a pocket at an opening station of the dispenser. The peeling means typically includes a (lid or base) sheet driver for pulling apart a lid sheet from a base sheet of a pocket that has been received at the opening station. In one embodiment, the sheet driving means comprises a fixed-diameter wheel on which the (e.g. lid) sheet is wound, the wheel having an effective winding surface, the diameter of which increases as more (e.g. lid) sheet is wound about said wheel.

A problem encountered with the use of such a fixed-diameter wheel as the sheet driver for driving a sheet of a drug carrier is that as the sheet winds up around the wheel the effective winding diameter of the wheel increases, and therefore its effective lateral pulling action (i.e. length of pull) also increases. This is problematic because it is desirable that on actuation, a definable pull action is experienced by the drug carrier pocket at the opening station to ensure that a generally uniform indexing/opening effect is experienced by each pocket of the drug carrier. In general terms, insufficient pull action will result in failure to open up the pocket whilst excess pull will put stress on the mechanical components and increase the force required to actuate the dispenser.

A solution to the above problem has been described in Applicant's PCT Patent Application No. WO-A-2006/018261 and counterpart U.S. Ser. No. 11/573,656, the disclosures of which are incorporated herein by reference. Therein is described a (lid or base) sheet driver having the form of a hub incorporating compensating means in the form of a central shaft-mounted torsion spring to compensation for the increase in effective winding diameter.

Another problem that can potentially be encountered is that a sheet (i.e. lid sheet or base sheet) of the elongate blister strip may become damaged during use, for example as a result of tearing, stretching or de-lamination thereof. A reduction (or complete lack) of 'sheet pulling force' is thereby, experienced at the (lid or base) sheet driver, which impairs or prevents the ability of the sheet driver to correctly wind up the sheet thereon. As a result, the pockets containing drug are also not advanced correctly and/or are not peelably opened fully or at all by the pocket opening mechanism of the dispenser. The ability of the drug dispenser to make drug available for delivery to the patient is therefore either substantially impaired or entirely prevented, which 'failure' can have serious consequences for the patient. The 'failure' can be compounded where the patient does not realize that the strip advancement and/or pocket opening mechanism of the drug dispenser has been impaired, and the patient continues to use the dispenser unaware that drug delivery is not happening correctly or at all. It is thus, desirable to provide a clear indication to the patient of the 'failure' of the dispenser.

In solution, the Applicant has devised a sheet driver that includes an indicator pin that 'pops out' when loss of pulling force (as would normally be applied by an undamaged sheet) is experienced at the sheet driver. In a development of the solution, the indicator pin can be made to engage in locking fashion one or more elements of the drug dispenser when in its 'popped out' position, thereby preventing any further use of the dispenser. The patient is thereby, given a very clear message that the dispenser has 'failed' and that a replacement must be obtained. More generally, the Applicant has devised a spool for winding up a tape which is provided with a fault indicator to indicate a fault with the tape.

Applicant's co-pending PCT Patent Application No. WO-A-2006/123110, the disclosure of which is incorporated herein by reference, describes a fault indicator mechanism for use with a drug dispenser in which an elongate blister strip is advanced to various blister opening positions.

SUMMARY OF THE INVENTION

According to one aspect of the present invention there is provided a sheet driver for use in a drug dispenser including a drug carrier having a plurality of pockets for containing drug wherein said pockets are spaced along the length of and defined between first and second sheets secured to each other and separable by drivable pulling action, said sheet driver comprising (a) a base;
(b) extending from said base, a shaft defining a rotational axis;
(c) at said base, a drive surface for receipt of drive to rotate the base about said rotational axis;
(d) about said shaft, a torsion spring defining first and second spring legs;
(e) mounting about the shaft and said torsion spring for rotation about the rotational axis, a hub defining a hub surface for receipt of a sheet of said drug carrier; and
(f) a first leg receiver of the base for receipt of said first spring leg of the torsion spring a second leg receiver of said hub for receipt of said second spring leg of the torsion spring such that relative rotation of the base and the hub results in tensioning of the torsion spring, wherein the shaft further defines a shaft cavity co-axial with the rotational axis and the hub further defines a hub aperture, the sheet driver further comprising (g) within said shaft cavity, an indicator pin having a side member and an indicator pin head that may project through said hub aperture;

(h) also within the shaft cavity, a spring for biasing said indicator pin out of the shaft cavity; and (i) provided to the hub, an engagement member for selectively engaging said side member of the indicator pin to prevent movement thereof along the rotational axis in response to the relative positioning of the base and the hub.

According to another aspect of the present invention there is provided a spool as set forth in claim 1 hereof.

The present invention provides a sheet driver for use in a drug dispenser including a drug carrier having a plurality of pockets for containing drug wherein said pockets are spaced along the length of and defined between first and second sheets secured to each other and separable by drivable pulling action.

The sheet driver comprises a base, typically of circular form (e.g. disc-shaped).

Extending (e.g. typically ascending) from the base, there is provided a shaft. The shaft may be formed integral with the base or it may be provided as a separate part to the base for fixing thereto. The shaft defines a rotational axis about which the hub is rotatable. The shaft also defines a shaft cavity that is co-axial with the rotational axis, the function of which will be described in more detail later.

Provided at the base, there is a drive surface for receipt of drive to rotate the base about the rotational axis. In embodiments, the base has circular form and the drive surface extends circumferentially about the base.

Preferably, the drive surface is geared (i.e. defines a gearing surface), although other types of drive surfaces are envisaged including those responsive to frictional and belt drives.

In one embodiment, the drive surface is integral with the base. In embodiments, the base defines a rim and the drive surface is provided to the rim.

In another embodiment, the drive surface is provided to a separate part, which associates with the base.

In a particular embodiment, the drive surface is provided to a ring that fits over and is received by (e.g. engaged by) a rim of the base. In embodiments, the drive surface is provided to the outer circumferential surface of the ring.

In one embodiment, the inner circumferential surface of the ring is also provided with gearing and the base is provided with a ratchet arm such that the base and ring are in ratcheted engagement. Such ratcheted engagement provides that the ring may only be rotated relative to the base in one rotational sense (e.g. only clockwise or only anti-clockwise) with rotation in the other rotational sense being prevented by the ratchet interaction between inner, geared surface of the ring and the ratchet arm of the base.

About the shaft, there is provided a torsion spring. The term 'spring' herein is used to mean any resilient spring-like means, which may be tensioned. The torsion spring defines first and second spring legs that typically extend away (e.g. protrude) from the ends (e.g. top and bottom) of the spring.

In embodiments, the spring is a coiled spring. In one embodiment, the spring legs protrude away from the spring in a direction perpendicular to the rotational axis defined by the coils of the spring. In another embodiment, the spring legs protrude away from the spring in a direction parallel to the rotational axis defined by the coils of the spring.

Mounted about the shaft and the torsion spring for rotation about the rotational axis, there is provided a hub defining a hub surface for receipt of a lid or base sheet, preferably a lid sheet of said drug carrier. Any suitable means of mounting the hub to the shaft are envisaged including snap-fit and interference mountings. The hub generally fits over the torsion spring and shaft. The hub itself has a fixed diameter, although its effective winding diameter (i.e. wheel plus thickness of lid or base sheet wound there around) will vary in use as a sheet is accommodated thereby. The hub is typically of solid construction and essentially incompressible in nature, at least about its diameter. The hub also defines a hub aperture, which preferably centres on the rotational axis, the function of which will be described in more detail later.

In embodiments, the hub is mounted about the shaft such that it is rotatable in either a clockwise or anti-clockwise sense relative to the base and hence such that the torsion spring may also be tensed in one or other sense.

In embodiments, the hub is provided with engaging means for engaging the end of a sheet. In one embodiment, the engaging means comprise surface markings or coatings provided to the hub to enhance the frictional contact between the hub and the sheet. In another embodiment, loop-engaging means (e.g. a peg, hook, notch or slot) are provided to the hub for engaged receipt of a looped end of a sheet.

The torsion spring of the sheet driver herein, acts to compensate for any increase in the diameter of the effective winding surface of the fixed-diameter hub during winding of sheet thereabout. It is therefore essential that the sheet driver allow for tensioning of the torsion spring. Accordingly, a first leg receiver of the base receives the first spring leg of the torsion spring and a second leg receiver of the hub receives the second spring leg of the torsion spring such that relative rotation of the base and the hub results in tensioning of the torsion spring.

The sheet driver comprises a fixed-diameter hub on which said base or lid sheet, preferably lid sheet is wound, said hub having an effective winding surface, the diameter of which increases as more sheet is wound about said hub.

The torsion spring of the sheet driver acts to compensate for any increase in the diameter of the effective winding surface of the fixed-diameter hub during use of the dispenser and to thereby ensure that said drug carrier is uniformly indexed upon each actuation of said dispensing mechanism. The torsion spring also acts to ensure that a minimum peeling force between the base sheet and lid sheet is present during actuation of the dispensing mechanism.

In particular, the torsion spring act such as to vary the drive function characteristics of the hub to compensate for any increase in the diameter of the effective winding surface of the hub during use of the dispenser. Thereby, the drug carrier is uniformly indexed (i.e. typically indexed by the same length of strip) as a result of each actuation of the dispensing mechanism, and the pocket opening action experienced by the strip is also uniform.

It will have been appreciated that the torsion spring functions such as to compensate for an increase in the diameter of the effective winding surface of the wheel during use of the dispenser. It will be appreciated that the initial effective winding surface and associated initial drive 'speed' of the hub is principally a function of the (fixed) initial diameter of the hub. Variations are envisaged herein where that initial effective winding surface is selected to define particularly selected initial drive characteristics of the hub.

In one variation sometimes called 'one way take up' mode, the initial effective winding surface is selected such as to initially provide ideal (i.e. uniform) indexing of the drug carrier. As lid sheet winds up around the hub the effective winding surface increases and the torsion spring acts such as to compensate for that increase.

In another variation sometimes called 'two way take up' mode, the initial effective winding surface is selected such as to initially provide non-ideal (i.e. non-uniform) indexing of the drug carrier because the diameter of the hub is insufficiently great. As lid sheet winds up around the hub the effective winding surface increases to an ideal diameter and then on further winding up continues to increase to a non-ideal (i.e. too great diameter). In this embodiment it will be appreciated that the degree and nature of compensation provided by the torsion spring will vary over the winding up function. The torsion spring initially acts such as to compensate for the insufficient wheel diameter. That compensation then decreases to zero at the point where the diameter of the effective winding surface is ideal. The compensation then progressively acts such as to compensate for a too great effective winding surface. This approach has the advantage of overall reducing the (average) compensating torsion force experienced by the drug carrier from a defined zero (i.e. the ideal) and enables the use of less powerful tensioning means (e.g. a smaller torsion spring). In a preferred aspect of this variation, the ideal effective winding surface diameter is selected to correspond approximately to the point at which half of the lid sheet is wound up on the hub, in which case the average (i.e. mean) compensating action experienced is by the carrier over a full usage cycle is close to zero.

In a preferred aspect, the hub and the base are provided with a lock for mutually locking the rotation of the hub relative to the base. In embodiments, the lock locates at a defined rotational spacing from a start position at which the torsion spring is not tensioned, and the or each locking position (i.e. when lock is engaged) thereby defines a known tensioning of the torsion spring.

In one embodiment, variation of the 'locking position' is achievable by variation of the leg angle defined by the spring leg(s) of the torsion spring.

To apply a known tension to the torsion spring, the hub is therefore rotated (either clockwise or anti-clockwise) from the start position to a particular locking position, at which the lock engages.

In one embodiment, the hub is provided with a locking pin receivable by one or more locking pin receivers of the base. In another embodiment, the base is provided with a locking pin receivable by one or more locking pin receivers of the hub.

The sheet driver of the present invention also provides an indicator pin mechanism for indicating when loss of tension is experienced at the sheet driver. It will be appreciated from the earlier description that tensioning of the torsion spring of the sheet driver results from the relative rotation of the base and the hub, which itself results from the sheet of the drug carrier rotationally pulling on the hub. When that sheet is damaged (e.g. torn, delaminated or stretched) the rotational pulling action of the sheet on the hub is diminished resulting in reduced (or zero) tension being applied by the damaged sheet to the hub. This reduced 'sheet pulling force' allows the torsion spring to more freely act on the hub and base to relatively rotate these elements (in an opposite sense to the rotational pulling action normally applied by the sheet) to return them to their 'start' position. The indicator pin mechanism herein, typically provides an indication (e.g. indicator pin 'popped out') that the relative rotational positioning of the base and hub corresponds to that close to (or for zero 'sheet pulling force', equivalent to) that 'start' position.

To accommodate the indicator pin mechanism, the shaft defines a shaft cavity that is co-axial with the rotational axis. Additionally, the hub defines a hub aperture, which preferably centres on the rotational axis. The shaft cavity typically extends down a significant proportion (e.g. greater than 80%) of the length of the shaft. The shaft cavity and the hub aperture typically define an essentially circular profile. A rim (e.g. an upstanding rim) may be provided to the entry to the shaft cavity and/or to define the hub aperture.

Within the shaft cavity, there is provided an indicator pin. The pin has a side member and an indicator pin head that may project through the hub aperture. The pin typically has a pin body of circular cross-section, and the cross-sectional area of the pin body typically corresponds to the cross-sectional area of the shaft cavity. The head of the indicator pin may in embodiments have the same cross-sectional area as the body of the pin or in other embodiments the head of the indicator pin is enlarged compared to the cross-sectional area of the body of the pin. The indicator pin head in embodiments, has a coloured (e.g. a red) portion to make it visually clearer to the user when the pin is in its 'popped out' state (i.e. projecting significantly through the hub aperture).

The side member typically comprises a projecting member. In embodiments the wall of the shaft, which defines the shaft cavity, is provided with a slot or groove, which typically extends lengthways (i.e. parallel to the rotational axis) along the shaft and the slot or groove is arranged to receive the projecting side member of the pin. The receipt of the projecting member of the pin by the slot or groove of the shaft thereby, acts to guide receipt of the pin by the shaft cavity and prevents rotation of the pin relative to the shaft cavity. In embodiments, the projecting side member is shaped to define a key profile and the slot or groove defines a corresponding lock profile such that once the pin has been sufficiently received within the shaft cavity the key profile of the projecting member is reversibly engaged in 'lock and key' fashion by the lock profile of the slot or groove.

Also within the shaft cavity, there is provided a spring for biasing the indicator pin out of the shaft cavity (i.e. in a 'popped out' direction away from the base). Again, the term 'spring' herein is used to mean any resilient spring-like means, which may be tensioned. In embodiments, the spring is a compression spring.

There is provided to the hub, an engagement member for selectively engaging the side member of the indicator pin to prevent movement thereof along the rotational axis. This selective engagement of the engagement member of the hub with the side member of the pin is responsive to the relative positioning of the base and the hub.

In embodiments, the engagement member of the hub is provided to a rim that extends around (e.g. defines) the hub aperture. In embodiments, the engagement member defines a broken rim form having a part rim and a missing rim segment, wherein the part rim engages the side member of the indicator pin and the missing rim segment allows the side member to project through the hub aperture.

It will be appreciated that the relative positioning of the base and the hub is dependent on the pulling force that the sheet of the drug carrier transmits to the hub. Where no pulling force is exerted (i.e. corresponding to the situation where the hub is disengaged from the sheet or to when the sheet has been substantially damaged or broken), the base and hub may be deemed to be at a 'start position' and the torsion spring is at its 'start' tension. Where normal in use pulling force (i.e. corresponding to the situation where the sheet is undamaged and applying a normal level of rotational pulling force), the base and hub are at a 'normal in use position' in which the hub is rotationally displaced relative to the base relative to the 'start position' and the torsion spring provides tension, which opposes the rotational pull of the sheet. Intermediate positions can also be envisaged in which the rotational displacement of hub relative to the base in somewhere intermediate between the 'start position' and 'normal in use position'.

In embodiments, the selective engagement of the engagement member of the hub with the side member of the pin occurs only when the relative rotational displacement of the base and the hub is above a pre-determined minimum displacement, which generally corresponds to a pre-determined minimum tension in the torsion spring. Thus, in embodiments, the selective engagement of the engagement member of the hub with the side member of the pin occurs only when the relative rotational displacement of the base and the hub is greater than 20°, preferably greater than 30° from a 'start' position.

It will be appreciated that when the selective engagement of the engagement member of the hub with the side member of the pin does not occur (i.e. at low hub/shaft displacement and close to 'start' torsion spring tension values) the indicator pin is free to be acted on by biasing spring to cause the pin to 'pop up' out of the shaft cavity and for its head to clearly project out through the hub aperture. This 'popping out' of the indicator pin may be used of itself, to provide a visual indication of low 'sheet pulling force' at the hub, and hence 'failure' of the sheet of the drug carrier. However, in other embodiments the 'popped out' indicator pin may additionally be used to 'lock out' further use of the drug dispenser by for example, locking an element of a dispensing mechanism thereof.

According to another aspect of the present invention there is provided a drug dispenser for use with one or more drug carriers, each having a plurality of pockets for containing drug wherein said pockets are spaced along the length of and defined between first and second sheets secured to each other and separable by drivable pulling action, said dispenser having an internal dispensing mechanism for accessing said drug contained within each of said one or more drug carriers, said mechanism comprising,
a receiving station for receiving a pocket of each of the one or more drug carriers;
(ii) an opener for opening said pocket of each of the one or more drug carriers on receipt thereof by said receiving station;
(iii) an outlet, positioned to be in communication with an opened pocket through which a user can access drug from such an opened pocket; and
(iv) an indexer for individually indexing the pockets of each of the one or more drug carriers, said indexer being interconnected with said sheet driver such that movement of one correlates with the movement of the other.

In embodiments, the opener comprises a peeler positioned to engage a base sheet and a lid sheet of a pocket which has been received in said receiving station for peeling apart such a base sheet and lid sheet, to open such a pocket, said peeler including a sheet driver as described hereinbefore for pulling apart a lid sheet and a base sheet of a pocket that has been received at said receiving station.

In embodiments, the drug dispenser is a dry powder inhaler with the general form as disclosed in U.S. Pat. Nos. 5,860,419, 5,873,360 and 5,590,645 in the name of Glaxo Group Ltd, each of which is incorporated herein by reference. An example of a drug dispenser of this type is the well-known Diskus (trade mark) inhaler dispenser as sold by GlaxoSmithKline Plc. In other embodiments, the drug dispenser is a dry powder inhaler of the general form disclosed in Applicant's co-pending US patent application No. US-A-2005/154491, the disclosure of which is incorporated herein by reference. In yet other embodiments, the drug dispenser is a dry powder inhaler of the general form disclosed in WO-A-2007/068900, the disclosure of which application, and its US national phase equivalent, is incorporated herein by reference.

In a first embodiment herein, the drug dispenser is designed to receive a single elongate form drug carrier.

In a second embodiment herein, the drug dispenser is designed to receive plural elongate form drug carriers. Preferably, the drug dispenser is designed to receive from two to four such elongate form drug carriers, more preferably two such carriers. In embodiments, in the context of this second embodiment, the distinct drug dose portions releasable from each of the plural drug carriers in combination comprise a defined dose of combination product. That is to say, that when combined together (e.g. on release) the distinct active drug dose portions form a single dose of a 'multi-active' drug treatment.

Suitable drug carriers for use with the drug dispenser herein have multiple distinct dose portions carried thereby. The distinct dose portions are typically arranged in spaced fashion, more preferably in progressive arrangement (e.g. series progression) on the carrier such that each dose portion is separately accessible.

In embodiments, the indexer comprises a rotatable index wheel having recesses therein, said index wheel being engageable with a drug carrier in use with said drug dispenser such that said recesses each receive a respective pocket of the base sheet of a drug carrier in use with said drug dispenser.

Alternatively, the indexer comprises an indexing ratchet which is moveable between a locked position whereby said ratchet engages a pocket on said drug carrier and prevents further peeling thereof, and a release position allowing free movement of said drug carrier, and actuation of said drug dispenser actuates said sheet driver and releases said index ratchet from said drug carrier to allow peeling thereof.

In embodiments, the drug dispenser further comprises an actuating driver for actuating said dispenser wherein said indexing lever is interconnected with said indexer and/or said sheet driver. In embodiments, the actuating driver may couple to or form part of a patient-movable element of the drug dispenser such as a movable mouthpiece cover.

In embodiments, the peeler additionally comprises a guide for guiding the lid sheet and base sheet along separate paths at the receiving station. The lid sheet is passed around the guide portion onto the sheet driver. In embodiments, the guide comprises a roller mechanism. The lid sheet is fed over the rollers onto the sheet driver.

In embodiments, the internal dispensing mechanism additionally comprises a first chamber in which the strip is initially housed and from which it is dispensed and a second chamber to receive the used portion of the base sheet after it has been indexed and separated from the lid sheet.

In embodiments, the 'popped out' indicator pin head of the sheet driver is arranged to 'lock out' further use of the drug dispenser by for example, locking an element of the internal dispensing mechanism as described above.

Thus, in embodiments the indicator head of the indicator pin is arranged to selectively engage and lock the opener (e.g. the peeler) and/or the indexer of the internal dispensing mechanism. To facilitate this engagement and lock, the opener (e.g. the peeler) and/or the indexer of the internal dispensing mechanism may in embodiments, be provided with a pin-receiving element sized and shaped for receipt of the indicator pin head, which for example may take the form of a cavity, slot, groove, indent or aperture.

In one embodiment, the drug dispenser herein takes the form of an inhalation device and comprises:

(I) a housing;
(II) within said housing, an internal dispensing mechanism as described hereinbefore; and
(III) provided to the housing, a mouthpiece, capable of communication with the outlet.

The mouthpiece typically communicates with the outlet, which in embodiments takes the form of a manifold. Drug from an opened pocket of the one or more drug carriers may thus be channelled via the manifold to the mouthpiece. Suitable forms of manifold have been described in WO-A-2007/068900, supra.

In one particular embodiment, the inhalation device further comprises a 'mouthpiece cover drive' mechanism comprising:
(IV) in movable connection to the housing, a cover for said mouthpiece, said cover being movable from a first position, in which said mouthpiece is covered, to a second position, in which said mouthpiece is at least part-uncovered, wherein said cover is capable of coupling with said internal dispensing mechanism such that further movement of the cover from the second position to a third position results in actuation of the internal dispensing mechanism.

A 'mouthpiece cover drive' mechanism of this type has been described in WO-A-2007/068900, supra.

In this particular embodiment, the inhalation device comprises a cover for the mouthpiece, wherein the cover is movably connected to the housing. In embodiments, the cover is mounted to the housing by a suitable rotational mounting such as a pivot mounting.

The cover is movable from a first position, in which the mouthpiece is covered, to a second position, in which the mouthpiece is at least part-uncovered, in embodiments fully uncovered. Such movement is reversible and enables reversible covering and at least part-uncovering of the mouthpiece. Further, such reversible movement from the first to second position does not result in any actuation of the dispensing mechanism.

The mouthpiece cover is also capable of coupling with the internal dispensing mechanism such that further movement of the cover from the second position to a third position results in actuation of the dispensing mechanism. That is to say, on moving the cover from the second to the third position, the cover couples (e.g. directly or indirectly engages) the dispensing mechanism such as to result in actuation thereof.

In a variation of this particular embodiment, the indicator head of the indicator pin is arranged to selectively engage and lock the movable mouthpiece cover, thereby preventing further actuation of the internal dispensing mechanism. To facilitate this engagement and lock, the movable mouthpiece cover may be provided with a pin-receiving element sized and shaped for receipt of the indicator pin head, which for example may take the form of a cavity, slot, groove, indent or aperture. Such pin-receiving element typically locates at an inner surface of the mouthpiece cover.

It may be appreciated that it is preferable for the movable cover to be locked (by interaction with the indicator head of the indicator pin) into its first position, in which the mouthpiece is covered. In embodiments, the pin-receiving element of the mouthpiece cover is therefore positioned relative to the 'popped out' indicator pin head to lock the mouthpiece cover in its first (mouthpiece-covered) position.

In a subtle aspect, it may be appreciated that it is preferable also to prevent locking of the movable mouthpiece cover in either its second (mouthpiece-partly covered) or third (mouthpiece fully-uncovered) positions. To achieve this, the mouthpiece cover is in embodiments, provided on one edge with a ramp surface arranged such that interaction thereof with a 'popped out' indicator pin head (on moving the cover from third to second, or more typically from second to first positions) causes that pin head to be temporarily depressed. In embodiments, the indicator pin head remains depressed until the mouthpiece cover is in its first (mouthpiece-covered) position when the indicator pin is enabled to 'pop out' into locking engagement with the pin-receiving element of the mouthpiece cover.

In embodiments, the movement of the mouthpiece cover from first to second to third positions is by movement along a defined path. The path may for example be linear or arcuate (e.g. about a rotational axis).

In embodiments, the nature and direction of the path is defined by the form of the mounting of the mouthpiece cover to the housing. In one aspect, a track is defined within the housing for receipt of a track follower provided to the mouthpiece cover, and in following the track a suitable path is defined.

Alternatively, the mouthpiece cover is arranged for rotational movement about an axis. In embodiments, the mouthpiece cover interacts with a ratchet gear, which in turn interacts with a drive gear for drive of the internal dispensing mechanism. In embodiments, in the first position the ratchet gear is spaced from the drive gear and in the second position the ratchet gear engages the drive gear such that further movement thereof (e.g. to the third position) results in movement of the drive gear, and hence advancement of the dispensing mechanism.

In embodiments, the ratchet gear and/or drive gear is provided with an anti-return feature to prevent return (i.e. reverse) rotation thereof.

The drug dispenser may also be designed for nasal inhalation of a powdered drug and may therefore incorporate a nosepiece as an alternative to a mouthpiece. If the drug is in solid form, the dispenser may incorporate an exit channel for tablet release.

In embodiments, the drug dispenser comprises an actuation or dose counter for counting the number of actuations of the indexing lever or releases of dose from the cassette. The dose counter may count the number of doses left to be taken or the number of doses taken. In embodiments, said dose counter is electronic. Alternatively, said dose counter is mechanical.

One suitable actuation counter is described in Applicant's co-pending PCT patent application No. WO-A-2005/079727 (corresponding to U.S. Ser. No. 10/597,551), the disclosures of both of which applications are incorporated herein by reference. The actuation counter therein described comprises a first count wheel arranged to rotate about a first axis of rotation, the first count wheel including a set of primary drive teeth arranged annularly thereon for drivable rotation of the first count wheel about the first axis of rotation; and a second count wheel arranged to rotate about the same first axis of rotation. A kick wheel is arranged to rotate about a second axis of rotation offset from the first axis of rotation and provides for intermittent motion of the second count wheel.

The term drug carrier herein is used to define any suitable form of carrier for drug. In embodiments, the drug carrier is in the form of a strip or tape. In one preferred aspect, the drug carrier has a blister pack form, but it could also, for example, comprise a carrier onto which drug has been applied by any suitable process including printing, painting and vacuum occlusion.

In a preferred embodiment, the drug dispenser herein comprises a drug carrier having a plurality of pockets for containing drug wherein said pockets are essentially uniformly spaced along the length of and defined between two peelably separable sheets secured to each other. The drug carrier is generally in the form of an elongate, peelable blister strip.

In embodiments, the peelable blister strip comprises a base sheet in which blisters are formed to define pockets therein for containing distinct drug dose portions and a lid sheet which is hermetically sealed to the base sheet except in the region of the blisters in such a manner that the lid sheet and the base sheet can be peeled apart. The base and lid sheets are typically sealed to one another over their whole width except for the forward end portions where they are typically not sealed to one another at all. Thus, separate base and lid sheet forward end portions are presented at the end of the strip. The respective base and lid sheets are peelably separable from each other to (e.g. separately) release the contents of each pocket.

In one embodiment, the leading end of either the base or lid sheet or is looped to enable better receipt by the hub of the sheet driver herein.

In one embodiment, the drug carrier comprises a peelable blister strip in laminate form. In embodiments, the laminate comprises material selected from the group consisting of metal foil, organic polymeric material and paper. Suitable metal foils include aluminium or tin foil having a thickness of from 5 to 100 µm, preferably from 10 to 50 µm, such as 20 to 30 µm. Suitable organic polymeric materials include polyethylene, polypropylene, polyvinyl chloride and polyethylene terephthalate.

In embodiments, the lid sheet comprises at least the following successive layers: (a) paper; adhesively bonded to (b) polyester; adhesively bonded to (c) aluminium foil; that is coated with a heat seal lacquer for bonding to the base sheet. The thickness of each layer may be selected according to the desired properties but is typically of the order of from 5 to 200 micron, particularly from 10 to 50 micron.

Other suitable forms of lid sheet are described in WO-A-2007/038488, the disclosure of which application, and its US national phase equivalent, is incorporated herein by reference.

In embodiments, the base sheet comprises at least the following successive layers: (a) oriented polyamide (OPA); adhesively bonded to (b) aluminium foil; adhesively bonded to (c) a third layer comprising a polymeric material (e.g. polyvinyl chloride).

Various known techniques can be employed to join the lid and base sheet and hence to seal the blisters of the peelable blister strip. Such methods include adhesive bonding, hot metal bonding, hot metal welding, radio frequency welding, laser welding, ultrasonic welding and hot bar sealing. The lid sheet and base sheet of the peelable blister strip are particularly sealable by 'cold form' sealing methods, which are conducted at lower temperatures than conventional heat sealing methods. Such 'cold form' sealing methods are of particular utility where the drug or drug formulation for containment within the blister is heat sensitive (e.g. degrades or denatures on heating). Suitable 'cold form' sealing methods are conducted at a temperature in the range of 150-250° C., more preferably, 210-240° C.

The drug may comprise a capsule, pellet or tablet. Alternatively, the drug may be in powdered form. Preferably, when in powdered form the drug comprises a drug. Preferably the drug is selected from the group consisting of albuterol, salmeterol, fluticasone propionate and beclomethasone dipropionate and salts or solvates thereof and any combination thereof. Preferably said combination comprises salmeterol xinafoate and fluticasone propionate.

In embodiments, the powdered drug additionally comprises an excipient. In embodiments, said excipient is a sugar.

In another embodiment, the invention provides the use of a drug dispenser as described hereinbefore.

BRIEF DESCRIPTION OF THE DRAWINGS

The invention will now be described with reference to the accompanying drawings in which:

FIGS. 2a to 2m show perspective views of sequential steps of the assembly of a sheet driver or spool herein;

FIGS. 4a to 4j show perspective views of sequential steps of the assembly of the drug dispenser including incorporation therein of the sheet driver/spool;

FIGS. 5a to 5c show perspective views of a 'lock out' of the drug dispenser by the sheet driver/spool in a first 'failure' mode;

FIG. 8 is a partial side view of a shaft of a base of the sheet driver/spool showing another optional modification thereto.

DETAILED DESCRIPTION OF THE DRAWINGS

Figure 1:
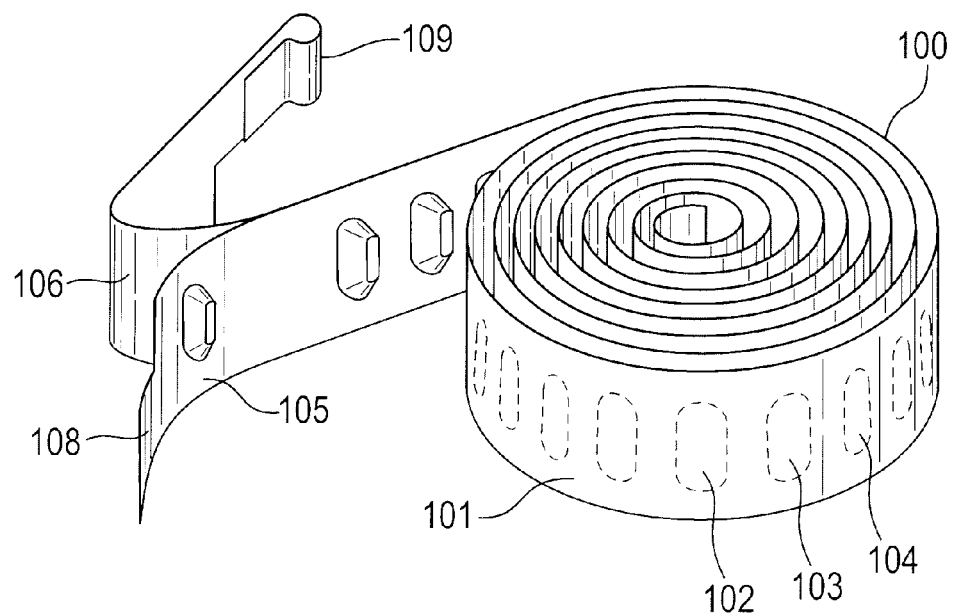
FIG. 1 shows a perspective view of a drug carrier or tape for use in a drug dispenser with a sheet driver or spool in accord with the present invention.

Referring now to the drawings in more detail, FIG. 1 shows a drug carrier 100 of the type disclosed in U.S. Pat. No. 5,860,419 previously incorporated herein by reference, and as used in the dry powder inhaler (DPI) marketed by Glaxo-SmithKline under the trademark DISKUS®.

The drug carrier 100 (or tape) comprises a flexible (rollable) strip 101 defining a plurality of pockets 102, 103, 104 each of which contains the same metered amount (e.g. a metered dose or dose portion) of a drug formulation that can be inhaled, in the form of powder. The strip comprises a base sheet 105 in which blisters are formed (e.g. by cold forming or deep drawing) to define the pockets 102, 103, 104 and a lid sheet 106 which is hermetically sealed to the base sheet in such a manner that the lid sheet 106 and the base sheet 105 can be peeled apart to thereby sequentially open the pockets 102, 103, 104. The sheets 105, 106 are sealed to one another over their whole width, except in the region of the blisters, and over their whole length, except for the leading end portions 108, 109. The leading end portion 109 of the lid sheet 106 is formed into a secured, closed loop for engagement with a hub of a sheet driver (or spool) herein, as will be described in more detail hereinafter.

The lid 106 and base 105 sheets are each preferably formed of a plastics/aluminium laminate and are preferably adhered to one another by heat sealing. The materials used for the lid 106 and base 105 sheets may be as used in the DISKUS® dry powder inhaler (e.g. for the ADVAIR® product) and/or as disclosed in US-A-5860419, previously incorporated herein by reference. Alternatively, the materials may be as disclosed in WO-A-2007/038488, previously incorporated herein by reference.

The strip 101 is shown as having uniformly spaced-apart, uniform volume, elongate pockets 102, 103, 104 that run transversely with respect to the length of the strip 101. This is convenient in that it enables a large number of pockets 102, 103, 104, and hence metered amounts of drug powder formulation, to be provided in a given strip length. The strip 101 may, for example, be provided with sixty or one hundred pockets but it will be understood that the strip 101 may have any suitable number of pockets.

FIGS. 2a to 2m show details of sequential steps in the assembly of a sheet driver (or spool) in accordance with the present invention for use with the drug carrier 100. Such assembly would typically be carried out on an automated (computer-controlled) assembly line.

The sheet driver is of the type disclosed in WO-A-2006/018261 and U.S. Ser. No. 11/573,656, previously incorporated herein by reference. In respect of each of the FIGURES, only the most relevant parts for that FIGURE are labelled.

Referring initially to FIGS. 2a to 2e, there are shown sequential steps in the assembly of a base and indicator pin sub-assembly of the sheet driver.

In more detail, and referring initially to FIG. 2a, the sub-assembly comprises a circular (wheel) form base 220 having a geared (toothed) drive surface 225 provided to its circumferential rim 222 and an integral, upwardly extending hollow shaft 230 provided at, and centred on, the rotational axis of the base 220.

The upper end 231 of the shaft 230 defines an entry to a blind shaft cavity 232, which extends lengthways along the shaft 232 and has a circular cross-section. The wall of the shaft 230 is provided with a slot 233, which extends lengthways along the shaft 230 and has a lock-profile cut-away portion 234 at its bottom. The wall of the shaft 230 is further provided with a circumferential indent 235, the purpose of which will become clear from the later description.

The sub-assembly further comprises a compression spring 238 which is arranged for receipt at the bottom of the shaft cavity 232. In this embodiment, the compression spring 238 is made from stainless steel, but other suitable metal or plastics materials for fabricating a compression spring could be used, as known in the art.

Figure 2B:
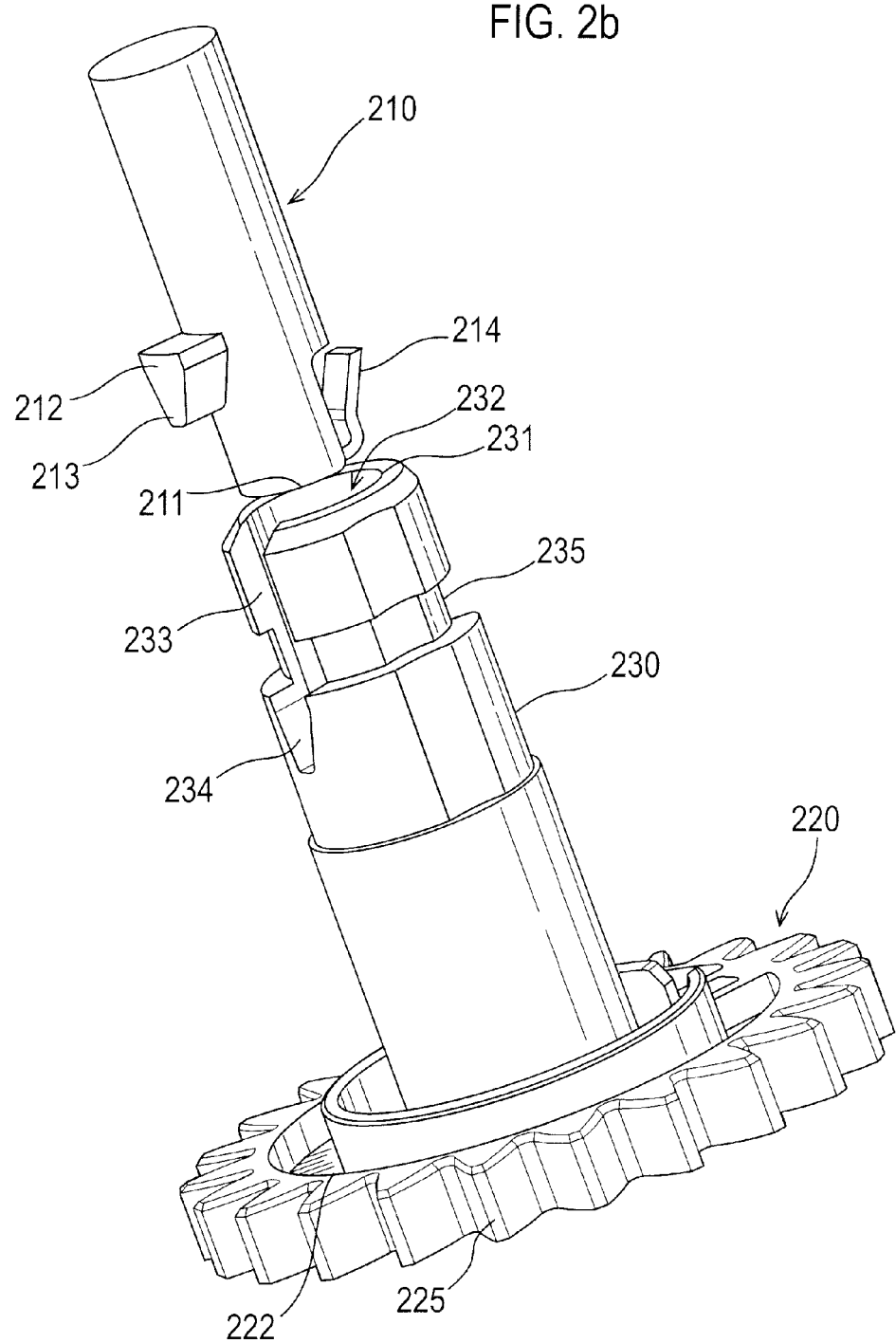
Figure 2C:
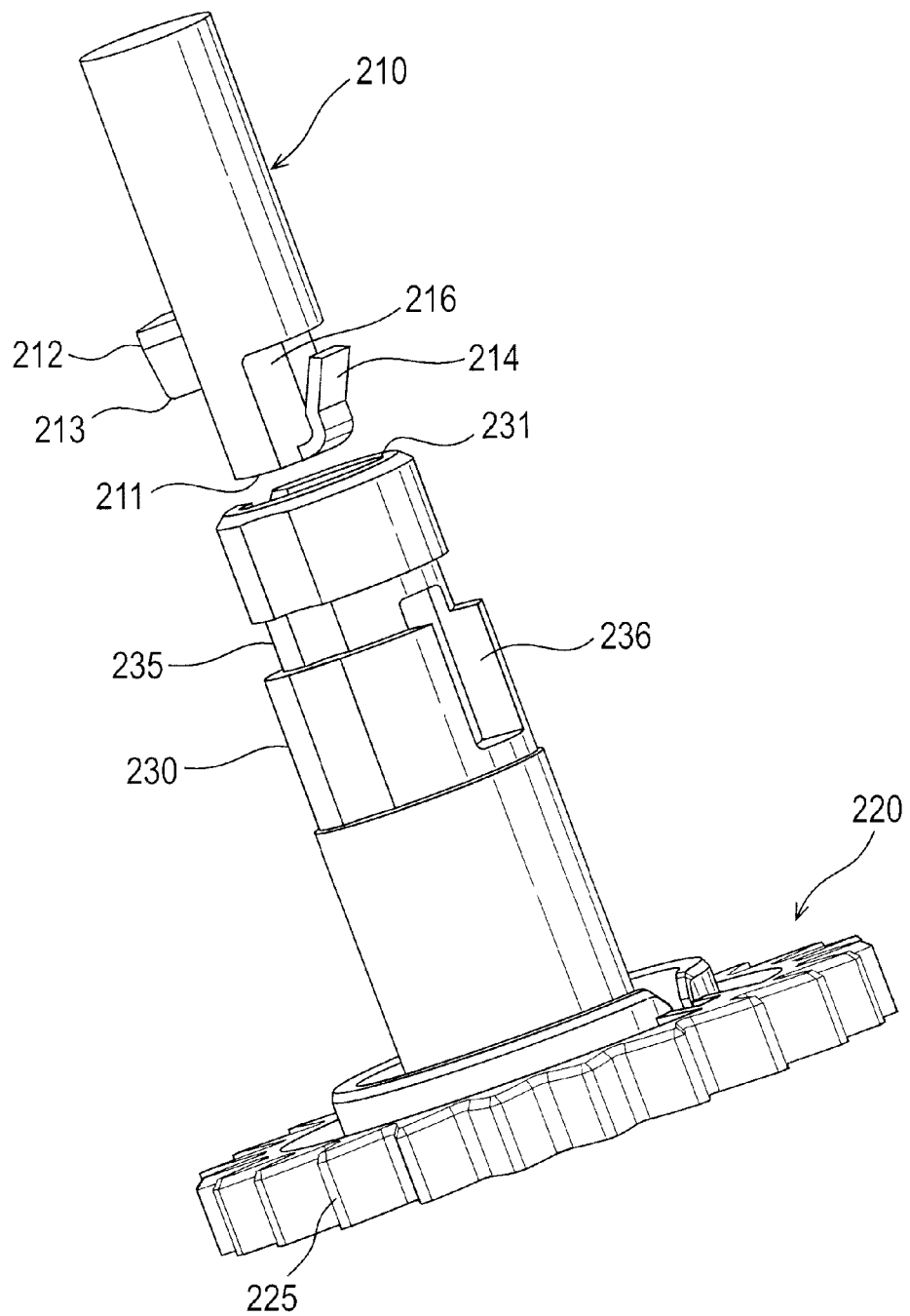

Referring now to FIGS. 2b and 2c, once the compression spring 238 is received within the shaft cavity 232, an indicator pin 210 of generally circular cross-section is then brought alongside the shaft 230 such that the bottom 211 of the pin 210 lines up with the axial shaft cavity 232. Further, a projecting side member 212 of the indicator pin 210 is lined up with the axial slot 233 and a projecting spring alignment feature 214, in the form of a resilient tongue, which locates within a cut-away section 216 at the bottom 211 of the indicator pin 210, is lined up with an axial alignment feature-receiving cavity or slot 236 (see FIGS. 2c and 2d) of the shaft 230, which shaft cavity 236 forms a side opening to the shaft cavity 232. It will be noted that the projecting side member 212 of the pin 210 has at its bottom a key-shaped profile 213 that mirrors (complements) the lock-shaped profile 234 of the bottom of the shaft slot 233.

The pin side member 212 and the pin spring alignment feature 214 are on diametrically opposite sides of the pin 210. Moreover, the base shaft slots 233, 236 are on diametrically opposed sides of the base shaft 230. In addition, a retainer slot 224 provided on the base 220 lies in the same plane (a diametrical plane of the base) as the base shaft slots 233, 236.

Referring now to FIGS. 2d and 2e, the indicator pin 210 is slid within the shaft cavity 232. As may be seen in FIG. 2d, the spring alignment feature 214 thereof latches onto the alignment-feature receiving cavity 236 of the shaft 230, thereby holding the pin 210 captive within the shaft 232 against the biasing force of the spring 238, since the spring 238 pushes the pin 210 upwards (i.e. outwards or away from the base 220). As may be seen in FIG. 2e, the key-shaped bottom 213 of the projecting side member 212 of the pin 210 is lined up with the lock-shaped bottom 234 of the slot, but these are not yet in lock-and-key engagement. The pin 210 is therefore in a 'popped out' (but retained) position relative to the shaft 230. As will be appreciated, the pin 210 will rotate in unison with the base 220.

This completes the sub-assembly of the sheet driver.

In a modification of the sheet driver sub-assembly, to be described with regard to FIG. 8, the shaft cavity 236 is dispensed with and the axial profile of the shaft slot 233 is modified so as to form a snap-lock for the projecting side member 212 of the pin 210 therein. As shown in FIG. 8, the width of the shaft slot 233 at its upper end 291, above the indent 235, is narrowed. When the indicator pin 210 is slid into the shaft cavity 232, the tapered lower end of the projecting side member 212 prises apart (widens) the narrowed upper end 291 of the shaft slot 233 to allow the projecting side member 212 to slid into the shaft slot 233. Once the projecting side member 212 has passed the narrowed upper end 291, the inherent resiliency in the shaft 230 causes the narrowed upper end 291 to snap behind the projecting side member 212 of the pin 210, and therefore hold the pin captive with the shaft 230. The spring alignment feature 214 of the pin 210 reacts on the inner surface of the shaft cavity 232 to bias the pin 210 towards the shaft slot 233.

Referring now to FIGS. 2f to 2m, there are shown sequential steps in the further assembly of the sheet driver, whereby a torsion spring 240 and a hub 250 are sequentially added to the sub-assembly of FIG. 2e.

Figure 2F:
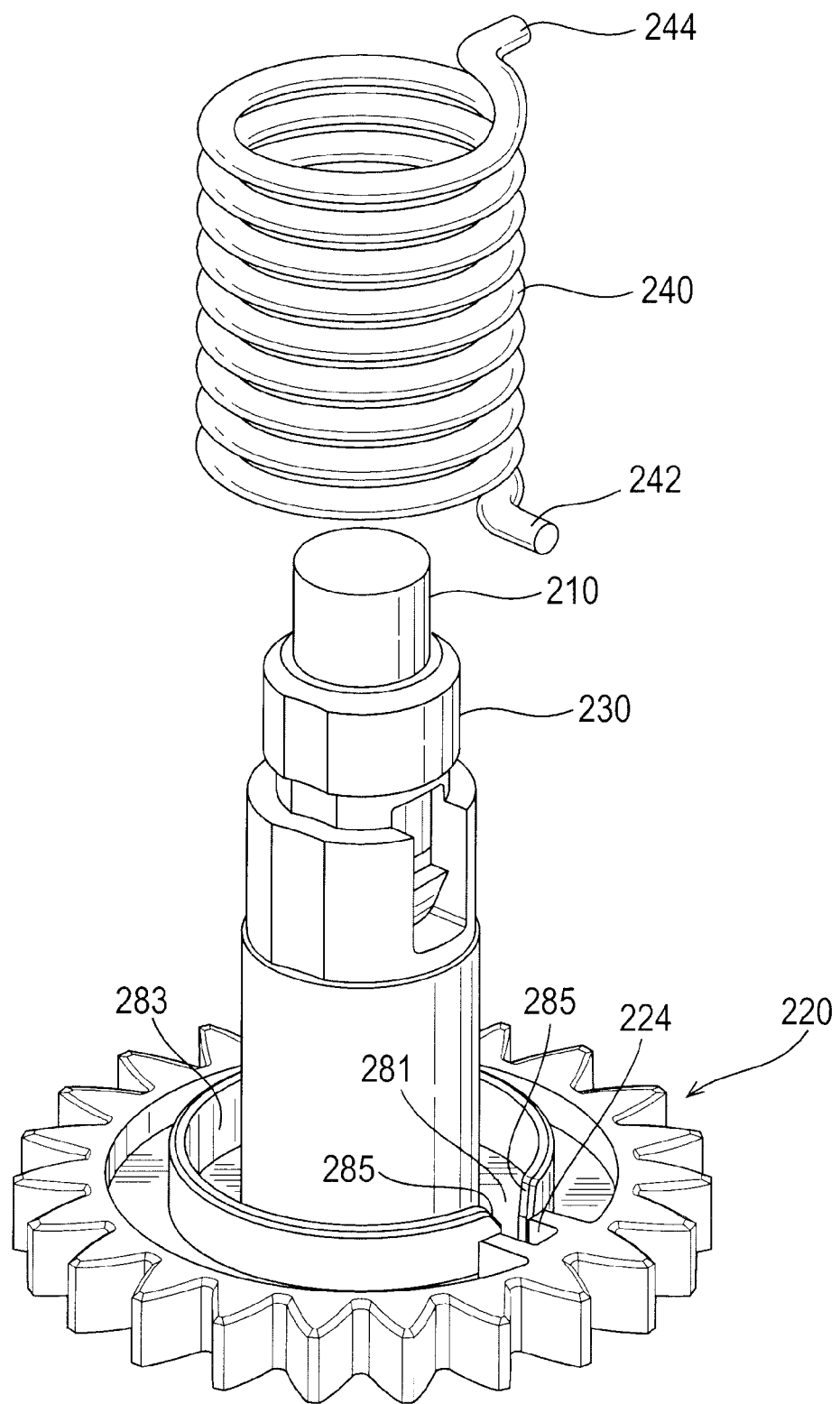
Figure 2G:
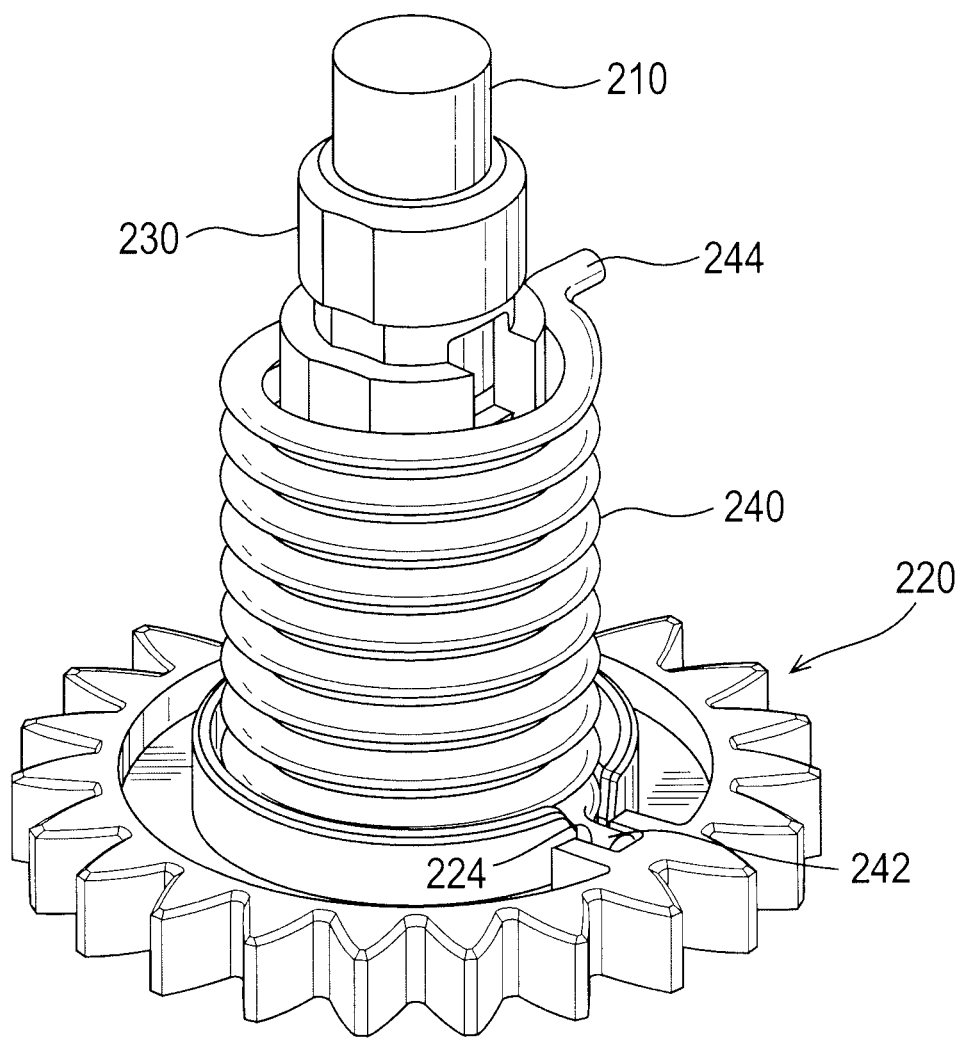

As shown at FIGS. 2f and 2g, the lower and upper ends of the torsion spring 240 define lower 242 and upper 244 spring legs. In these FIGURES, the spring legs 242, 244 are shown as being angled at approximately a right-angle to one another in the return or unloaded state. However, other angles could be adopted, for instance less than 90 degrees, for example in the range of 15 to 45 degrees. In addition, the number of turns in the spring 240 could be varied from that shown (likewise for compression spring 238).

The torsion spring 240 is lowered onto the shaft 230 such that the lower spring leg 242 engages in a spring leg retainer slot 224 of the base 220. To help guide the lower spring leg 242 into the retainer slot 224 during the assembly process, the spring leg 242 also engages in a cut-out 281 in an inwardly-disposed, spring retaining wall 283 which is upstanding on the base 220, which cut-out 281 is aligned with the retainer slot 224 and includes tapered lead-in surfaces 285 for guiding the lower spring leg 242 into the cut-out 281 and the retainer slot 224.

In FIGS. 2f and 2g the indicator pin 210 is in its 'non-popped out' position, where the pin 210 is located inwardly in the shaft cavity 232 and compresses the compression spring 238 at the base of the shaft cavity 232. This is purely to illustrate this pin position, as these assembly steps would typically be carried out with the pin 210 in its 'popped out' position, as shown in FIG. 2h.

In this embodiment, the torsion spring 240 is made from stainless steel, but other suitable metal or plastics materials for fabricating a torsion spring could be used, as known in the art.

Referring now to FIG. 2h, the hub 250 is positioned such that it may be lowered over the shaft 230 such that it sits over the torsion spring 240. The hub 250 may be seen to be provided with an upwardly standing post or hook 258 arranged for receipt of the loop formed at the leading end portion 109 of the lid sheet 106 of the drug carrier 100 of FIG. 1, as will be described in more detail hereinafter.

FIG. 2i shows details of the top surface 251 of the hub 250, in particular a central hub aperture 254 defined by a hub aperture rim 256 and having a missing rim segment or notch 257 which has a complementary cross-section to the projecting side member 212 of the indicator pin 210.

Figure 2J:
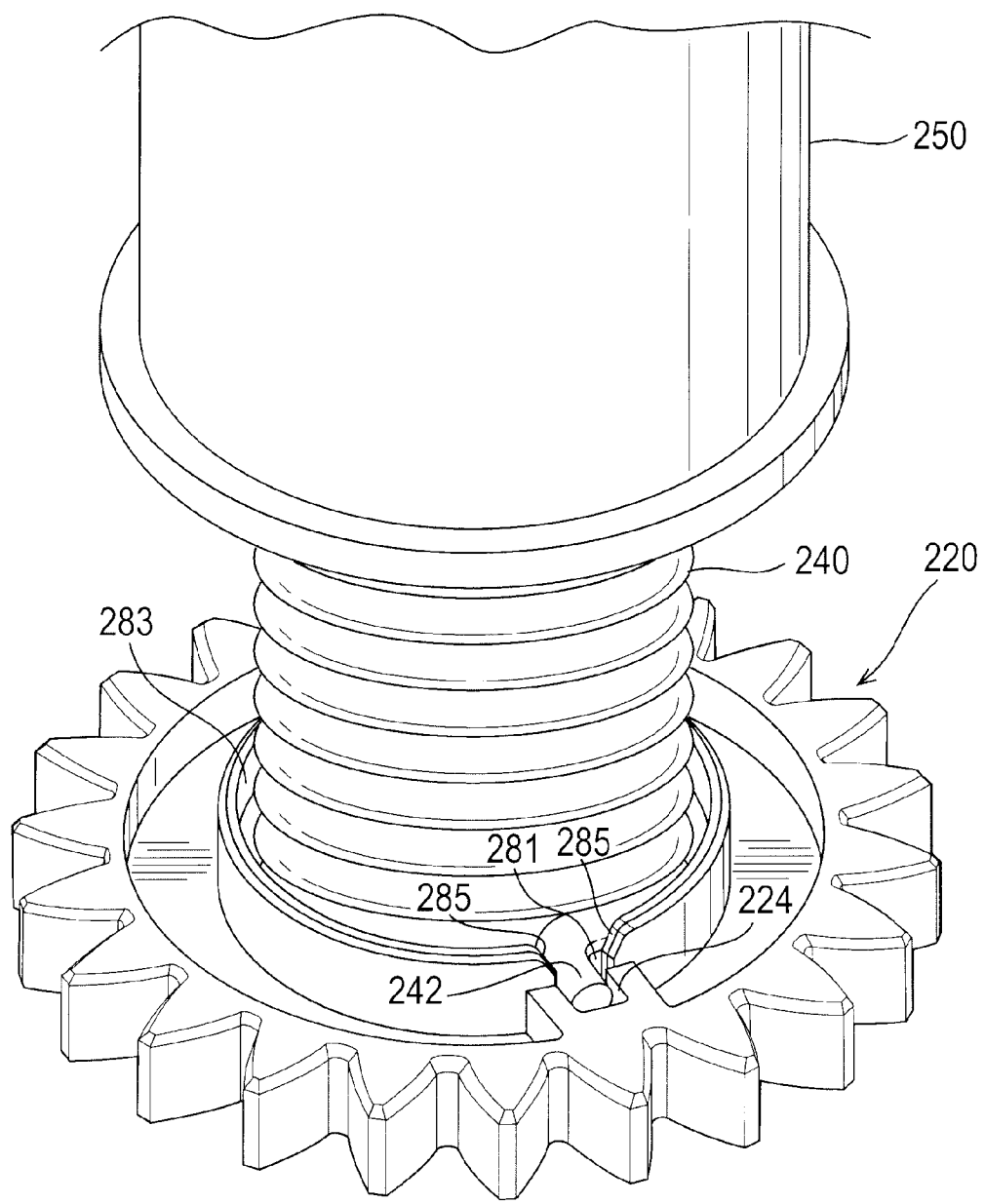
Figure 2K:
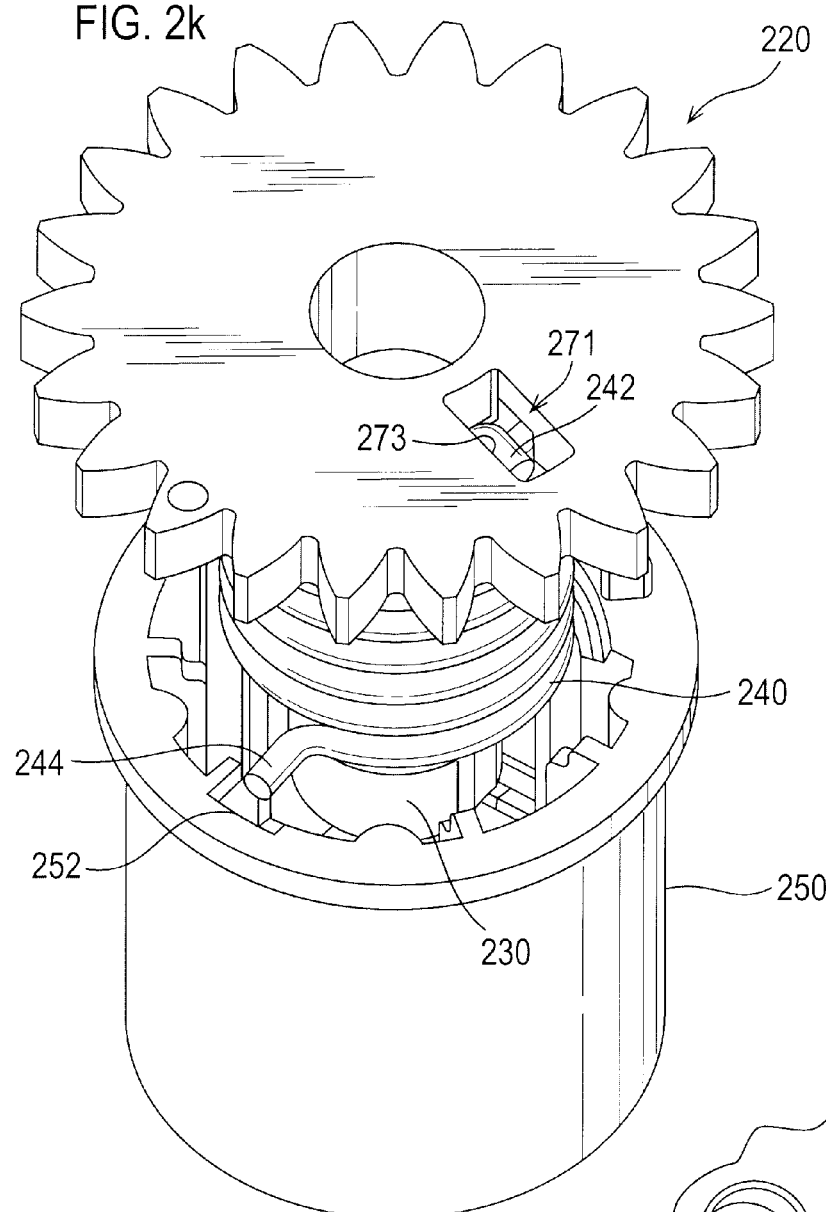

Referring now to FIGS. 2j and 2k, the hub 250 is shown lowered over the shaft 230. It may be seen that upper spring leg 244 of torsion spring 240 is received by an axial spring leg retainer slot 252 provided to the inner circumferential surface of the hub 250. The hub retainer slot 252 may also have a lead-in surface, such as the lead-in surfaces 285 described above for the cut-out 281.

FIG. 2k gives an underneath view of inter alia the gear wheel base 220 of the sheet driver, from which it will understood that the retainer slot 224 (and the cut-out 281) is in registration with an aperture through the base 220 so that the lower spring leg 242 of the torsion spring 240 is visible from underneath the sheet driver. This enables inspection of the sheet driver during or after its assembly to check that the lower spring leg 242 is in the retainer slot 224, for instance using automated (computer-controlled) vision inspection equipment on the assembly line.

Figure 7:
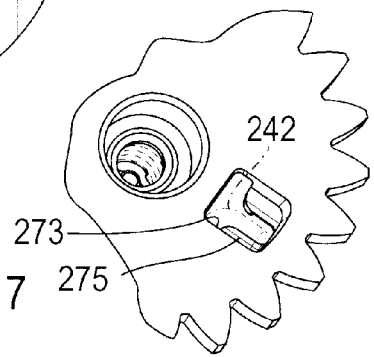
FIG. 7 is an underneath, perspective view of the sheet driver/spool showing an optional modification thereto.

As will further be understood from FIG. 2k, the lower spring leg 271 will engage against a side wall 273 of the aperture 271 when the torsion spring 240 is loaded in assembly steps to be described with reference to FIGS. 2l, 2m, 3a and 3b. Bearing this in mind, FIG. 7 shows a modification of the base 220 in which the aperture 273 is profiled to create an undercut 275 therein. In use, when the lower spring leg 242 is biased against the aperture side wall 273, the lower spring leg 242 is disposed underneath the undercut 275, or more particularly, in this embodiment, an undercut section disposed on the same side of the aperture 271 as the side wall 273 (another undercut section being disposed on the other side of the aperture 271). This arrangement protects the lower spring leg 242 from escaping from the retainer slot 224, for instance in the event of impact (e.g. drop) forces that may be experienced by the sheet driver in assembly or (mis)use.

Referring now to FIG. 2l, as indicated by the arrowhead, the hub 250 is rotated in an anti-clockwise direction by a defined rotation (in this case about 105°) relative to the base 220. It will be appreciated that because the spring legs 242, 244 of the torsion spring 240 attach respectively to the base 220 and hub 250, such rotation results in tensing or loading of the torsion spring 240. The extent of defined rotation is selected such as to align a stepped wall 255 of the underside of the hub 250 with an edge of the wall 223 that forms part of the retainer slot 224 for the lower spring leg 242.

Figure 2M:
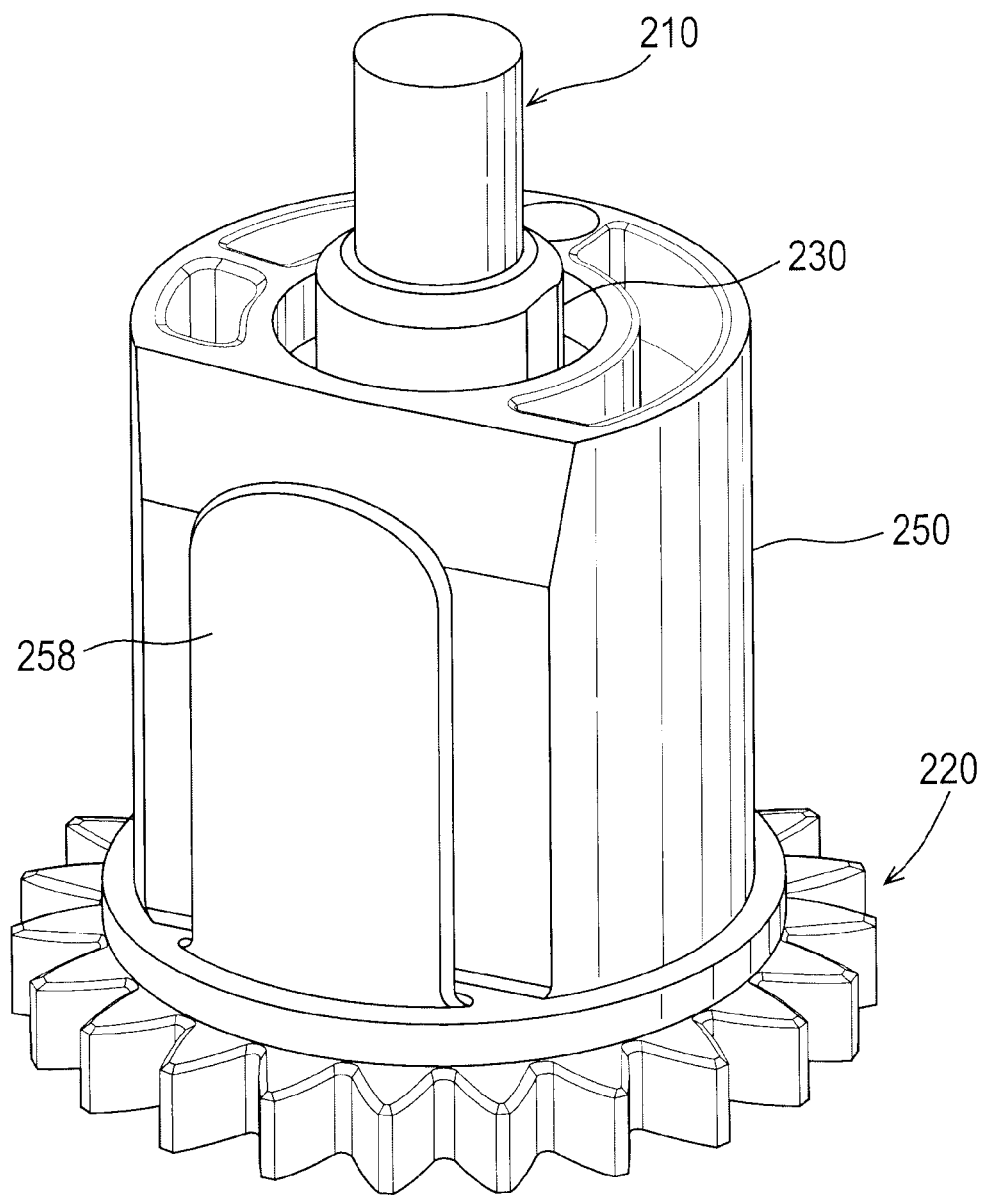

As shown in FIG. 2m, the hub 250 is then pressed home (i.e. downwards towards the base 220) such that (i) the hub aperture rim 256 snap-fits within the circumferential indent 235 of the shaft 230 of the base 220 to retain the hub 250 to the base 220, and (ii) the hub stepped wall 255 engages behind the base wall 223 to prevent the biasing/unloading force of the torsion spring 240 rotating the hub clockwise relative to the base 220. This is the "assembled state" of the sheet driver.

Figure 3A:
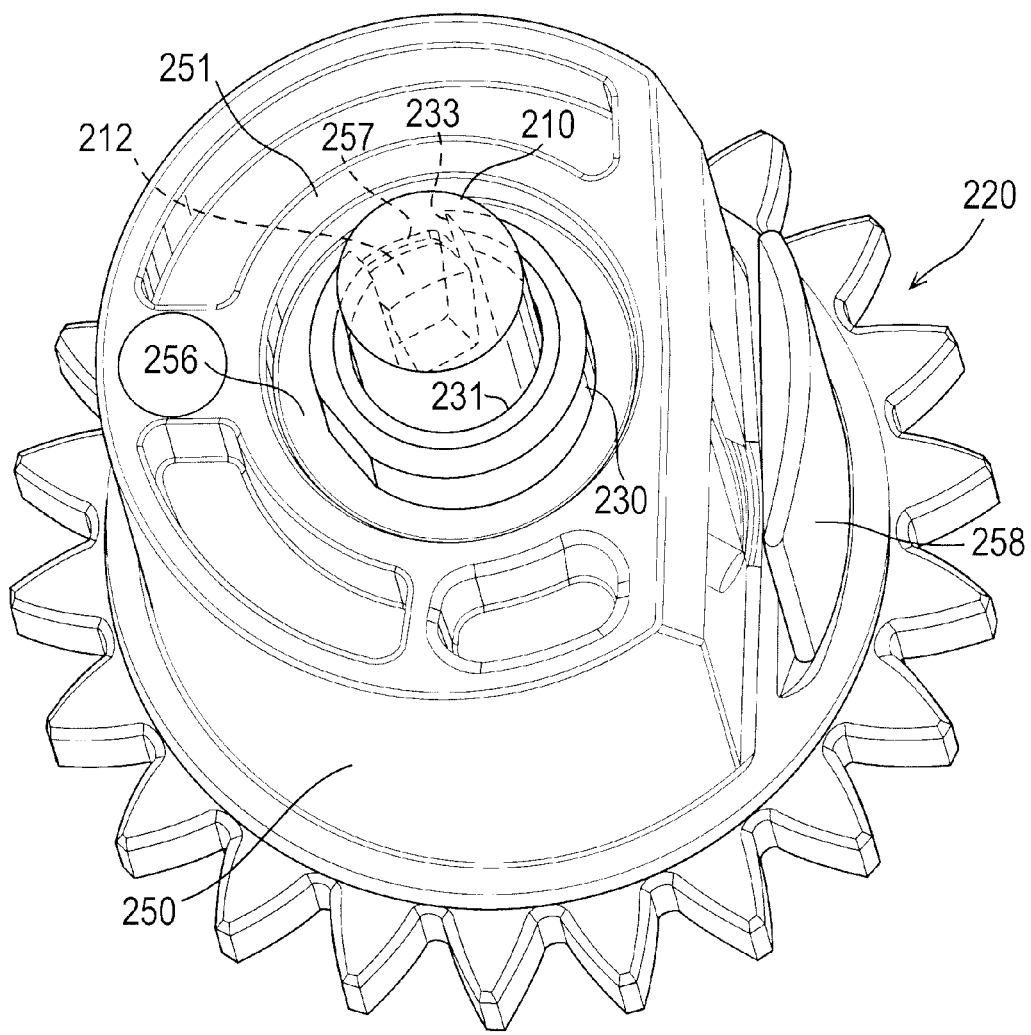
FIGS. 3a to 3c show perspective views of the sheet driver/spool in respectively its unattached or assembled state; in its state when attached to an unbroken lid sheet of the drug carrier/tape within a drug dispenser; and in its state when attached to a broken lid sheet of the drug carrier/tape within the drug dispenser.

In the assembled state, the pin 210 is still in its 'popped out' state since the projecting side member 212 of the pin 210 aligns with, and protrudes through, the complementary missing segment 257 of the hub aperture rim 256 (see also FIG. 3a). The upper end 231 of the shaft 230 protrudes through the central aperture 254 of the upper end 251 of the hub 250 more than would be the case if the pin was in its 'non-popped out' position. Moreover, the hub 250 cannot rotate on the base 220 in the assembled state due to the projecting side member 212 of the pin 210 protruding through (i.e. bridging) the missing rim segment 257.

The relative angular orientation (rotary position) of the hub 250 on the base 220 in the assembled state is the only relative orientation where the indicator pin 210 is able to be in its 'popped out' position, since it is the only orientation where the projecting side member 212 of the pin 210 and the missing rim segment 257 of the hub 250 align.

In this embodiment, the base 220, indicator pin 210 and hub 250 are injection moulded from acetal, but other engineering plastics materials and fabrication techniques could be used instead.

As stated, the torsion spring 240 cannot unwind from its tensed state as a result of the interaction of the stepped wall 255 of the underside of the hub 250 with the edge of the wall 223 that forms part of the retainer slot 224 for the lower spring leg 242 (see FIG. 2l). The tension that is present in the torsion spring 240 at this time (i.e. before attachment of any lid sheet) corresponds to the 'start' tension present in the torsion spring 240. The sheet driver is now ready for use with the drug carrier 100 in a suitable drug dispenser.

Figure 3B:
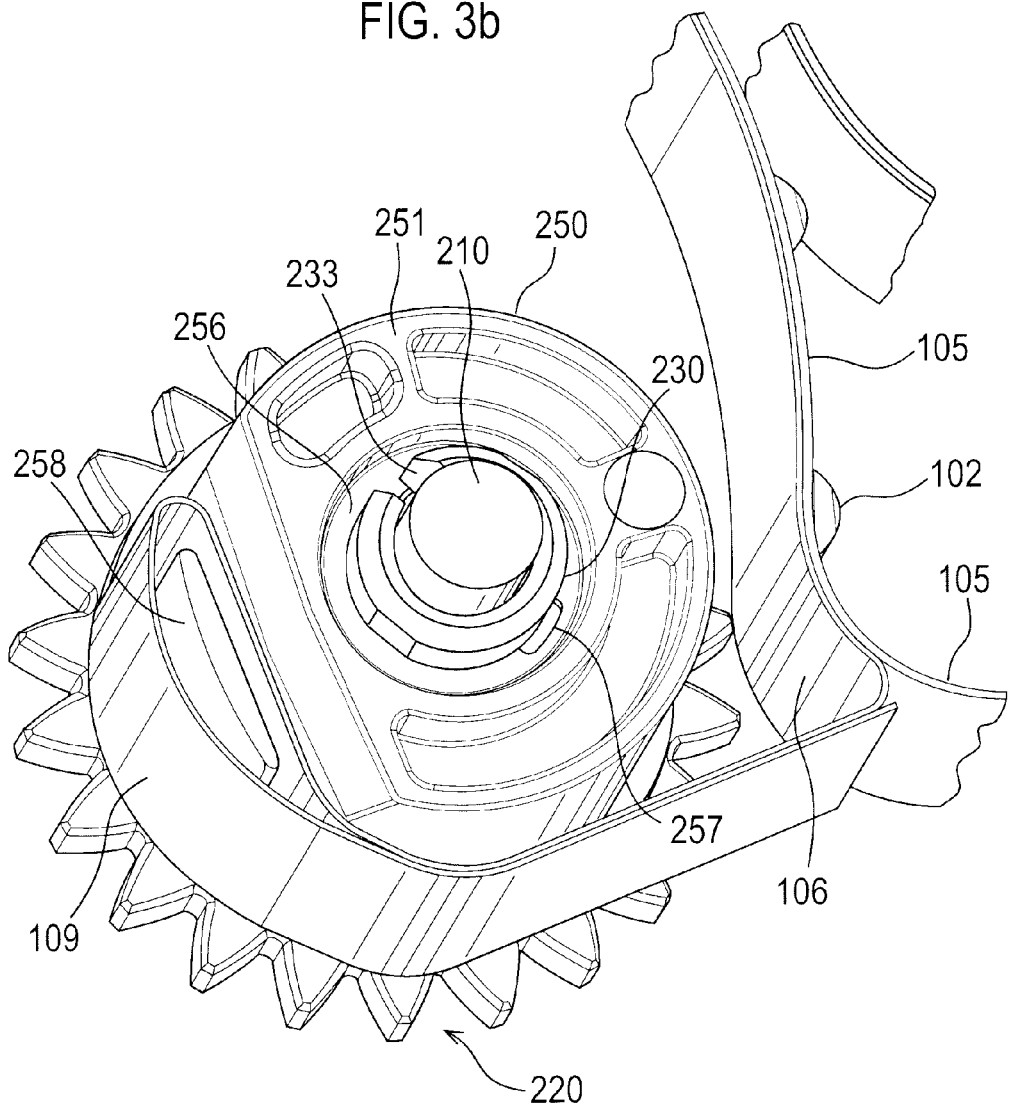
Figure 3C:
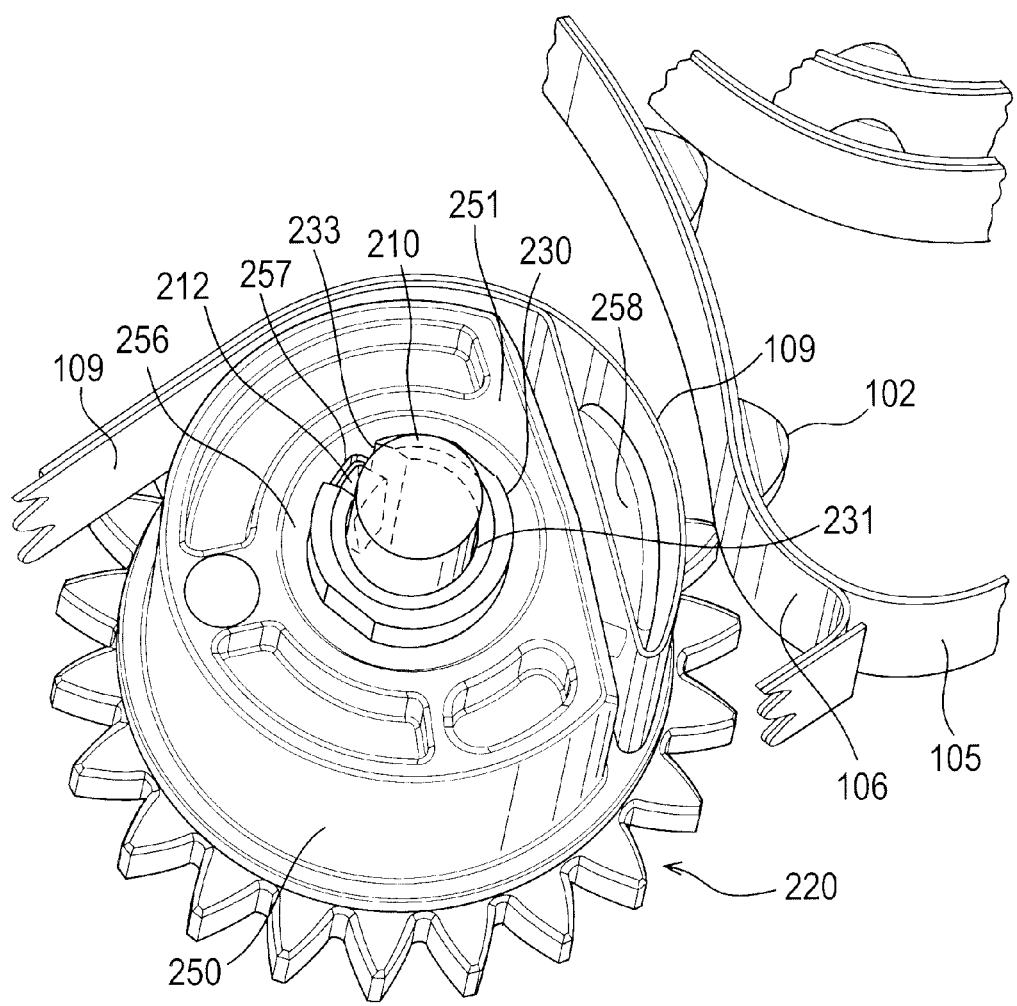

As will be described, the indicator pin 210 is adapted for indicating loss of tension arising from a 'failure' (e.g. as a result of breakage) of the lid sheet 106 of the drug carrier 100 being driven thereby within a drug dispenser device. FIGS. 3a to 3c illustrate details of working of this indicator pin 210.

In FIG. 3a, there is shown a perspective plan view of the sheet driver in the assembled state, prior to attachment of the lid sheet 106 of the drug carrier 100 of FIG. 1 thereto.

In FIG. 3b, the sheet driver is schematically shown mounted for rotation to the body of a drug dispenser device (refer also to FIGS. 4a to 4j). The hub 250 is rotated anti-clockwise (as viewed), away from its assembled position (where the hub step 255 engages the base wall 223 in the assembled state of the sheet driver), to further load the torsion spring 240. The looped end 109 of the lid sheet 106 of the elongate blister pack 100 is attached to the upstanding hook 258 of the hub 250 and the lid sheet 106 holds the hub 250 against rotating clockwise (as viewed) back to its assembled position of FIG. 3a under the influence of the torsion spring bias. This will be referred to as the "loaded position" of the hub 250 on the base 220. The lid sheet 106 counteracts the torsion spring 240 since the lid sheet 106 is held fast by other features of the dispensing mechanism, and only releases (indexes) enough of the drug carrier 100 on each actuation to open the next unopened pocket 102, 103, 104 in the series.

Of course, to enable the anti-clockwise rotation of the hub 250 on the base 220 to its loaded position, the indicator pin 210 is firstly pushed inwards to its 'non-popped out' position (i.e. towards the base 220) such that the projecting side member 212 is disposed under the hub aperture rim 256. The hub 250 retains the indicator pin 210 in the 'non-popped out' position except when in the assembled position because the lower surface of the hub aperture rim 256 acts on the projecting side member 212 to prevent the pin 210 moving upwards (i.e. under the biasing action of the compression spring 238) to its 'popped out' position.

The hub 250 and hub aperture rim 256 are kept in this 'pin-retaining' state because the pulling action of the lid sheet 106 acts such as to counteract the bias of the torsion spring 240 which biases the torsion hub 240 to rotate clockwise (as viewed in FIG. 3b) from its loaded position back to its assembled position.

In FIG. 3b the lid sheet 106 is unbroken and thus the sheet driver may be used to rotate clockwise (as viewed) to wind on the lid sheet 106 of the drug carrier 100 to open the next unopened pocket 102, 103, 104 of the drug carrier 100 in regular fashion by patient actuation of the drug dispenser, of which more details will follow shortly hereinafter.

In FIG. 3c, the lid sheet 106 (in this extreme case, the looped end portion 109) is shown as having torn or severed (in this case, prior to any drug carrier 100 advancement), thereby disabling any effective sheet driving action of the sheet driver within the drug dispenser. This disablement would be the same whenever or wherever the lid sheet 106 might tear or sever, e.g. after some or nearly all of the lid sheet 106 is wound up on the hub 250 to open some or nearly all of the pockets 102, 103, 104. It is important to signal any such 'failure' or 'fault' to the user of the drug dispenser device. The (fault) indicator pin 210 of the sheet driver allows for this.

As shown in FIG. 3c, if the lid sheet 106 breaks, the broken lid sheet 106 no longer applies any 'sheet pulling force' to the hub 250 of the sheet driver to counteract the clockwise (as viewed) biasing force of the torsion spring 240. The hub 250 thus rotates clockwise on the base 220 from its loaded position back to its assembled position as a result of the torsional force applied by the now-unconstrained torsion spring 240. In other words, the hub 250 rotates clockwise until the hub step 255 engages the base wall 223. Recalling that in the assembled position of the hub 250 on the base 220 the missing segment 257 in the hub aperture rim 256 aligns with the projecting side member 212 of the pin 210, it will be appreciated that the compression spring 238 now also pushes the pin 210 to its 'popped out' position so that the upper end 231 of the shaft 230 protrudes farther out of the central aperture 254 defined by the hub aperture rim 256 of the upper end 251 of the hub 250.

Accordingly, breakage (or other failure or fault) of the lid sheet 106 is signalled by the indicator pin 210 adopting its 'popped out' state (which it otherwise adopts only during assembly of the sheet driver, and before any effective attachment of the lid sheet 106). In accord with the present invention, this 'popping out' of the indicator pin 210 may either be employed within a drug dispenser to provide a visual indication to the user of a 'failure' of the lid sheet 106, and hence the drug carrier advancement mechanism. Or alternatively, the 'popped out' pin 210 may engage with an element of the drug dispenser mechanism to place the dispenser into a 'locked out' state. To better describe these aspects, further description is now provided of incorporation of the sheet driver into a suitable drug dispenser.

Thus, FIGS. 4a to 4j show perspective views of sequential steps in the assembly of a drug dispenser which is a manually-operable, hand-held dry powder inhaler (DPI), and of the type disclosed in WO-A-2007/068900, previously incorporated herein by reference. In more detail, drive unit 260 is arranged for use in a drug dispenser for use with plural peelable drug carriers 200a, 200b (tapes), each as shown in FIG. 1 (see FIG. 4f).

Figure 4A:
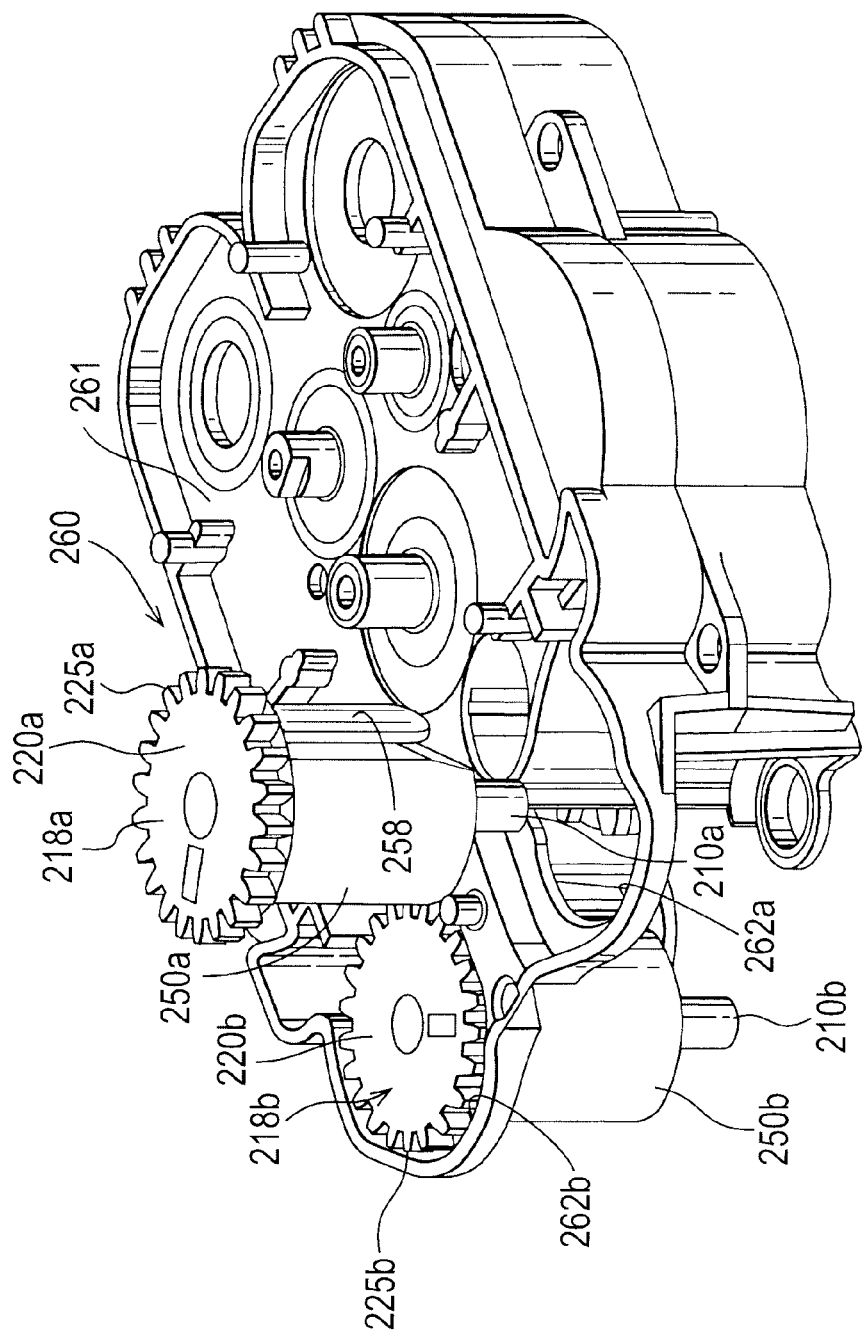

Referring to FIG. 4a, drive unit 260 is arranged for receipt of first and second sheet drivers 218a, 218b in accordance with the present invention such that the hubs 250a, 250b thereof extend through apertures 262a, 262b provided to the base 261 of the drive unit 260 and the indicator pins thereof 210a, 210b face downwards. The bases 220a, 220b of the drivers 218a, 218b protrude upwards from the apertures 262a, 262b such that the respective hubs 250a, 250b are rotatably drivable by rotary drive motion of the geared drive surfaces 225a, 225b of the respective bases 220a, 220b.

In this instance, the first sheet driver 218a is as described above for FIGS. 2 and 3, it winding on the associated drug carrier 200a by clockwise rotation (when viewed from above the hub 250a, as in FIGS. 3b and 3c).

However, the second sheet driver 218b is to wind on the associated drug carrier 200b by anti-clockwise rotation (when viewed from above the hub 250b); i.e. in the opposite sense to the first sheet driver 218a. The second sheet driver 218b therefore corresponds to the first sheet driver 218a of FIGS. 2 and 3 other than that the hub 250 for the second sheet driver 218b has its missing rim segment at a different position, namely as shown at 257' in FIG. 2i. The torsion spring 240 is also of a different biasing sense than that used for the first sheet driver 218a.

The second sheet driver 218b is brought to its assembled state, with the torsion spring provided with its start tension, by clockwise rotation of the hub 250b on the base 220b so that the hub step engages the opposite side wall of the lower spring leg retainer slot as in the first sheet driver 218a (the "assembled position" for the hub 250b of the second sheet driver 218b).

The hub 250b is then brought to its loaded position by pushing the indicator pin 210b downwards to its 'non-popped out' position and then providing further clockwise rotation of the hub 250b on the base 220b before attaching the loop end 209b of the respective lid sheet 206b to the hub hook 258b. If the lid sheet 206b 'fails', the anti-clockwise bias in the torsion spring 240 drives the hub 250b anti-clockwise back to its assembled position, whereupon the indicator pin 210b then moves to its 'popped out' position.

Another subtle difference is that the lower spring leg of the torsion spring in the second sheet driver 218b bears against the other side wall of the base aperture (271, FIG. 2k) than in the first sheet driver 218a. This explains the other section of the undercut 275 in the base aperture 271 in FIG. 7; in other words, the other undercut section is for when the base 220 is used for the second sheet driver 218b, where the lower spring leg bears against the other wall of the base aperture 271.

Referring to FIG. 4b, the geared drive surfaces 225a, 225b of the respective bases 220a, 220b may be seen to interact with complex gear train 265 provided to the base 261 of the drive unit 260. The gear train 265, and hence rotation of each respective base 220a, 220b is ultimately drivable by primary index gear 270, which interacts with ratchet unit 272, one purpose of which is to prevent reverse rotation of the primary index gear 270. It will be appreciated that primary index gear 270 and associated ratchet unit 272 are co-axially mounted about an axis that approximately corresponds to the central point of the drive unit base 261. In this embodiment, the primary ratcheted gear 270, 272 is itself driven by a movable mouthpiece cover 286, which is also mounted co-axially therewith and which will be described later with particular reference to FIGS. 4i and 4j.

Referring now to FIG. 4c, a protective retainer plate 259 has been provided to the drive unit 260 to protect the component parts thereof. Primary index gear 270 with associated ratchet unit 272 protrudes from the retainer plate. Referring now to FIG. 4d, a first shell housing part 282 has been applied. The first shell housing part 282 defines a curved slot form aperture 283, which allows access to the primary ratcheted gear 270, 272 and which, as will become clear from the later description, is arranged for receipt of first drive arm 274a of movable mouthpiece cover 286.

Figure 4E:
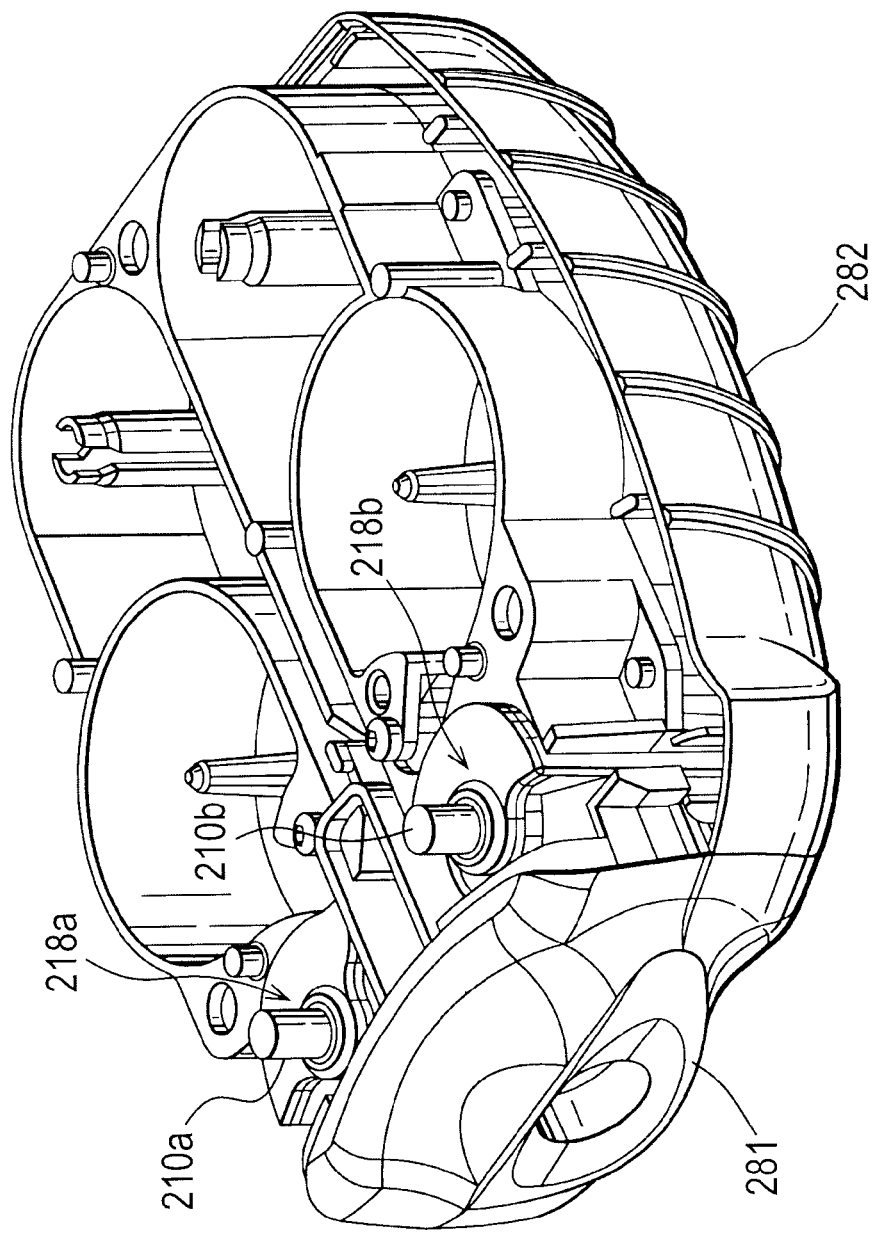

FIG. 4e shows the assembly unit of FIG. 4d, but rotated through 180° so that it is sitting on the first shell housing part 282 and with mouthpiece 281 now applied thereto. The first and second sheet drivers 218a, 218b may be seen, now with their indicator pins 210a, 210b extending upwards, in the 'popped out' position. The unit is now ready to receive either one or two drug carriers 200a, 200b and this receipt thereof is now shown at FIG. 4f.

Figure 4F:
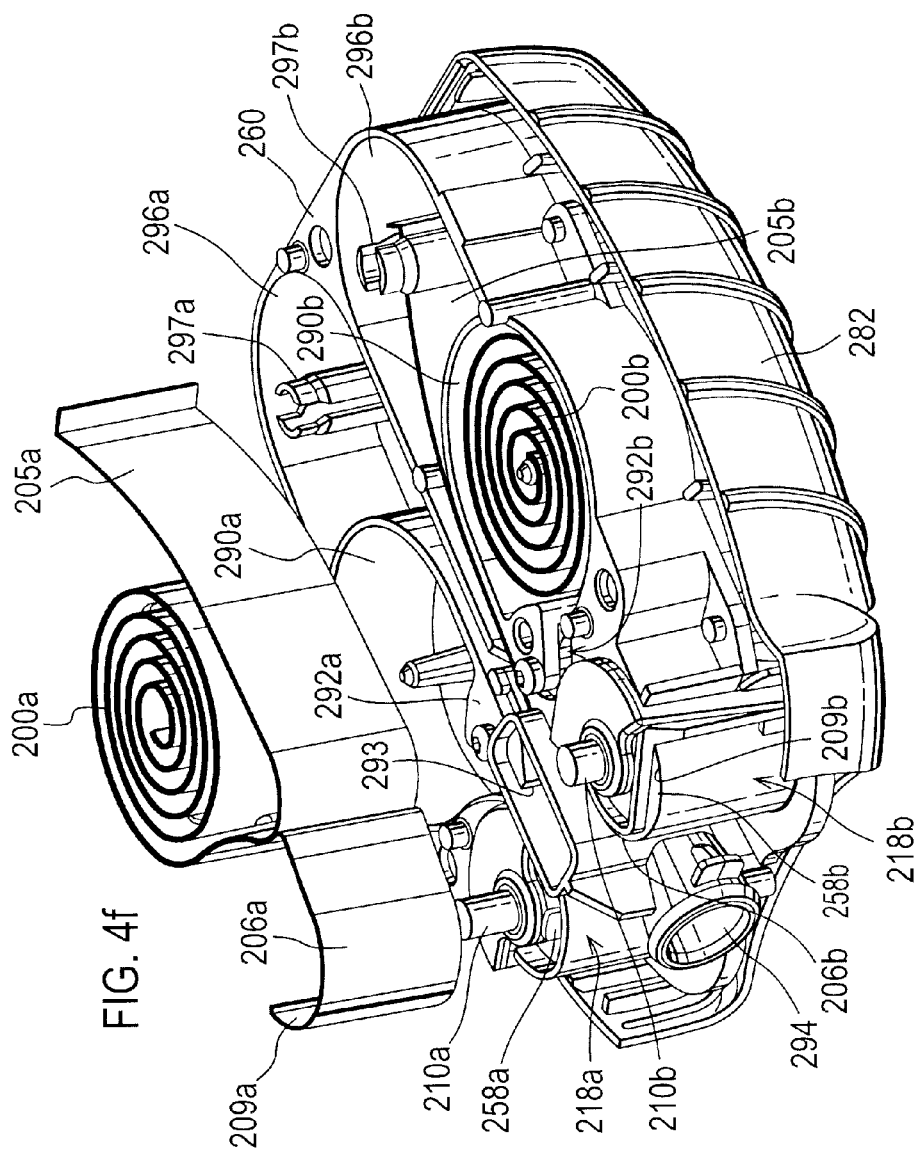

Thus, FIG. 4f shows the assembly unit of FIG. 4e (now having the mouthpiece 281 removed for better visibility of the inner workings). The drug carrier 200b has already been received by the second sheet driver 218b (the indicator pin 210b now in its 'non-popped out' position) and there is now illustrated the insertion of the drug carrier 200a thereinto for attachment to inter alia the first sheet driver 218a.

In more detail, FIG. 4f illustrates a base unit 260 of a drug dispenser herein. The drug-containing blister strips 200a, 200b are arranged to be accommodated within respective left and right chambers 290a, 290b of the base unit 260. Within the dispenser, each blister strip 200a, 200b engages in respective multi-pocket index wheel 292a, 292b, and successive pockets are thereby guided towards a central opening station 293. The rotation of the index wheels 292a, 292b is coupled together by the gear train 265 such as shown in FIG. 4b. At the opening station 293, the lid foil 206a, 206b and base foil 205a, 206b parts of each strip 200a, 200b are peelably separable about beak (not clearly visible) to present powder from each respective opened pocket thereof to a manifold 294. The resulting empty base foil 205a coils up in respective base take-up chambers 296a, 296b. A base foil anchor 297a, 297b anchors the end of each respective base foil 205a, 205b in its chamber 296a, 296b.

The looped end 209a, 209b of each lid foil 206a, 206b of each carrier 200a, 200b is received by upwardly standing hook 258a, 258b part of its respective torsion hub 250a, 250b, as previously described.

FIG. 4g shows the assembly unit of FIG. 4f, but now with both drug carriers 200a, 200b received and the mouthpiece 281 replaced. A second protective retainer plate 269 has also been applied together with a dose counter unit 298, such as of the type disclosed in U.S. Ser. No. 10/597,551 (WO-A-2005/079727), previously incorporated herein by reference. Both drug carriers 200a, 200b have been attached to their respective sheet drivers 218a, 218b so that the pins 210a, 210b are now in their depressed (i.e. 'non-popped out') positions and the respective hubs 250a, 250b are in their loaded positions on the bases 220a, 220b, as described above.

Figure 4H:
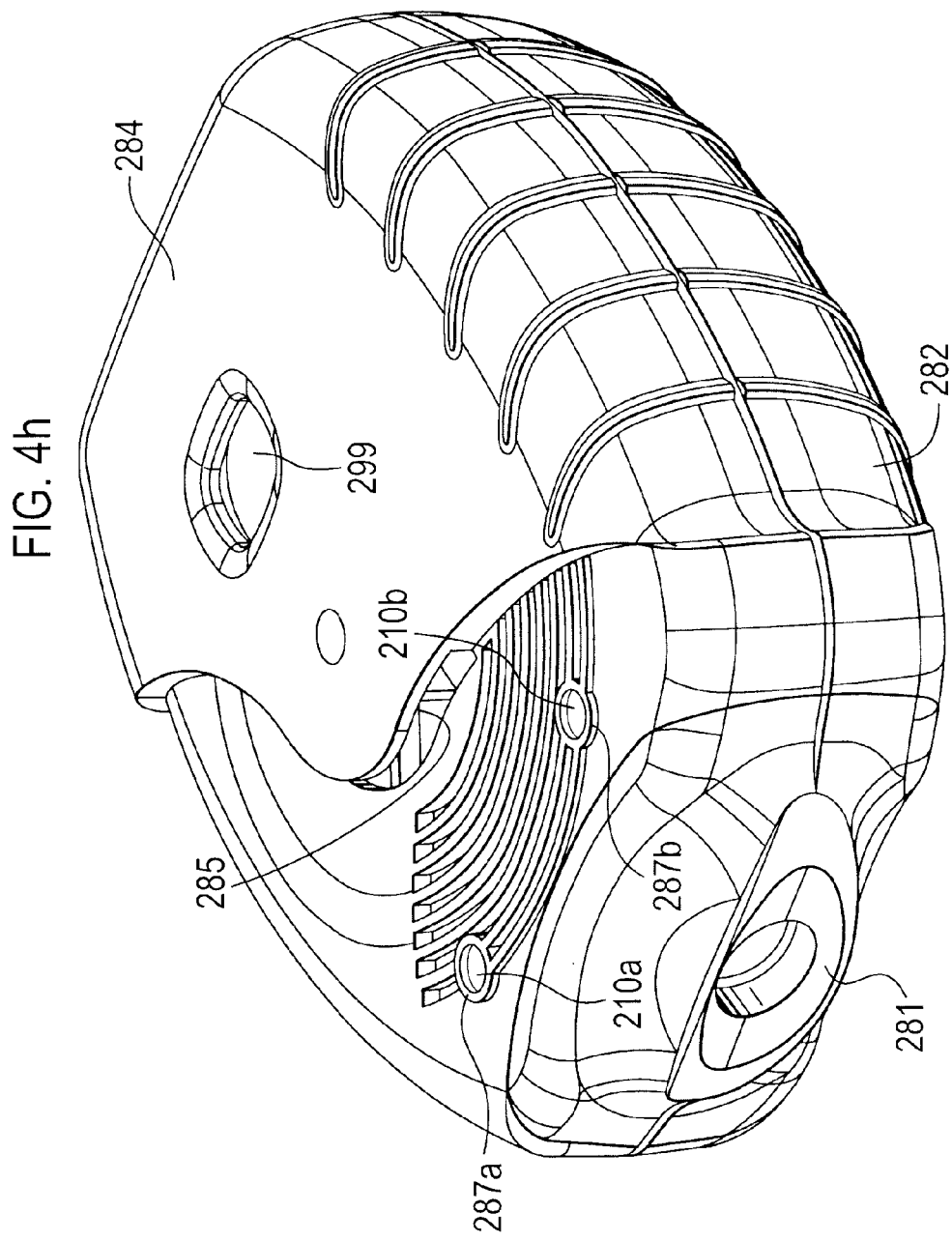

FIG. 4h shows the assembly unit of FIG. 4g, but with the second shell housing part 284 now applied. The second shell housing part 284 defines a curved slot form aperture 285, which allows access to the primary ratcheted gear (not clearly visible) and which, as will become clear from the later description, is arranged for receipt of second drive arm 274b of movable mouthpiece cover 286. A window 299 allows for viewing of the dose count of the dose counter 298. The second shell housing part 284 further defines a pair of pin apertures 287a, 287b through which the heads of respective indicator pins 210a, 210b may be seen. It will again be appreciated that the pins 210a, 210b are in their 'non-popped out' state corresponding to the situation where no lid sheet 206a, 206b 'failure' is detected (i.e. normal dispenser operation).

Figure 4I:
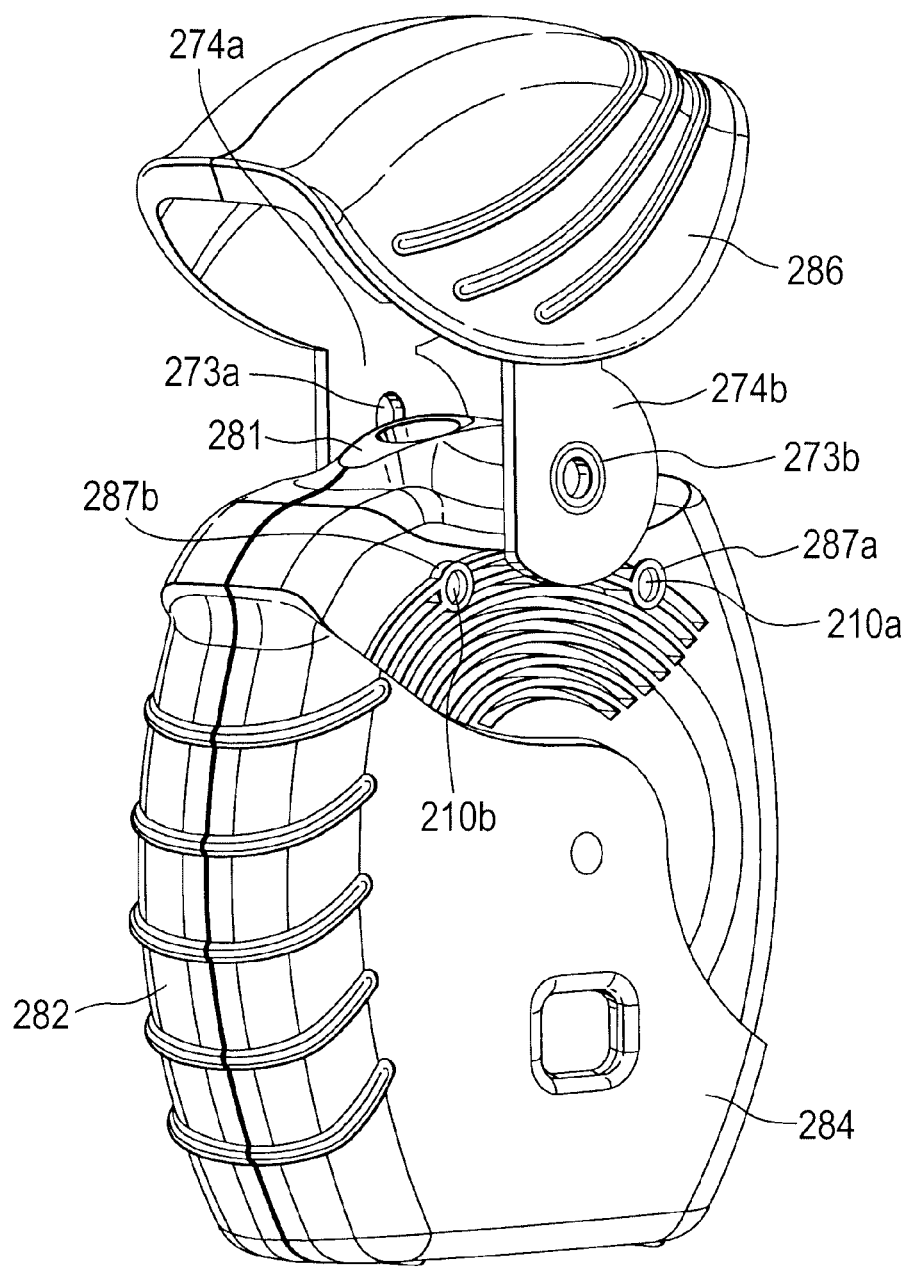
Figure 4J:
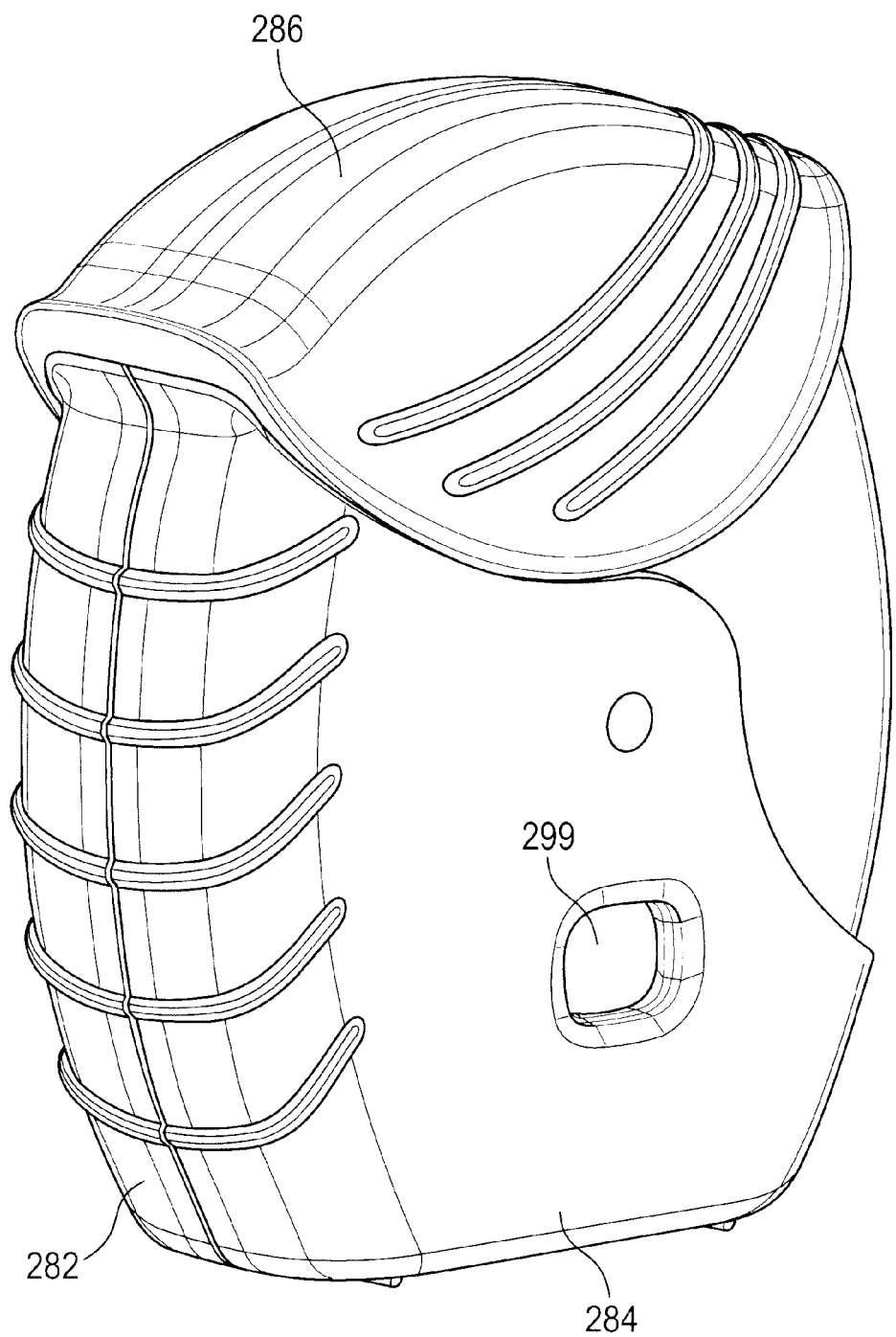

FIG. 4i shows the assembly unit of FIG. 4h, now standing on its base and with movable mouthpiece cover 286 now being applied to provide the full dispenser device as shown in FIG. 4j. First drive arm 274a of the movable mouthpiece cover 286 is received by the curved slot form aperture 283 of the first housing part 282 (see FIG. 4d) and similarly second drive arm 274b thereof is received by the curved slot form aperture 285 of the second housing part 284. When so-received the movable mouthpiece cover 286 mounts to the dispenser device for rotation about a pivot point (not visible) by means of respective mounting holes 273a, 273b provided to each drive arm 274a, 274b such that the mouthpiece cover 286 may be rotated about the axis of the primary index gear 270 and its associated ratchet unit 272, to which it is coupled.

More specifically, one of the mounting holes 273a mounts to the ratchet unit 272 so that the ratchet unit 272 rotates in unison with the mouthpiece cover 286.

In use, actuation of the sheet drivers 218a, 218b is by the user or patient fully opening the movable mouthpiece cover 286 by hand (i.e. manually) to rotate the ratchet unit 272 and thereby in turn rotate the primary index gear 270, which accordingly results in transfer of drive through gear train 265 to inter alia the geared drive surfaces 225a, 225b of the bases 220a, 220b of both of the sheet drivers 218a, 218b. Thus, patient opening of the movable mouthpiece cover 286 provides the means for advancing the sheet drivers 218a, 218b, and hence the individual drug doses held within the pockets of the drug carriers 200a, 200b.

In a subtle aspect, the interaction of the mounting hole 273b of the second drive arm 274b of the mouthpiece cover 286 with the ratchet unit 272 is arranged such that drive is only transferred to the primary index gear 270 when the mouthpiece cover 286 is moved to its fully open position. Thus, 'incomplete' movement of the mouthpiece cover 286 from a first position, in which the mouthpiece 281 is covered, to a second position, in which the mouthpiece 281 is only part-uncovered does not result in transfer of such drive. However, further movement of the mouthpiece cover 286 from that second position to a third position, in which the mouthpiece 281 is fully uncovered results in transfer of the necessary drive to the primary index gear 270, and hence in actuation of the internal dispensing mechanism.

Moreover, the ratchet unit 272 acts to provide that closure of the mouthpiece cover 286 does not result in drive being transmitted to the gear train 265, just resetting of the ratchet unit 272. In other words, a one-way (forward) drive is provided by the connection of the mouthpiece cover 286 to the ratchet unit 272.

In use, the first principal function of each torsion hub sheet driver 218a, 218b is to ensure a roughly constant driving tension is provided to each strip 200a, 200b over the course of each entire strip length. In particular, each torsion hub 250a, 250b acts to compensate for the variation in drive tension associated with the increase in the effective winding diameter of each hub 250a, 250b as used lid foils 106a, 106b gradually becomes wrapped therearound. Thus, uniform indexing of each strip 200a, 200b may be maintained over the entire strip length.

In a little more detail, the hubs 250a, 250b are effectively 'floating' on the bases 220a, 220b in their loaded position. When the bases 220a, 220b are rotated in the lid sheet wind-up direction (forwardly) on opening of the mouthpiece cover 286, the lid sheets 206a, 206b and base sheets 205a, 205b are also advanced by the other elements of the complex gear train 265 so that the hubs 250a, 250b rotate forwardly with the bases 220a, 220b to wind on the lid sheets 206a, 206b and a new pocket of each drug carrier 200a, 200b is peeled open for inhalation of the contents thereof by a patient inhaling at the mouthpiece 281. The gear train 265 is such that the bases 220a, 220b are rotated the same angular amount upon each mouthpiece cover 286 opening event. However, as the lid sheets 206a, 206b wind-up more and more on the respective winding hub 250a, 250b, the effective winding diameter of the hubs 250a, 250b increases, as a result of which there is a tendency for the sheet driver 218a, 218b to try to pull-off more lid sheet 206a, 206b than is being released. When this occurs the increased tension created in the lid sheet 206a, 206b pulls on the hub post 258a, 258b so that the hubs 250a, 250b "slip" rearwardly on the bases 220a, 200b until the balance between the torsion spring force and the lid sheet tension is restored.

More generally, the sheet drivers 218a, 218b accommodate variations in the tension in the associated lid sheets 206a, 206b. If the tension in the lid sheets 206a, 206b is greater that the torsion spring force, then the hubs 250a, 250b slip rearwardly on the bases 220a, 220b, whereas if the torsion spring force is greater than the tension in the lid sheets 206a, 206b, then the hubs 250a, 250b slip forwardly on the bases 220a, 220b, each slippage happening until the forces are balanced.

In normal use, the dispenser is primed by means of the movable mouthpiece cover 286 to drivably actuate each sheet driver 218a, 218b associated with each carrier 200a, 200b, thereby causing the leading pocket thereof to be peeled open. Each torsion hub 250a, 250b acts to provide any necessary drive compensation, as described above. To access the contents of the opened pockets the patient then breathes in through the mouthpiece 281. This results in negative pressure being transmitted through manifold 294 to the opened leading pocket of each strip 200a, 200b at the opening station 293. This, in turn, results in the drug powder formulation contained within each of the opened pockets being drawn out through the common manifold 294 to the mouthpiece 281 and hence to the patient as an inhaled combination drug dose. It will be appreciated that mixing of each separately delivered component of the combined drug product happens as the powder is transported through the manifold 294 from each opened pocket to the mouthpiece 281.

In use, the second principal function of each torsion hub sheet driver 218a, 218b is to indicate by way of the indicator pin 210a, 210b thereof when a loss of tension associated with damage of either drug carrier 200a, 200b is encountered during use of the drug dispenser. Such damage causes the drug dispenser to 'fail' to dispense drug properly. The basic indicator pin mechanism has already been described in relation to FIGS. 3a to 3c. In embodiments, the 'popping out' of either one or both of the indicator pins 210a, 210b from its sheet driver 218a, 218b, and thus from its respective pin apertures 287a, 287b of the second shell housing part 284, is used as a visual indicator of the 'failure' of the dispenser. The head of the pins 210a, 210b may therefore be coloured (e.g. differently from, or to contrast with, the colour(s) of the surrounding dispenser parts) or carry indicia. Such 'popping out' of either one or both of the indicator pins 210a, 210b may also, or instead, be used to lock one or more elements of the dispensing mechanism of the dispenser, thereby preventing its further use.

The dispenser whose assembly has been described in relation to FIGS. 4a to 4j is arranged such that the 'popping out' of either one or both of the indicator pins 210a, 210b results in locking of the movable mouthpiece cover 286, thereby preventing further actuation of the dispenser, noting that the mouthpiece cover 286 also functions as the actuating member of the dispenser. This function is further described in relation to FIGS. 5a to 5c and FIGS. 6a to 6c, which illustrate two separate 'failure' modes.

Referring now to FIG. 5a, there is shown the dispenser with the movable mouthpiece cover 286 in its fully open position. This corresponds to a situation where the patient has sought to actuate the dispenser by fully opening the mouthpiece cover 286 to drive on the internal dispensing mechanism of the dispenser (i.e. to rotate the primary index gear 270 to transfer drive through gear train 265 to the geared drive surfaces 225a, 225b of the bases 220a, 220b of both of the sheet drivers 218a, 218b and so on). First indicator pin 210a (of first sheet driver 218a), however, is in its 'popped out' position, projecting from the pin aperture 287a, thereby indicating a 'failure' associated with the first lid sheet 206a. Such 'failure' has already been described in more detail earlier, in particular in relation to FIG. 3c. The second indicator pin 210b is still recessed in its pin aperture 287b ('non-popped out' position) indicating that the second lid sheet 206b has not failed. But 'failure' of one lid sheet 206a is enough for the dispenser as a whole to be deemed to have 'failed' because the dose to be dispensed includes drug portions from both first 200a and second 200b drug carriers thereof. The patient may notice that the first indicator pin 210a has 'popped out' and therefore stop using the device, but if not a 'lock out' feature is also provided, which prevents further use thereof.

Figure 5C:
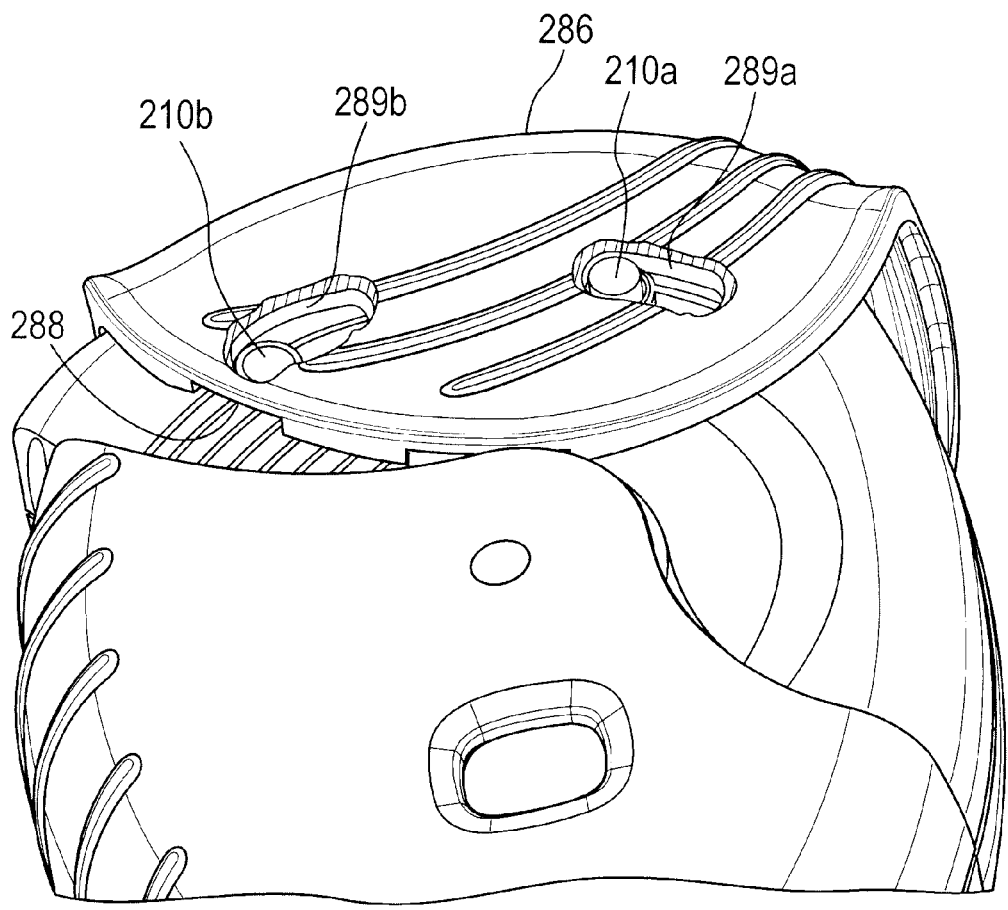

In more detail, FIG. 5b shows when the patient starts to (re)close the mouthpiece cover 286. The inner surface of the cover 286 may be seen to be provided with a recess having a ramped surface 288, which ramps over the 'popped out' first indicator pin 210a and causes it to be temporarily depressed against the bias of the compression spring 238, thereby allowing the cover 286 to be fully closed. When the cover 286 is in the fully closed position of FIG. 5c, however, the first indicator pin 210a springs out again into locking engagement with a first indent or groove 289a formed in the inner surface of the cover 286 (shown in part cut-away view), thereby locking the cover 286 against being (re)opened. It may also be seen that the inner surface of the cover 286 is provided with a second indent or groove 289b (again shown in part cut-away view), which locates over the second indicator pin 210b, but does not lockingly engage it in this particular example because that pin 210b is not in its 'popped out' position (i.e. no 'failure' of the second drug carrier 200b). All further use of the dispenser is thereby prevented. Further, in the 'locked out' state the mouthpiece 281 is covered over thereby preventing any undesirable partial use of the dispenser (e.g. to dispense drug only from the undamaged drug carrier 200b).

Figure 6A:
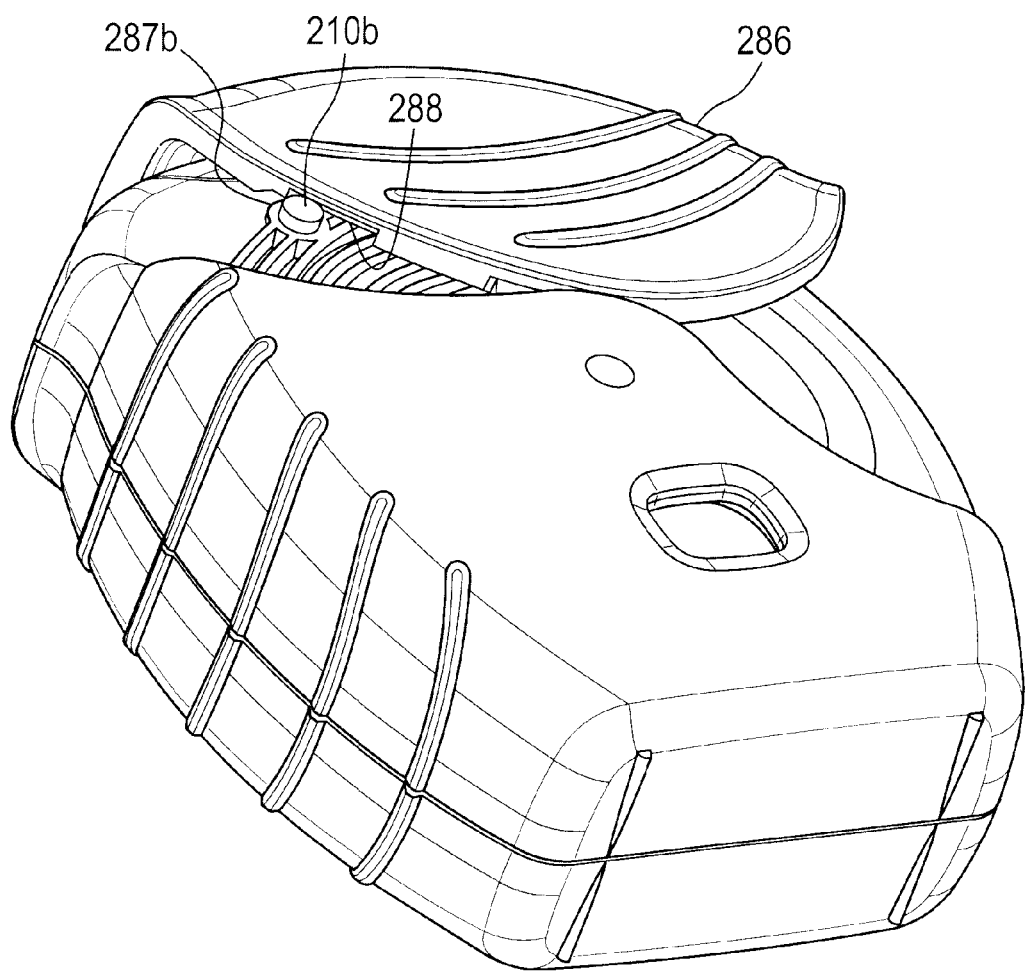
FIGS. 6a to 6c show perspective views of a 'lock out' of the drug dispenser by the sheet driver/spool in a second 'failure' mode.

A second 'failure' mode is now described. Referring to FIG. 6a, there is shown the dispenser with the movable mouthpiece cover 286 in a part-open position. This corresponds to a situation where the patient has sought to actuate the dispenser by opening the mouthpiece cover 286 to drive on the internal dispensing mechanism of the dispenser (i.e. to rotate the primary index gear 270 to transfer drive through gear train 265 to the geared drive surfaces 225a, 225b of the bases 220a, 220b of both of the sheet drivers 218a, 218b and so on). Second indicator pin 210b (of second sheet driver 218b) is in its 'popped out' position, projecting from its pin aperture 287b, thereby indicating a 'failure' associated with second lid sheet 206b. Such 'failure' has already been described in more detail earlier, in particular relation to FIG. 3c. As before, the patient may notice that the second indicator pin 210b has 'popped out' and therefore stop using the device at this stage, but if not a 'lock out' feature is also provided, which prevents further use thereof.

Figure 6B:
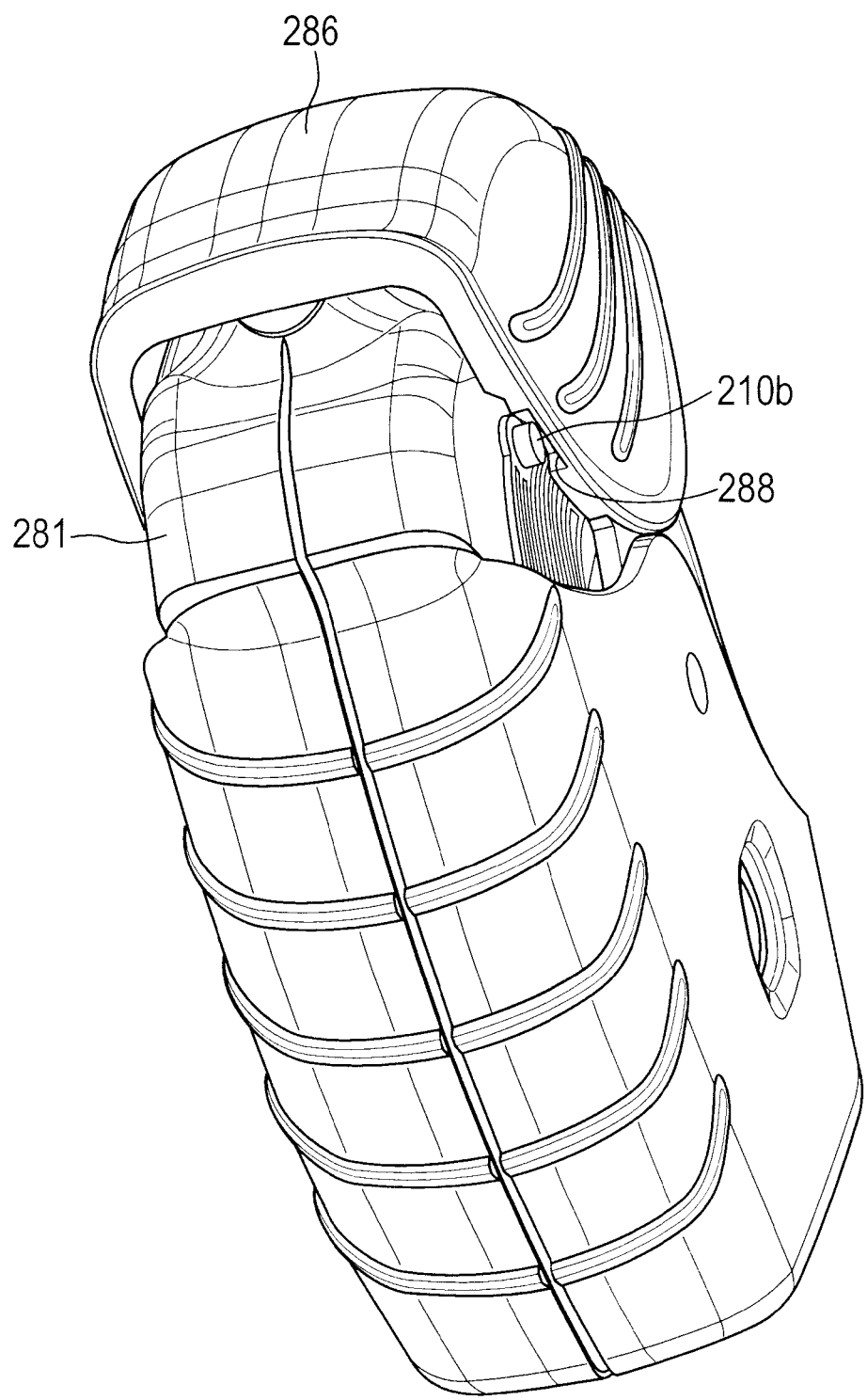
Figure 6C:
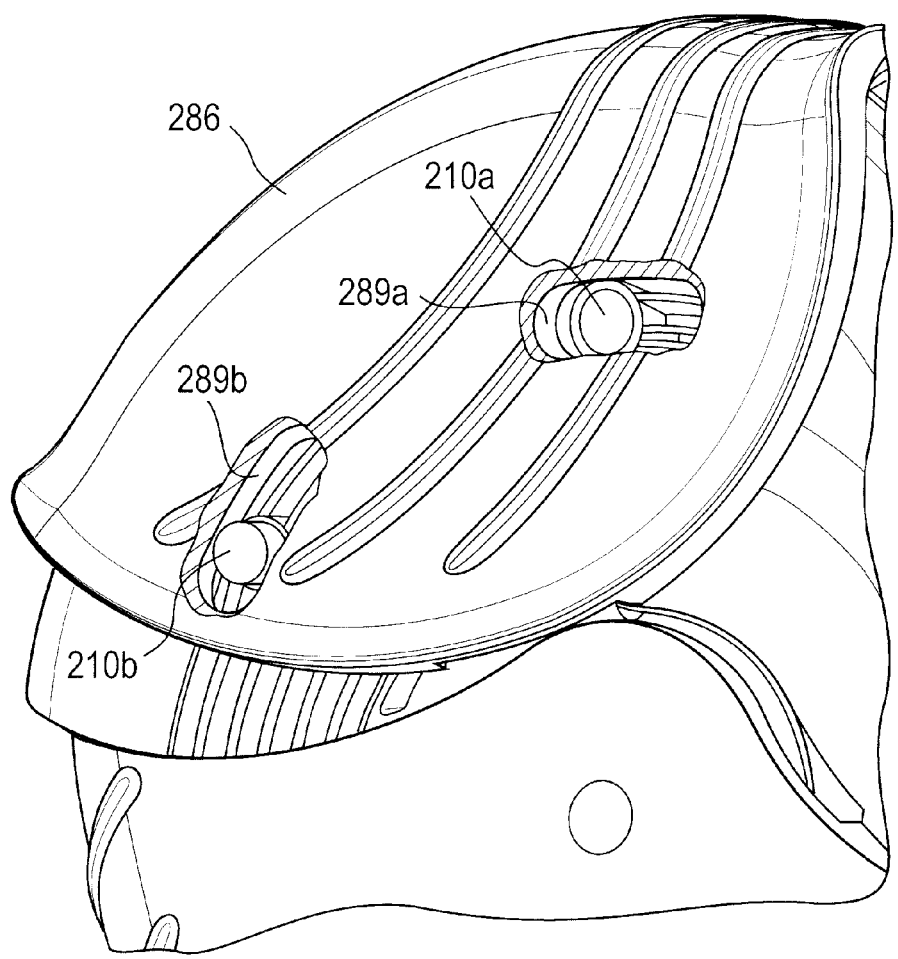

In more detail, FIG. 6b shows when the patient starts to (re)close the mouthpiece cover 286. The ramped surface 288 this time ramps over the 'popped out' second indicator pin 210b and causes it to be temporarily depressed, thereby allowing the cover 286 to be fully closed. When the cover 286 is in the fully closed position of FIG. 6c, the second indicator pin 210b springs out again into locking engagement with the second indent 289b (shown in part cut-away view), thereby locking the cover 286 against being opened again. As before, all further use of the dispenser is prevented and the mouthpiece 281 is covered over.

It is finally noted that in normal use of the dispenser, with no damage to either drug carrier 200a, 200b, both pins 210a, 210b will be in the 'non-popped out' position and thus recessed in the pin apertures 287a, 287b so movement of the movable mouthpiece cover 286 is not impeded.

It will be appreciated that the torsion spring used in the first sheet driver 218a could equally be used in the second sheet driver 218b, and vice versa. In fact, the same torsion spring could be used in both sheet drivers 218a, 218b, if desired. This is because rotating the upper spring leg in either direction to the lower spring leg generates a biasing force in the torsion spring in the opposite direction.

It will also be observed in FIG. 3a that the top surface 251 of the hub 250 is provided with a circumferential array of differently sized indents (not labelled). Ideally, the indent array of the hub 250b for the second sheet driver 218a will be in the reverse order shown in FIG. 3a. This then makes it easier for the automated assembly lines for the sheet driver and/or the dispenser device to recognise and/or handle the different hubs 250a, 250b and ensure they are used for the correct sheet driver 218a, 218b. Of course, the indent array shown in FIG. 3a could be used for the hub 250b of the second sheet driver 218b and the reverse order for the hub 250a of the first sheet driver 218a. There is also no reason why different indent arrays than shown could not be used.

It will further be appreciated that the present invention extends to other sheet drivers (or spools) than shown, and further that such sheet drivers (or spools) may be for use with strips or tapes other than that shown in FIG. 1. Moreover, the present invention is not restricted to use with drug-containing sheets or tapes or drug dispensing devices.

It will yet further be appreciated that the 'Summary of the invention' section and the claims may disclose additional details, modifications or adaptations for the exemplary sheet driver described with reference to the accompanying FIGURES.

The dispenser device herein is particularly, but not exclusively, for dispensing powdered drug formulations, particularly for the treatment of respiratory disorders such as asthma and chronic obstructive pulmonary disease (COPD), bronchitis and chest infections.

More generally, the device may be used in delivery of a drug (e.g. powder) formulation based on one or more of the drugs listed hereinbelow. Where the device is to be used with just a single drug carrier, the formulation in that carrier may comprise just one of the listed drugs (a monotherapy) or a plurality of the listed drugs (combination therapy). Where the device is for use with plural (in particular two) drug carriers, each carrier may contain a formulation comprising one or more of the listed drugs, one carrier containing at least one drug not found in the, or at least one of the other, carrier(s). Where the device is for use with two drug carriers, the drug formulation in one carrier comprises a drug not found in the other carrier. Typically, each carrier will have different drug(s) than the other carrier.

Appropriate drugs may thus be selected from, for example, analgesics, e.g., codeine, dihydromorphine, ergotamine, fentanyl or morphine; anginal preparations, e.g., diltiazem; antiallergics, e.g., cromoglycate (e.g. as the sodium salt), ketotifen or nedocromil (e.g. as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g. as the dipropionate ester), fluticasone (e.g. as the propionate ester), flunisolide, budesonide, rofleponide, mometasone e.g. as the furoate ester), ciclesonide, triamcinolone (e.g. as the acetonide) or 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester; antitussives, e.g., noscapine; bronchodilators, e.g., albuterol (e.g. as free base or sulphate), salmeterol (e.g. as xinafoate), ephedrine, adrenaline, fenoterol (e.g. as hydrobromide), salmefamol, carbuterol, mabuterol, etanterol, naminterol, clenbuterol, flerbuterol, bambuterol, indacaterol, formoterol (e.g. as fumarate), isoprenaline, metaproterenol, phenylephrine, phenylpropanolamine, pirbuterol (e.g. as acetate), reproterol (e.g. as hydrochloride), rimiterol, terbutaline (e.g. as sulphate), isoetharine, tulobuterol or 4-hydroxy-7-[2-[[2-[[3-(2-phenylethoxy)propyl]sulfonyl]ethyl]amino]ethyl-2(3H)-benzothiazolone; adenosine 2a agonists, e.g. 2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3, 4-diol (e.g. as maleate); α$_4$ integrin inhibitors e.g. (2S)-3-[4-({[4-(aminocarbonyl)-1-piperidinyl]carbonyl}oxy)phenyl]-2-[((2S)-4-methyl-2-{[2-(2-methyl phenoxy) acetyl] amino}pentanoyl)amino]propanoic acid (e.g. as free acid or potassium salt), diuretics, e.g., amiloride; anticholinergics, e.g., ipratropium (e.g. as bromide), tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the drugs may be used in the form of salts, (e.g., as alkali metal or amine salts or as acid addition salts) or as esters (e.g., lower alkyl esters) or as solvates (e.g., hydrates) to optimise the activity and/or stability of the drug.

The formulated drug product may in aspects, be a monotherapy (i.e. single active drug containing) product or it may be a combination therapy (i.e. plural active drug containing) product.

Suitable drugs or drug components of a combination therapy product are typically selected from the group consisting of anti-inflammatory agents (for example a corticosteroid or an NSAID), anticholinergic agents (for example, an $M_1$, $M_2$, $M_1/M_2$ or $M_3$ receptor antagonist), other $β_2$-adrenoreceptor agonists, antiinfective agents (e.g. an antibiotic or an antiviral), and antihistamines. All suitable combinations are envisaged.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1, 4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-(2,2,3,3-tetramethycyclopropylcarbonyl)oxy-androsta-1,4-diene-17β-carbothioic acid S-cyanomethyl ester, 6α,9α-difluoro-11β-hydroxy-16α-methyl-17α-(1-methycyclopropylcarbonyl)oxy-3-oxo-androsta-1,4-diene-17β-carbothioic acid S-fluoromethyl ester and 9α, 21 dichloro-11β, 17αmethyl-1,4 pregnadiene 3,20 dione-17-[2']furoate (mometasone furoate).

Further corticosteroids are described in WO02/088167, WO02/100879, WO02/12265, WO02/12266, WO05/005451, WO05/005452, WO06/072599 and WO06/072600.

Non-steroidal compounds having glucocorticoid agonism that may possess selectivity for transrepression over transactivation and that may be useful in combination therapy through the manifold herein are disclosed WO03/082827, WO98/54159, WO04/005229, WO04/009017, WO04/018429, WO03/104195, WO03/082787, WO03/082280, WO03/059899, WO03/101932, WO02/02565, WO01/16128, WO00/66590, WO03/086294, WO04/026248, WO03/061651, WO03/08277, WO06/000401, WO06/000398 and WO06/015870.

Suitable NSAIDs include sodium cromoglycate, nedocromil sodium, phosphodiesterase (PDE) inhibitors (e.g. theophylline, PDE4 inhibitors or mixed PDE3/PDE4 inhibitors), leukotriene antagonists, inhibitors of leukotriene synthesis, iNOS inhibitors, tryptase and elastase inhibitors, beta-2 integrin antagonists and adenosine receptor agonists or antagonists (e.g. adenosine 2a agonists), cytokine antagonists (e.g. chemokine antagonists), inhibitors of cytokine synthesis or 5-lipoxygenase inhibitors. Examples of iNOS inhibitors include those disclosed in WO93/13055, WO98/30537, WO02/50021, WO95/34534 and WO99/62875. Examples of CCR3 inhibitors include those disclosed in WO02/26722.

Suitable bronchodilators are $\beta_2$-adrenoreceptor agonists, including salmeterol (which may be a racemate or a single enantiomer, such as the R-enantiomer), for instance salmeterol xinafoate, salbutamol (which may be a racemate or a single enantiomer, such as the R-enantiomer), for instance salbutamol sulphate or as the free base, formoterol (which may be a racemate or a single diastereomer, such as the R,R-diastereomer), for instance formoterol fumarate or terbutaline and salts thereof. Other suitable $\beta_2$-adrenoreceptor agonists are 3-(4-{[6-({(2R)-2-hydroxy-2-[4-hydroxy-3-(hydroxymethyl)phenyl]ethyl}amino)hexyl]oxy}butyl)benzenesulfonamide, 3-(3-{[7-({(2R)-2-hydroxy-2-[4-hydroxy-3-hydroxymethyl) phenyl]ethyl}-amino)heptyl]oxy}propyl) benzenesulfonamide, 4-{(1R)-2-[(6-{2-[(2,6-dichlorobenzyl)oxy]ethoxy}hexyl)amino]-1-hydroxyethyl}-2-(hydroxymethyl) phenol, 4-{(1R)-2-[(6-{4-[3-(cyclopentylsulfonyl)phenyl]butoxy}hexyl)amino]-1-hydroxyethyl}-2-(hydroxymethyl) phenol, N-[2-hydroxyl-5-[(1R)-1-hydroxy-2-[[2-4-[[(2R)-2-hydroxy-2-phenylethyl]amino]phenyl]ethyl]amino]ethyl]phenyl]formamide, and N-2{2-[4-(3-phenyl-4-methoxyphenyl)aminophenyl]ethyl}-2-hydroxy-2-(8-hydroxy-2(1H)-quinolinon-5-yl)ethylamine, and 5-[(R)-2-(2-{4-[4-(2-amino-2-methyl-propoxy)-phenylamino]-phenyl}-ethylamino)-1-hydroxy-ethyl]-8-hydroxy-1H-quinolin-2-one. Preferably, the $\beta_2$-adrenoreceptor agonist is a long acting $\beta_2$-adrenoreceptor agonist (LABA), for example a compound which provides effective bronchodilation for about 12 hours or longer.

Other $\beta_2$-adrenoreceptor agonists include those described in WO 02/066422, WO 02/070490, WO 02/076933, WO 03/024439, WO 03/072539, WO 03/091204, WO 04/016578, WO 2004/022547, WO 2004/037807, WO 2004/037773, WO 2004/037768, WO 2004/039762, WO 2004/039766, WO01/42193 and WO03/042160.

Suitable phosphodiesterase 4 (PDE4) inhibitors include compounds that are known to inhibit the PDE4 enzyme or which are discovered to act as a PDE4 inhibitor, and which are only PDE4 inhibitors, not compounds which inhibit other members of the PDE family as well as PDE4. Generally it is preferred to use a PDE4 inhibitor which has an $IC_{50}$ ratio of about 0.1 or greater as regards the $IC_{50}$ for the PDE4 catalytic form which binds rolipram with a high affinity divided by the $IC_{50}$ for the form which binds rolipram with a low affinity. For the purposes of this disclosure, the cAMP catalytic site which binds R and S rolipram with a low affinity is denominated the "low affinity" binding site (LPDE 4) and the other form of this catalytic site which binds rolipram with a high affinity is denominated the "high affinity" binding site (HPDE 4). This term "HPDE4" should not be confused with the term "hPDE4" which is used to denote human PDE4.

A method for determining $IC_{50}$s ratios is set out in U.S. Pat. No. 5,998,428 which is incorporated herein in full by reference as though set out herein. See also PCT application WO 00/51599 for an another description of said assay.

Suitable PDE4 inhibitors include those compounds that have a salutary therapeutic ratio, i.e., compounds which preferentially inhibit cAMP catalytic activity where the enzyme is in the form that binds rolipram with a low affinity, thereby reducing the side effects that apparently are linked to inhibiting the form that binds rolipram with a high affinity. Another way to state this is that the preferred compounds will have an $IC_{50}$ ratio of about 0.1 or greater as regards the $IC_{50}$ for the PDE4 catalytic form that binds rolipram with a high affinity divided by the $IC_{50}$ for the form that binds rolipram with a low affinity.

A further refinement of this standard is that of one wherein the PDE4 inhibitor has an $IC_{50}$ ratio of about 0.1 or greater; said ratio is the ratio of the $IC_{50}$ value for competing with the binding of 1 nM of [$^3$H]R-rolipram to a form of PDE4 which binds rolipram with a high affinity over the $IC_{50}$ value for inhibiting the PDE4 catalytic activity of a form which binds rolipram with a low affinity using 1 μM[$^3$H]-cAMP as the substrate.

Most suitable are those PDE4 inhibitors which have an $IC_{50}$ ratio of greater than 0.5, and particularly those compounds having a ratio of greater than 1.0. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl) cyclohexan-1-ol]; these are examples of compounds which bind preferentially to the low affinity binding site and which have an $IC_{50}$ ratio of 0.1 or greater.

Other suitable drug compounds include: cis-4-cyano-4-[3-(cyclopentyloxy)-4-methoxyphenyl]cyclohexane-1-carboxylic acid (also known as cilomalast) disclosed in U.S. Pat. No. 5,552,438 and its salts, esters, pro-drugs or physical forms; AWD-12-281 from elbion (Hofgen, N. et al. 15th EFMC Int Symp Med Chem (September 6-10, Edinburgh) 1998, Abst P. 98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (September 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Further compounds are disclosed in WO04/024728, WO04/056823 and WO04/103998, all of Glaxo Group Limited.

Suitable anticholinergic agents are those compounds that act as antagonists at the muscarinic receptor, in particular those compounds, which are antagonists of the $M_1$ or $M_3$ receptors, dual antagonists of the $M_1/M_3$ or $M_2/M_3$ receptors or pan-antagonists of the $M_1/M_2/M_3$ receptors. Exemplary compounds include the alkaloids of the belladonna plants as illustrated by the likes of atropine, scopolamine, homatropine, hyoscyamine; these compounds are normally administered as a salt, being tertiary amines.

Other suitable anti-cholinergics are muscarinic antagonists, such as (3-endo)-3-(2,2-di-2-thienylethenyl)-8,8-dimethyl-8-azoniabicyclo[3.2.1]octane iodide, (3-endo)-3-(2-cyano-2,2-diphenylethyl)-8,8-dimethyl-8-azoniabicyclo[3.2.1]octane bromide, 4-[hydroxy(diphenyl)methyl]-1-{2-[(phenylmethyl)oxy]ethyl}-1-azonia bicyclo[2.2.2]octane bromide, (1R,5S)-3-(2-cyano-2,2-diphenylethyl)-8-methyl-8-{2-[(phenylmethyl)oxy]ethyl}-8-azoniabicyclo[3.2.1]octane bromide, (endo)-3-(2-methoxy-2,2-di-thiophen-2-yl-ethyl)-8,8-dimethyl-8-azonia-bicyclo[3.2.1]octane iodide, (endo)-3-(2-cyano-2,2-diphenyl-ethyl)-8,8-dimethyl-8-azonia-bicyclo[3.2.1]octane iodide, (endo)-3-(2-carbamoyl-2,2-diphenyl-ethyl)-8,8-dimethyl-8-azonia-bicyclo[3.2.1]octane iodide, (endo)-3-(2-cyano-2,2-di-thiophen-2-yl-ethyl)-8,8-dimethyl-8-azonia-bicyclo[3.2.1]octane iodide, and (endo)-3-{2,2-diphenyl-3-[(1-phenyl-methanoyl)-amino]-propyl}-8,8-dimethyl-8-azonia-bicyclo[3.2.1]octane bromide.

Particularly suitable anticholinergics include ipratropium (e.g. as the bromide), sold under the name Atrovent, oxitropium (e.g. as the bromide) and tiotropium (e.g. as the bromide) (CAS-139404-48-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118. Also of interest are revatropate (for example, as the hydrobromide, CAS 262586-79-8) and LAS-34273 which is disclosed in WO01/04118, darifenacin (CAS 133099-04-4, or CAS 133099-07-7 for the hydrobromide sold under the name Enablex), oxybutynin (CAS 5633-20-5, sold under the name Ditropan), terodiline (CAS 15793-40-5), tolterodine (CAS 124937-51-5, or CAS 124937-52-6 for the tartrate, sold under the name Detrol), otilonium (for example, as the bromide, CAS 26095-59-0, sold under the name Spasmomen), trospium chloride (CAS 10405-02-4) and solifenacin (CAS 242478-37-1, or CAS 242478-38-2 for the succinate also known as YM-905 and sold under the name Vesicare).

Other anticholinergic agents include compounds disclosed in U.S. Ser. No. 60/487,981 and U.S. Ser. No. 60/511,009.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. Examples include ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic the tertiary amine group with piperizine or piperidine.

Examples of H1 antagonists include, without limitation, amelexanox, astemizole, azatadine, azelastine, acrivastine, brompheniramine, cetirizine, levocetirizine, efletirizine, chlorpheniramine, clemastine, cyclizine, carebastine, cyproheptadine, carbinoxamine, descarboethoxyloratadine, doxylamine, dimethindene, ebastine, epinastine, efletirizine, fexofenadine, hydroxyzine, ketotifen, loratadine, levocabastine, mizolastine, mequitazine, mianserin, noberastine, meclizine, norastemizole, olopatadine, picumast, pyrilamine, promethazine, terfenadine, tripelennamine, temelastine, trimeprazine and triprolidine, particularly cetirizine, levocetirizine, efletirizine and fexofenadine.

Exemplary H1 antagonists are as follows:
Ethanolamines: carbinoxamine maleate, clemastine fumarate, diphenylhydramine hydrochloride, and dimenhydrinate.
Ethylenediamines: pyrilamine amleate, tripelennamine HCl, and tripelennamine citrate.
Alkylamines: chlrophenirmaine and its salts such as the maleate salt, and acrivastine.
Piperazines: hydroxyzine HCl, hydroxyzine pamoate, cyclizine HCl, cyclizine lactate, meclizine HCl, and cetirizine HCl.
Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with a PDE4 inhibitor.

The drug, or one of the drugs, may be an H3 antagonist (and/or inverse agonist). Examples of H3 antagonists include, for example, those compounds disclosed in WO2004/035556 and in WO2006/045416.

Other histamine receptor antagonists which may be used include antagonists (and/or inverse agonists) of the H4 receptor, for example, the compounds disclosed in Jablonowski et al., *J. Med. Chem.* 46:3957-3960 (2003).

In respect of combination products, co-formulation compatibility is generally determined on an experimental basis by known methods and may depend on chosen type of drug dispenser device action.

The drug components of a combination product are suitably selected from the group consisting of anti-inflammatory agents (for example a corticosteroid or an NSAID), anticholinergic agents (for example, an $M_1$, $M_2$, $M_1/M_2$ or $M_3$ receptor antagonist), other $\beta_2$-adrenoreceptor agonists, antiinfective agents (e.g. an antibiotic or an antiviral), and antihistamines. All suitable combinations are envisaged.

Suitably, the co-formulation compatible components comprise a $\beta_2$-adrenoreceptor agonist and a corticosteroid; and the co-formulation incompatible component comprises a PDE-4 inhibitor, an anti-cholinergic or a mixture thereof. The $\beta_2$-adrenoreceptor agonists may for example be salbutamol (e.g., as the free base or the sulphate salt) or salmeterol (e.g., as the xinafoate salt) or formoterol (eg as the fumarate salt). The corticosteroid may for example, be a beclomethasone ester (e.g., the dipropionate) or a fluticasone ester (e.g., the propionate) or budesonide.

In one example, the co-formulation compatible components comprise fluticasone propionate and salmeterol, or a salt thereof (particularly the xinafoate salt) and the co-formulation incompatible component comprises a PDE-4 inhibitor, an anti-cholinergic (e.g. ipratropium bromide or tiotropium bromide) or a mixture thereof.

In another example, the co-formulation compatible components comprise budesonide and formoterol (e.g. as the fumarate salt) and the co-formulation incompatible component comprises a PDE-4 inhibitor, an anti-cholinergic (e.g. ipratropium bromide or tiotropium bromide) or a mixture thereof.

Generally, powdered drug particles suitable for delivery to the bronchial or alveolar region of the lung have an aerodynamic diameter of less than 10 micrometers, preferably from 1-6 micrometers. Other sized particles may be used if delivery to other portions of the respiratory tract is desired, such as the nasal cavity, mouth or throat. The drug may be delivered as pure drug, but more appropriately, it is preferred that drugs are delivered together with excipients (carriers) which are suitable for inhalation. Suitable excipients include organic excipients such as polysaccharides (i.e. starch, cellulose and the like), lactose, glucose, mannitol, amino acids, and maltodextrins, and inorganic excipients such as calcium carbonate or sodium chloride. Lactose is a preferred excipient.

Particles of powdered drug and/or excipient may be produced by conventional techniques, for example by micronisation, milling or sieving. Additionally, drug and/or excipient powders may be engineered with particular densities, size ranges, or characteristics. Particles may comprise active agents, surfactants, wall forming materials, or other components considered desirable by those of ordinary skill.

The excipient may be included with the drug via well-known methods, such as by admixing, co-precipitating and the like. Blends of excipients and drugs are typically formulated to allow the precise metering and dispersion of the blend into doses. A standard blend, for example, contains 13000 micrograms lactose mixed with 50 micrograms drug, yielding an excipient to drug ratio of 260:1. Dosage blends with excipient to drug ratios of from 100:1 to 1:1 may be used. At very low ratios of excipient to drug, however, the drug dose reproducibility may become more variable.

The dispenser device described herein is in one aspect suitable for dispensing drug for the treatment of respiratory disorders such as disorders of the lungs and bronchial tracts including asthma and chronic obstructive pulmonary disorder (COPD). In another aspect, the invention is suitable for dispensing drug for the treatment of a condition requiring treatment by the systemic circulation of drug, for example migraine, diabetes, pain relief e.g. inhaled morphine.

The amount of any particular drug compound or a pharmaceutically acceptable salt, solvate or physiologically functional derivative thereof which is required to achieve a therapeutic effect will, of course, vary with the particular compound, the route of administration, the subject under treatment, and the particular disorder or disease being treated. The drugs for treatment of respiratory disorders herein may for example, be administered by inhalation at a dose of from 0.0005 mg to 10 mg, preferably 0.005 mg to 0.5 mg. The dose range for adult humans is generally from 0.0005 mg to 100 mg per day and preferably 0.01 mg to 1.5 mg per day.

It will be understood that the present disclosure is for the purpose of illustration only and the invention extends to modifications, variations and improvements thereto.

What is claimed is:

1. A spool for winding up a tape comprising a rotatable part for rotating the spool, a hub part mounted to the rotatable part for rotation therewith to wind the tape up thereon, a biasing mechanism for biasing the hub part to rotate relative to the rotatable part to a first rotary position, and a fault indicator for indicating a fault in the tape when the hub part is in the first rotary position on the rotatable part, and
   wherein the rotatable part has an axis of rotation and wherein the hub part is mounted co-axially to the rotatable part so as to be rotatable relative thereto about said axis.

2. The spool of claim 1, wherein the fault indicator is movable from a first position to a second position only when the hub part is in the first rotary position, said movement of the fault indicator to the second position indicating a fault in the tape.

3. The spool of claim 2, further comprising a biasing mechanism for biasing the fault indicator to move from the first position to the second position and a latch for latching the fault indicator in the first position thereof when the hub part is not in the first rotary position.

4. The spool of claim 3, wherein the latch is a surface of the hub part which acts on the fault indicator when not in the first rotary position.

5. The spool of claim 2, wherein the fault indicator is housed within the spool when in the first position and protrudes from the spool when in the second position.

6. The spool of claim 1, wherein the fault indicator is carried by the rotatable part.

7. The spool of claim 5, wherein the hub part has an aperture through which the fault indicator is able to protrude when the hub is in the first rotary position.

8. The spool of claim 4, wherein the fault indicator is housed within the spool when in the first position and protrudes from the spool when in the second position, and the hub part has an aperture through which the fault indicator is able to protrude when the hub is in the first rotary position, and wherein the latch surface is a rim of the aperture.

9. The spool of claim 8, wherein the rim of the aperture and the fault indicator have complementary non-circular shapes which are only aligned in the same orientation as each other when the hub part is in the first rotary position.

10. The spool of claim 1, wherein the hub part and the rotatable part have co-operable surfaces for holding the hub part in the first rotary position on the rotatable part.

* * * * *